(12) United States Patent
Neal, II

(10) Patent No.: US 12,114,911 B2
(45) Date of Patent: Oct. 15, 2024

(54) SYSTEM AND METHOD FOR ABLATING A TISSUE SITE BY ELECTROPORATION WITH REAL-TIME PULSE MONITORING

(71) Applicant: AngioDynamics, Inc., Latham, NY (US)

(72) Inventor: Robert Neal, II, Richmond, VA (US)

(73) Assignee: ANGIODYNAMICS, INC., Latham, NY (US)

( * ) Notice: Subject to any disclaimer, the term of this patent is extended or adjusted under 35 U.S.C. 154(b) by 1438 days.

(21) Appl. No.: 14/837,480

(22) Filed: Aug. 27, 2015

(65) Prior Publication Data

US 2016/0058493 A1 Mar. 3, 2016

Related U.S. Application Data

(60) Provisional application No. 62/042,862, filed on Aug. 28, 2014.

(51) Int. Cl.
*A61B 18/12* (2006.01)
*A61B 18/14* (2006.01)
(Continued)

(52) U.S. Cl.
CPC ...... *A61B 18/1233* (2013.01); *A61B 18/1206* (2013.01); *A61B 18/14* (2013.01);
(Continued)

(58) Field of Classification Search
CPC ........... A61B 2018/00642; A61B 2018/00613; A61B 2017/00154; A61B 18/1233; A61B 18/1206; A61B 18/14
See application file for complete search history.

(56) References Cited

U.S. PATENT DOCUMENTS

| 1,329,496 A | 2/1920 | Binkley |
| 1,351,661 A | 8/1920 | Kaufman |

(Continued)

FOREIGN PATENT DOCUMENTS

| AU | 7656800 A | 4/2001 |
| AU | 2002315095 A1 | 12/2002 |

(Continued)

OTHER PUBLICATIONS

International Search Report PCT-US-06-016045_ISR dated Sep. 25, 2007.

(Continued)

*Primary Examiner* — Linda C Dvorak
*Assistant Examiner* — Ryan T Clark
(74) *Attorney, Agent, or Firm* — Kevin P. Radigan; HESLIN ROTHENBERG FARLEY & MESITI P.C.

(57) ABSTRACT

A medical system for ablating a tissue site by electroporation with real-time pulse monitoring during an electroporation treatment procedure is provided. The treatment control module monitors applied pulses and detect an abnormal condition that indicates either an ineffective electroporation of the tissue or an imminent excessive current such as a spark event that may exceed the capacity of the pulse generator. Rather than terminating the procedure entirety, the treatment control module temporarily pauses the procedure to allow the user to adjust the pulse parameters so as to complete the procedure without starting the procedure over again.

23 Claims, 9 Drawing Sheets

(51) Int. Cl.
  *A61B 17/00* (2006.01)
  *A61B 18/00* (2006.01)
(52) U.S. Cl.
  CPC ............ *A61B 2017/00115* (2013.01); *A61B 2017/00119* (2013.01); *A61B 2017/00154* (2013.01); *A61B 2018/00577* (2013.01); *A61B 2018/00613* (2013.01); *A61B 2018/00642* (2013.01); *A61B 2018/00702* (2013.01); *A61B 2018/00708* (2013.01); *A61B 2018/00767* (2013.01)

(56) References Cited

U.S. PATENT DOCUMENTS

| | | | |
|---|---|---|---|
| 1,376,652 A | 5/1921 | Steedman |
| 1,380,272 A | 5/1921 | Tomasulo |
| 1,430,015 A | 9/1922 | Icher |
| 1,437,941 A | 12/1922 | Hoover |
| 1,442,697 A | 1/1923 | Orthmann |
| 1,443,360 A | 1/1923 | Grace |
| 1,445,198 A | 2/1923 | Bornmann |
| 1,450,391 A | 4/1923 | Shaw |
| 1,653,819 A | 12/1927 | Ephraim |
| 3,437,941 A | 4/1969 | Leary |
| 3,634,460 A | 1/1972 | Nelson |
| 3,639,545 A | 2/1972 | Wilcox |
| 3,730,238 A | 5/1973 | Butler |
| 3,746,004 A | 7/1973 | Jankelson |
| 3,871,359 A | 3/1975 | Pacela |
| 4,016,866 A | 4/1977 | Lawton |
| 4,016,886 A | 4/1977 | Doss et al. |
| 4,037,341 A | 7/1977 | Odle |
| 4,216,860 A | 8/1980 | Heimann |
| 4,224,949 A | 9/1980 | Scott |
| 4,226,246 A | 10/1980 | Fragnet |
| 4,262,672 A | 4/1981 | Kief |
| 4,267,047 A | 5/1981 | Henne |
| 4,278,092 A | 7/1981 | Borsanyi et al. |
| 4,299,217 A | 11/1981 | Sagae et al. |
| 4,304,239 A | 12/1981 | Perlin |
| 4,311,148 A | 1/1982 | Courtney |
| 4,336,881 A | 6/1982 | Babb et al. |
| 4,344,436 A | 8/1982 | Kubota |
| 4,392,855 A | 7/1983 | Oreopoulos |
| 4,406,827 A | 9/1983 | Carim |
| 4,407,943 A | 10/1983 | Cole |
| 4,416,276 A | 11/1983 | Newton et al. |
| 4,447,235 A | 5/1984 | Clarke |
| 4,469,098 A | 9/1984 | Davi |
| 4,489,535 A | 12/1984 | Veltman |
| 4,512,765 A | 4/1985 | Muto |
| 4,580,572 A | 4/1986 | Granek et al. |
| 4,636,199 A | 1/1987 | Victor |
| 4,672,969 A | 6/1987 | Dew |
| 4,676,258 A | 6/1987 | Inokuchi |
| 4,676,782 A | 6/1987 | Yamamoto et al. |
| 4,687,471 A | 8/1987 | Twardowski |
| 4,716,896 A | 1/1988 | Ackerman |
| 4,723,549 A | 2/1988 | Wholey |
| D294,519 S | 3/1988 | Hardy, Jr. |
| 4,756,838 A | 7/1988 | Veltman |
| 4,772,269 A | 9/1988 | Twardowski |
| 4,798,585 A | 1/1989 | Inoue |
| 4,810,963 A | 3/1989 | Blake-Coleman et al. |
| 4,813,929 A | 3/1989 | Semrad |
| 4,819,637 A | 4/1989 | Dormandy, Jr. |
| 4,822,470 A | 4/1989 | Chang |
| 4,836,204 A | 6/1989 | Landymore |
| 4,840,172 A | 6/1989 | Augustine |
| 4,863,426 A | 9/1989 | Ferragamo |
| 4,885,003 A | 12/1989 | Hillstead |
| 4,886,496 A | 12/1989 | Conoscenti |
| 4,886,502 A | 12/1989 | Poirier et al. |
| 4,889,634 A | 12/1989 | El-Rashidy |
| 4,903,707 A | 2/1990 | Knute |
| 4,907,601 A | 3/1990 | Frick |
| 4,919,148 A | 4/1990 | Muccio |
| 4,921,484 A | 4/1990 | Muccio |
| 4,920,978 A | 5/1990 | Colvin |
| 4,946,793 A | 8/1990 | Marshall, III |
| 4,976,709 A | 12/1990 | Sand |
| 4,981,477 A | 1/1991 | Schon |
| 4,986,810 A | 1/1991 | Semrad |
| 4,987,895 A | 1/1991 | Heimlich |
| 5,019,034 A | 5/1991 | Weaver et al. |
| 5,031,775 A | 7/1991 | Kane |
| 5,052,391 A | 10/1991 | Silberstone |
| 5,053,013 A | 10/1991 | Ensminger et al. |
| 5,058,605 A | 10/1991 | Slovak |
| 5,071,558 A | 12/1991 | Itob |
| 5,098,843 A | 3/1992 | Calvin |
| 5,122,137 A | 6/1992 | Lennox |
| 5,134,070 A | 7/1992 | Casnig |
| 5,137,517 A | 8/1992 | Loney |
| 5,141,499 A | 8/1992 | Zappacosta |
| D329,496 S | 9/1992 | Wotton |
| 5,156,597 A | 10/1992 | Verreet |
| 5,173,158 A | 12/1992 | Schmukler |
| 5,186,715 A | 2/1993 | Phillips |
| 5,186,800 A | 2/1993 | Dower |
| 5,188,592 A | 2/1993 | Hakki |
| 5,190,541 A | 3/1993 | Abele |
| 5,192,312 A | 3/1993 | Orton |
| 5,193,537 A | 3/1993 | Freeman |
| 5,209,723 A | 5/1993 | Twardowski et al. |
| 5,215,530 A | 6/1993 | Hogan |
| 5,222,997 A | 6/1993 | Montgomery |
| 5,224,933 A | 7/1993 | Bromander |
| 5,227,730 A | 7/1993 | King et al. |
| 5,242,415 A | 9/1993 | Kantrowitz et al. |
| 5,273,525 A | 12/1993 | Hofmann |
| D343,687 S | 1/1994 | Houghton, II |
| 5,277,201 A | 1/1994 | Stern |
| 5,279,564 A | 1/1994 | Taylor |
| 5,281,213 A | 1/1994 | Milder et al. |
| 5,283,194 A | 2/1994 | Schmukler |
| 5,290,263 A | 3/1994 | Wigness et al. |
| 5,308,325 A | 5/1994 | Quinn et al. |
| 5,308,338 A | 5/1994 | Helfrich |
| 5,318,543 A | 6/1994 | Ross |
| 5,318,563 A | 6/1994 | Malis et al. |
| 5,328,451 A | 7/1994 | Davis et al. |
| 5,334,167 A | 8/1994 | Cocanower |
| 5,348,554 A | 9/1994 | Imran |
| D351,661 S | 10/1994 | Fischer |
| 5,383,917 A | 1/1995 | Desai et al. |
| 5,389,069 A | 2/1995 | Weaver |
| 5,391,158 A | 2/1995 | Peters |
| 5,403,311 A | 4/1995 | Abele |
| 5,405,320 A | 4/1995 | Twardowski et al. |
| 5,417,687 A | 5/1995 | Nardella et al. |
| 5,424,752 A | 6/1995 | Yamazaki |
| 5,425,752 A | 6/1995 | Vu Nguyen |
| 5,439,440 A | 8/1995 | Hofmann |
| 5,439,444 A | 8/1995 | Andersen |
| 5,458,597 A | 10/1995 | Edwards |
| 5,458,625 A | 10/1995 | Kendall |
| 5,462,521 A | 10/1995 | Brucker et al. |
| 5,462,644 A | 10/1995 | Woodson |
| 5,484,400 A | 1/1996 | Edwards et al. |
| 5,484,401 A | 1/1996 | Rodriguez |
| 5,533,999 A | 7/1996 | Hood et al. |
| 5,536,240 A | 7/1996 | Edwards et al. |
| 5,536,267 A | 7/1996 | Edwards et al. |
| 5,540,737 A | 7/1996 | Fenn |
| 5,542,916 A | 8/1996 | Hirsch |
| 5,546,940 A | 8/1996 | Panescu et al. |
| 5,562,720 A | 10/1996 | Stern et al. |
| 5,575,811 A | 11/1996 | Reid et al. |
| D376,652 S | 12/1996 | Hunt |
| 5,582,588 A | 12/1996 | Sakurai et al. |
| 5,586,982 A | 12/1996 | Abela |
| 5,588,424 A | 12/1996 | Insler |
| 5,588,960 A | 12/1996 | Edwards et al. |

(56) References Cited

U.S. PATENT DOCUMENTS

| | | |
|---|---|---|
| 5,599,294 A | 2/1997 | Edwards et al. |
| 5,599,311 A | 2/1997 | Raulerson |
| 5,616,126 A | 4/1997 | Malekmehr |
| 5,620,479 A | 4/1997 | Diederich |
| 5,626,146 A | 5/1997 | Barber et al. |
| 5,630,426 A | 5/1997 | Eggers et al. |
| D380,272 S | 6/1997 | Partika |
| 5,634,899 A | 6/1997 | Shapland et al. |
| 5,643,197 A | 7/1997 | Brucker et al. |
| 5,645,855 A | 7/1997 | Lorenz |
| 5,653,684 A | 8/1997 | Laptewicz |
| 5,672,173 A | 9/1997 | Gough et al. |
| 5,672,174 A | 9/1997 | Gough et al. |
| 5,674,267 A | 10/1997 | Mir |
| 5,681,282 A | 10/1997 | Eggers |
| 5,683,384 A | 11/1997 | Gough et al. |
| 5,687,723 A | 11/1997 | Avitall |
| 5,690,620 A | 11/1997 | Knott |
| 5,697,905 A | 12/1997 | D Ambrosio |
| 5,700,252 A | 12/1997 | Klingenstein |
| 5,702,359 A | 12/1997 | Hofmann |
| 5,707,332 A | 1/1998 | Weinberger |
| 5,718,246 A | 2/1998 | Vona |
| 5,720,921 A | 2/1998 | Meserol |
| 5,728,143 A | 3/1998 | Gough et al. |
| 5,735,847 A | 4/1998 | Gough et al. |
| 5,749,914 A | 5/1998 | Janssen |
| 5,752,939 A | 5/1998 | Makoto |
| 5,778,894 A | 7/1998 | Dorogi |
| 5,782,827 A | 7/1998 | Gough et al. |
| 5,782,882 A | 7/1998 | Lerman |
| 5,800,378 A | 9/1998 | Edwards et al. |
| 5,800,484 A | 9/1998 | Gough et al. |
| 5,807,272 A | 9/1998 | Kun et al. |
| 5,807,306 A | 9/1998 | Shapland |
| 5,807,395 A | 9/1998 | Mulier et al. |
| 5,810,742 A | 9/1998 | Pearlman |
| 5,810,762 A | 9/1998 | Hofmann |
| 5,810,804 A | 9/1998 | Gough et al. |
| 5,830,184 A | 11/1998 | Basta |
| 5,836,897 A | 11/1998 | Sakurai et al. |
| 5,836,905 A | 11/1998 | Lemelson et al. |
| 5,843,026 A | 12/1998 | Edwards et al. |
| 5,843,182 A | 12/1998 | Goldstein |
| 5,856,081 A | 1/1999 | Fahy |
| 5,863,290 A | 1/1999 | Gough et al. |
| 5,865,787 A | 2/1999 | Shapland et al. |
| 5,866,756 A | 2/1999 | Giros et al. |
| 5,868,708 A | 2/1999 | Hart |
| 5,873,849 A | 2/1999 | Bernard |
| 5,873,877 A | 2/1999 | McGaffigan |
| 5,904,648 A | 5/1999 | Arndt et al. |
| 5,913,855 A | 6/1999 | Gough et al. |
| 5,919,142 A | 7/1999 | Boone |
| 5,919,191 A | 7/1999 | Lennox et al. |
| 5,921,982 A | 7/1999 | Lesh et al. |
| 5,944,710 A | 8/1999 | Dev et al. |
| 5,947,284 A | 9/1999 | Foster |
| 5,947,889 A | 9/1999 | Hehrlein |
| 5,951,546 A | 9/1999 | Lorentzen |
| 5,954,745 A | 9/1999 | Gertler |
| 5,957,919 A | 9/1999 | Laufer |
| 5,957,963 A | 9/1999 | Dobak, III |
| 5,968,006 A | 10/1999 | Hofmann |
| 5,983,131 A | 11/1999 | Weaver |
| 5,983,140 A | 11/1999 | Smith |
| 5,984,896 A | 11/1999 | Boyd |
| 5,991,697 A | 11/1999 | Nelson et al. |
| 5,993,466 A | 11/1999 | Yoon |
| 5,999,847 A | 12/1999 | Elstrom |
| 6,004,339 A | 12/1999 | Wijay |
| 6,009,347 A | 12/1999 | Hofmann |
| 6,009,647 A | 1/2000 | Feingold |
| 6,009,877 A | 1/2000 | Edwards |
| 6,010,452 A | 1/2000 | Harcourt |
| 6,010,613 A | 1/2000 | Walters et al. |
| 6,010,616 A | 1/2000 | Lewis |
| 6,012,885 A | 1/2000 | Taylor |
| 6,016,452 A | 1/2000 | Kasevich |
| 6,023,638 A | 2/2000 | Swanson |
| 6,029,090 A | 2/2000 | Herbst |
| 6,033,402 A | 3/2000 | Tu |
| 6,041,252 A | 3/2000 | Walker et al. |
| 6,043,066 A | 3/2000 | Mangano et al. |
| 6,050,994 A | 4/2000 | Sherman |
| 6,055,453 A | 4/2000 | Hofmann et al. |
| 6,055,456 A | 4/2000 | Gerber |
| 6,059,780 A | 5/2000 | Gough et al. |
| 6,066,134 A | 5/2000 | Eggers et al. |
| 6,068,121 A | 5/2000 | McGlinch |
| 6,068,650 A | 5/2000 | Hofmann et al. |
| 6,071,281 A | 6/2000 | Burnside et al. |
| 6,074,374 A | 6/2000 | Fulton |
| 6,074,389 A | 6/2000 | Levine et al. |
| 6,085,115 A | 7/2000 | Weaver et al. |
| 6,090,016 A | 7/2000 | Kuo |
| 6,090,105 A | 7/2000 | Zepeda et al. |
| 6,090,106 A | 7/2000 | Goble |
| D430,015 S | 8/2000 | Himbert |
| 6,096,035 A | 8/2000 | Sodhi |
| 6,102,885 A | 8/2000 | Bass |
| 6,106,521 A | 8/2000 | Blewett et al. |
| 6,106,524 A | 8/2000 | Eggers et al. |
| 6,109,270 A | 8/2000 | Mah et al. |
| 6,110,192 A | 8/2000 | Ravenscroft et al. |
| 6,113,593 A | 9/2000 | Tu et al. |
| 6,116,330 A | 9/2000 | Salyer |
| 6,120,493 A | 9/2000 | Hofmann |
| 6,122,599 A | 9/2000 | Mehta |
| 6,123,701 A | 9/2000 | Nezhat |
| 6,132,397 A | 10/2000 | Davis et al. |
| 6,132,419 A | 10/2000 | Hofmann |
| 6,134,460 A | 10/2000 | Chance |
| 6,135,999 A | 10/2000 | Fanton |
| 6,139,544 A | 10/2000 | Mikus |
| 6,139,545 A | 10/2000 | Utley et al. |
| 6,142,992 A * | 11/2000 | Cheng ............. A61B 18/1206 606/34 |
| 6,150,148 A | 11/2000 | Nanda |
| 6,152,923 A | 11/2000 | Ryan |
| 6,159,163 A | 12/2000 | Strauss et al. |
| 6,178,354 B1 | 1/2001 | Gibson |
| D437,941 S | 2/2001 | Frattini |
| 6,193,715 B1 | 2/2001 | Wrublewski et al. |
| 6,198,970 B1 | 3/2001 | Freed et al. |
| 6,200,314 B1 | 3/2001 | Sherman |
| 6,208,893 B1 | 3/2001 | Hofmann |
| 6,210,402 B1 | 4/2001 | Olsen |
| 6,212,433 B1 | 4/2001 | Behl |
| 6,216,034 B1 | 4/2001 | Hofmann et al. |
| 6,219,577 B1 | 4/2001 | Brown, III |
| D442,697 S | 5/2001 | Hajianpour |
| 6,233,490 B1 | 5/2001 | Kasevich |
| 6,235,023 B1 | 5/2001 | Lee et al. |
| D443,360 S | 6/2001 | Haberland |
| 6,241,702 B1 | 6/2001 | Lundquist et al. |
| 6,241,725 B1 | 6/2001 | Cosman |
| D445,198 S | 7/2001 | Frattini |
| 6,258,100 B1 | 7/2001 | Alferness |
| 6,258,249 B1 | 7/2001 | Simpson |
| 6,261,831 B1 | 7/2001 | Agee |
| 6,277,114 B1 | 8/2001 | Bullivant et al. |
| 6,278,895 B1 | 8/2001 | Bernard |
| 6,280,441 B1 | 8/2001 | Ryan |
| 6,283,988 B1 | 9/2001 | Laufer et al. |
| 6,283,989 B1 | 9/2001 | Laufer et al. |
| 6,284,140 B1 | 9/2001 | Sommermeyer |
| 6,287,293 B1 | 9/2001 | Jones et al. |
| 6,287,304 B1 | 9/2001 | Eggers et al. |
| 6,296,636 B1 | 10/2001 | Cheng et al. |
| 6,298,726 B1 | 10/2001 | Adachi et al. |
| 6,299,633 B1 | 10/2001 | Laufer |
| 6,300,108 B1 | 10/2001 | Rubinsky et al. |
| D450,391 S | 11/2001 | Hunt |

(56) References Cited

U.S. PATENT DOCUMENTS

| | | |
|---|---|---|
| 6,312,428 B1 | 11/2001 | Eggers |
| 6,326,177 B1 | 12/2001 | Schoenbach |
| 6,327,505 B1 | 12/2001 | Medhkour |
| 6,328,689 B1 | 12/2001 | Gonzalez et al. |
| 6,328,735 B1 | 12/2001 | Curley et al. |
| 6,330,478 B1 | 12/2001 | Lee et al. |
| 6,347,247 B1 | 2/2002 | Dev et al. |
| 6,349,233 B1 | 2/2002 | Adams |
| 6,351,674 B2 | 2/2002 | Silverstone |
| 6,375,634 B1 | 4/2002 | Carroll |
| 6,387,671 B1 | 5/2002 | Rubinsky et al. |
| 6,398,779 B1 | 6/2002 | Buysse |
| 6,403,347 B1 | 6/2002 | Bills |
| 6,403,348 B1 | 6/2002 | Rubinsky et al. |
| 6,405,732 B1 | 6/2002 | Edwards et al. |
| 6,411,852 B1 | 6/2002 | Danek |
| 6,419,674 B1 | 7/2002 | Bowser et al. |
| 6,428,802 B1 | 8/2002 | Atala |
| 6,437,551 B1 | 8/2002 | Krulevitch |
| 6,443,952 B1 | 9/2002 | Mulier et al. |
| 6,463,331 B1 | 10/2002 | Edwards |
| 6,470,211 B1 | 10/2002 | Ideker et al. |
| 6,478,793 B1 | 11/2002 | Cosman et al. |
| 6,482,221 B1 | 11/2002 | Hebert et al. |
| 6,482,619 B1 | 11/2002 | Rubinsky et al. |
| 6,485,487 B1 | 11/2002 | Sherman |
| 6,488,673 B1 | 12/2002 | Laufer et al. |
| 6,488,678 B2 | 12/2002 | Sherman |
| 6,488,680 B1 | 12/2002 | Francischelli et al. |
| 6,491,706 B1 | 12/2002 | Alferness |
| 6,493,569 B2 | 12/2002 | Foo |
| 6,493,589 B1 | 12/2002 | Medhkour |
| 6,493,592 B1 | 12/2002 | Leonard et al. |
| 6,497,704 B2 | 12/2002 | Ein-Gal |
| 6,500,173 B2 | 12/2002 | Underwood |
| 6,503,248 B1 | 1/2003 | Levine |
| 6,506,189 B1 | 1/2003 | Rittman, III et al. |
| 6,514,248 B1 | 2/2003 | Eggers et al. |
| 6,520,183 B2 | 2/2003 | Amar |
| 6,526,320 B2 | 2/2003 | Mitchell |
| D471,640 S | 3/2003 | McMichael |
| D471,641 S | 3/2003 | McMichael |
| 6,530,922 B2 | 3/2003 | Cosman et al. |
| 6,533,784 B2 | 3/2003 | Truckai |
| 6,537,976 B1 | 3/2003 | Gupta |
| 6,540,695 B1 | 4/2003 | Burbank |
| 6,558,378 B2 | 5/2003 | Sherman et al. |
| 6,562,604 B2 | 5/2003 | Rubinsky et al. |
| 6,569,162 B2 | 5/2003 | He |
| 6,575,967 B1 | 6/2003 | Leveen et al. |
| 6,575,969 B1 | 6/2003 | Rittman, III et al. |
| 6,589,161 B2 | 7/2003 | Corcoran |
| 6,589,174 B1 | 7/2003 | Chopra et al. |
| 6,592,594 B2 | 7/2003 | Rimbaugh |
| 6,607,529 B1 | 8/2003 | Jones et al. |
| 6,610,054 B1 | 8/2003 | Edwards et al. |
| 6,611,706 B2 | 8/2003 | Avrahami et al. |
| 6,613,211 B1 | 9/2003 | McCormick et al. |
| 6,616,657 B2 | 9/2003 | Simpson et al. |
| 6,627,421 B1 | 9/2003 | Unger et al. |
| D480,816 S | 10/2003 | McMichael |
| 6,634,363 B1 | 10/2003 | Danek et al. |
| 6,638,253 B2 | 10/2003 | Breznock |
| 6,638,275 B1 | 10/2003 | McGaffigan |
| 6,653,091 B1 | 11/2003 | Dunn et al. |
| 6,666,858 B2 | 12/2003 | Lafontaine |
| 6,669,691 B1 | 12/2003 | Taimisto |
| 6,673,070 B2 | 1/2004 | Edwards et al. |
| 6,678,558 B1 | 1/2004 | Dimmer et al. |
| 6,682,501 B1 | 1/2004 | Nelson et al. |
| 6,689,096 B1 | 2/2004 | Loubens et al. |
| 6,689,127 B1 | 2/2004 | Gough et al. |
| 6,692,493 B2 | 2/2004 | McGovern et al. |
| 6,694,170 B1 | 2/2004 | Mikus |
| 6,694,964 B2 | 2/2004 | Wu |
| 6,694,979 B2 | 2/2004 | Deem et al. |
| 6,694,984 B2 | 2/2004 | Habib |
| 6,695,861 B1 | 2/2004 | Rosenberg |
| 6,697,669 B2 | 2/2004 | Dev et al. |
| 6,697,670 B2 | 2/2004 | Chomenky |
| 6,702,808 B1 | 3/2004 | Kreindel |
| 6,712,811 B2 | 3/2004 | Underwood |
| D489,973 S | 5/2004 | Root |
| 6,733,516 B2 | 5/2004 | Simons |
| 6,753,171 B2 | 6/2004 | Karube et al. |
| 6,761,716 B2 | 7/2004 | Kadhiresan et al. |
| 6,770,070 B1 | 8/2004 | Balbierz |
| D495,807 S | 9/2004 | Agbodoe |
| 6,795,728 B2 | 9/2004 | Chornenky |
| 6,801,804 B2 | 10/2004 | Miller et al. |
| 6,812,204 B1 | 11/2004 | McHale et al. |
| 6,837,886 B2 | 1/2005 | Collins et al. |
| 6,847,848 B2 | 1/2005 | Sterzer et al. |
| 6,860,847 B2 | 3/2005 | Alferness |
| 6,865,416 B2 | 3/2005 | Dev et al. |
| 6,869,430 B2 | 3/2005 | Balbierz et al. |
| 6,881,213 B2 | 4/2005 | Ryan |
| 6,892,099 B2 | 5/2005 | Jaafar |
| 6,895,267 B2 | 5/2005 | Panescu |
| 6,905,480 B2 | 6/2005 | McGuckin, Jr. |
| 6,912,417 B1 | 6/2005 | Bernard |
| 6,926,713 B2 | 8/2005 | Rioux |
| 6,927,049 B2 | 8/2005 | Rubinsky et al. |
| 6,941,950 B2 | 9/2005 | Wilson |
| 6,942,681 B2 | 9/2005 | Johnson |
| 6,958,062 B1 | 10/2005 | Gough et al. |
| 6,960,189 B2 | 11/2005 | Bates |
| 6,962,587 B2 | 11/2005 | Johnson et al. |
| 6,972,013 B1 | 12/2005 | Zhang et al. |
| 6,972,014 B2 | 12/2005 | Eum |
| 6,989,010 B2 | 1/2006 | Francischelli et al. |
| 6,994,689 B1 | 2/2006 | Zadno-Azizi |
| 6,994,706 B2 | 2/2006 | Chornenky et al. |
| 7,008,421 B2 | 3/2006 | Daniel et al. |
| 7,011,094 B2 | 3/2006 | Rapacki |
| 7,012,061 B1 | 3/2006 | Reiss |
| 7,027,869 B2 | 4/2006 | Danek et al. |
| 7,036,510 B2 | 5/2006 | Zgoda |
| 7,053,063 B2 | 5/2006 | Rubinsky et al. |
| 7,054,665 B2 | 5/2006 | Turner |
| 7,054,685 B2 | 5/2006 | Dimmer et al. |
| 7,063,698 B2 | 6/2006 | Whayne et al. |
| 7,087,040 B2 | 8/2006 | McGuckin, Jr. |
| 7,097,612 B2 | 8/2006 | Bertolero |
| 7,100,616 B2 | 9/2006 | Springmeyer |
| 7,113,821 B1 | 9/2006 | Sun et al. |
| 7,130,697 B2 | 10/2006 | Chornenky |
| 7,162,303 B2 | 1/2007 | Levin et al. |
| 7,169,107 B2 | 1/2007 | Jersey-Willuhn et al. |
| 7,211,083 B2 | 5/2007 | Chornenky |
| 7,232,437 B2 | 6/2007 | Berman et al. |
| 7,250,048 B2 | 7/2007 | Francischelli et al. |
| D549,332 S | 8/2007 | Matsumoto |
| 7,257,450 B2 | 8/2007 | Auth |
| 7,264,002 B2 | 9/2007 | Danek et al. |
| 7,267,676 B2 | 9/2007 | Chornenky et al. |
| 7,273,055 B2 | 9/2007 | Danek et al. |
| 7,291,146 B2 | 11/2007 | Steinke et al. |
| 7,331,940 B2 | 2/2008 | Sommerich |
| 7,331,949 B2 | 2/2008 | Marisi |
| 7,341,558 B2 | 3/2008 | De La Torre |
| 7,344,533 B2 | 3/2008 | Pearson et al. |
| D565,743 S | 4/2008 | Phillips |
| D571,478 S | 6/2008 | Horacek |
| 7,387,626 B2 | 6/2008 | Edwards et al. |
| 7,399,747 B1 | 7/2008 | Clair |
| D575,399 S | 8/2008 | Matsumoto |
| D575,402 S | 8/2008 | Sandor |
| 7,412,977 B2 | 8/2008 | Fields et al. |
| 7,419,487 B2 | 9/2008 | Johnson et al. |
| 7,434,578 B2 | 10/2008 | Dillard |
| 7,437,194 B2 | 10/2008 | Skwarek |
| 7,449,019 B2 | 11/2008 | Uchida et al. |
| 7,451,765 B2 | 11/2008 | Adler |

(56) References Cited

U.S. PATENT DOCUMENTS

| | | |
|---|---|---|
| 7,455,675 B2 | 11/2008 | Schur |
| 7,476,203 B2 | 1/2009 | Devore |
| 7,488,292 B2 | 2/2009 | Adachi |
| 7,520,877 B2 | 4/2009 | Lee, Jr. et al. |
| 7,533,671 B2 | 5/2009 | Gonzalez |
| D595,422 S | 6/2009 | Mustapha |
| 7,544,301 B2 | 6/2009 | Shah et al. |
| 7,549,984 B2 | 6/2009 | Mathis |
| 7,553,309 B2 | 6/2009 | Buysse et al. |
| 7,565,208 B2 | 7/2009 | Harris et al. |
| 7,571,729 B2 | 8/2009 | Saadat |
| 7,617,005 B2 | 11/2009 | Demarais et al. |
| 7,620,451 B2 | 11/2009 | Demarais et al. |
| 7,620,507 B2 | 11/2009 | Richardson |
| 7,632,291 B2 | 12/2009 | Stephens |
| 7,647,115 B2 | 1/2010 | Levin et al. |
| 7,653,438 B2 | 1/2010 | Deem et al. |
| 7,655,004 B2 | 2/2010 | Long |
| 7,670,333 B2 | 3/2010 | Schatzberger |
| 7,674,249 B2 | 3/2010 | Ivorra et al. |
| 7,680,543 B2 | 3/2010 | Azure |
| D613,418 S | 4/2010 | Ryan |
| 7,699,842 B2 | 4/2010 | Buysse et al. |
| 7,706,865 B1 | 4/2010 | Snell |
| 7,717,948 B2 | 5/2010 | Demarais et al. |
| 7,718,409 B2 | 5/2010 | Rubinsky et al. |
| 7,722,606 B2 | 5/2010 | Azure |
| 7,742,795 B2 | 6/2010 | Stone et al. |
| 7,763,018 B2 | 7/2010 | DeCarlo et al. |
| 7,765,010 B2 | 7/2010 | Chornenky et al. |
| 7,771,401 B2 | 8/2010 | Hekmat et al. |
| 7,776,035 B2 | 8/2010 | Rick et al. |
| 7,815,571 B2 | 10/2010 | Deckman |
| 7,815,662 B2 | 10/2010 | Spivey |
| 7,824,870 B2 | 11/2010 | Kovalcheck |
| RE42,016 E | 12/2010 | Chornenky et al. |
| 7,846,108 B2 | 12/2010 | Turovskiy et al. |
| 7,853,333 B2 | 12/2010 | Demarais |
| D630,321 S | 1/2011 | Hamilton, Jr. |
| D631,154 S | 1/2011 | Hamilton, Jr. |
| 7,874,986 B2 | 1/2011 | Deckman et al. |
| 7,875,025 B2 | 1/2011 | Cockburn et al. |
| 7,879,031 B2 | 2/2011 | Peterson |
| RE42,277 E | 4/2011 | Jaafar et al. |
| 7,918,852 B2 | 4/2011 | Tullis |
| 7,937,143 B2 | 5/2011 | Demarais et al. |
| 7,938,824 B2 | 5/2011 | Chornenky et al. |
| 7,951,582 B2 | 5/2011 | Gazit et al. |
| 7,955,827 B2 | 6/2011 | Rubinsky et al. |
| RE42,835 E | 10/2011 | Chornenky et al. |
| D647,628 S | 10/2011 | Helfteren |
| 8,029,504 B2 | 10/2011 | Long |
| 8,037,591 B2 | 10/2011 | Spivey et al. |
| 8,048,067 B2 | 11/2011 | Davalos et al. |
| 8,052,604 B2 | 11/2011 | Lau et al. |
| 8,057,391 B2 | 11/2011 | Lau et al. |
| 8,062,290 B2 | 11/2011 | Buysse et al. |
| RE43,009 E | 12/2011 | Chornenky et al. |
| 8,070,759 B2 | 12/2011 | Stefanchik et al. |
| 8,075,572 B2 | 12/2011 | Stefanchik |
| 8,088,072 B2 | 1/2012 | Munrow |
| 8,100,922 B2 | 1/2012 | Griffith |
| 8,109,926 B2 | 2/2012 | Azure |
| 8,114,070 B2 | 2/2012 | Rubinsky et al. |
| 8,114,072 B2 | 2/2012 | Long et al. |
| 8,114,119 B2 | 2/2012 | Spivey et al. |
| 8,131,371 B2 | 3/2012 | Demarals et al. |
| 8,131,372 B2 | 3/2012 | Levin et al. |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,154,288 B2 | 4/2012 | Deimling |
| 8,157,834 B2 | 4/2012 | Conlon |
| 8,162,918 B2 | 4/2012 | Ivorra et al. |
| 8,172,772 B2 | 5/2012 | Zwolinski |
| 8,174,267 B2 | 5/2012 | Brannan et al. |
| 8,175,711 B2 | 5/2012 | Demarais et al. |
| 8,180,433 B2 | 5/2012 | Brannan et al. |
| 8,181,995 B2 | 5/2012 | DeCarlo |
| 8,182,477 B2 | 5/2012 | Orszulak et al. |
| 8,187,269 B2 | 5/2012 | Shadduck |
| 8,187,270 B2 | 5/2012 | Auth et al. |
| 8,206,300 B2 | 6/2012 | Deckman |
| 8,211,097 B2 | 7/2012 | Leyh |
| 8,211,099 B2 | 7/2012 | Buysse et al. |
| 8,211,125 B2 | 7/2012 | Spivey |
| 8,216,161 B2 | 7/2012 | Darlington |
| 8,221,411 B2 | 7/2012 | Francischelli et al. |
| 8,231,603 B2 | 7/2012 | Hobbs et al. |
| 8,240,468 B2 | 8/2012 | Wilkinson |
| 8,241,204 B2 | 8/2012 | Spivey |
| 8,242,782 B2 | 8/2012 | Brannan et al. |
| 8,246,615 B2 | 8/2012 | Behnke |
| 8,248,075 B2 | 8/2012 | Brannan et al. |
| 8,251,986 B2 | 8/2012 | Chornenky et al. |
| 8,252,057 B2 | 8/2012 | Fox |
| 8,262,563 B2 | 9/2012 | Bakos et al. |
| 8,262,577 B2 | 9/2012 | Munrow |
| 8,262,655 B2 | 9/2012 | Ghabrial et al. |
| 8,262,680 B2 | 9/2012 | Swain |
| 8,267,884 B1 | 9/2012 | Hicks |
| 8,267,927 B2 | 9/2012 | Dalal |
| 8,267,936 B2 | 9/2012 | Hushka |
| 8,277,379 B2 | 10/2012 | Lau et al. |
| 8,282,631 B2 | 10/2012 | Davalos et al. |
| 8,287,527 B2 | 10/2012 | Brannan et al. |
| 8,292,880 B2 | 10/2012 | Prakash et al. |
| 8,298,222 B2 | 10/2012 | Rubinsky et al. |
| 8,303,516 B2 | 11/2012 | Schmitz et al. |
| 8,317,806 B2 | 11/2012 | Coe |
| 8,337,394 B2 | 12/2012 | Vakharia |
| 8,343,144 B2 | 1/2013 | Kleyman |
| 8,346,370 B2 | 1/2013 | Haley et al. |
| 8,347,891 B2 | 1/2013 | Demarais et al. |
| 8,348,921 B2 | 1/2013 | Ivorra et al. |
| 8,348,938 B2 | 1/2013 | Blomgren et al. |
| 8,353,487 B2 | 1/2013 | Trusty |
| 8,353,902 B2 | 1/2013 | Prakash |
| 8,361,006 B2 | 1/2013 | Kraemer |
| 8,361,066 B2 | 1/2013 | Long et al. |
| 8,361,112 B2 | 1/2013 | Carroll, II |
| 8,366,712 B2 | 2/2013 | Bleich |
| 8,377,057 B2 | 2/2013 | Rick et al. |
| 8,380,283 B2 | 2/2013 | Krieg |
| D677,798 S | 3/2013 | Hart |
| 8,394,092 B2 | 3/2013 | Brannan |
| 8,394,102 B2 | 3/2013 | Garabedian |
| 8,398,626 B2 | 3/2013 | Buysse et al. |
| 8,398,641 B2 | 3/2013 | Wallace |
| 8,403,924 B2 | 3/2013 | Behnke et al. |
| 8,403,926 B2 | 3/2013 | Nobis |
| 8,409,200 B2 | 4/2013 | Holcomb et al. |
| 8,409,206 B2 | 4/2013 | Wallace |
| 8,417,328 B2 | 4/2013 | Sarfaty et al. |
| 8,425,455 B2 | 4/2013 | Nentwick |
| 8,425,505 B2 | 4/2013 | Long |
| 8,433,423 B2 | 4/2013 | Demarais |
| 8,437,845 B2 | 5/2013 | Sarfaty et al. |
| 8,439,907 B2 | 5/2013 | Auth et al. |
| 8,444,640 B2 | 5/2013 | Demarais et al. |
| 8,449,538 B2 | 5/2013 | Long |
| 8,454,594 B2 | 6/2013 | Demarais et al. |
| 8,465,464 B2 | 6/2013 | Travis |
| 8,465,484 B2 | 6/2013 | Davalos et al. |
| 8,469,716 B2 | 6/2013 | Fedotov et al. |
| 8,473,067 B2 | 6/2013 | Hastings et al. |
| 8,480,657 B2 | 7/2013 | Bakos |
| 8,480,665 B2 | 7/2013 | DeCarlo |
| 8,480,666 B2 | 7/2013 | Buysse et al. |
| 8,480,689 B2 | 7/2013 | Spivey et al. |
| 8,489,192 B1 | 7/2013 | Hlavka et al. |
| 8,496,574 B2 | 7/2013 | Trusty |

(56) References Cited

U.S. PATENT DOCUMENTS

| | | |
|---|---|---|
| 8,506,485 B2 | 8/2013 | Deckman et al. |
| 8,506,564 B2 | 8/2013 | Long et al. |
| 8,511,317 B2 | 8/2013 | Thapliyal et al. |
| 8,512,329 B2 | 8/2013 | Paulus |
| 8,512,330 B2 | 8/2013 | Epstein et al. |
| 8,518,031 B2 | 8/2013 | Boyden et al. |
| 8,529,563 B2 | 9/2013 | Long et al. |
| 8,542,019 B2 | 9/2013 | Brannan et al. |
| 8,546,979 B2 | 10/2013 | Heeren et al. |
| 8,548,600 B2 | 10/2013 | Deem et al. |
| 8,551,069 B2 | 10/2013 | Demarais et al. |
| 8,551,088 B2 | 10/2013 | Falkenstein et al. |
| 8,551,097 B2 | 10/2013 | Schmitz |
| 8,562,588 B2 | 10/2013 | Hobbs et al. |
| 8,562,598 B2 | 10/2013 | Falkenstein et al. |
| 8,562,599 B2 | 10/2013 | Leyh |
| 8,562,602 B2 | 10/2013 | Azure |
| 8,568,401 B2 | 10/2013 | Brannan |
| 8,568,402 B2 | 10/2013 | Buysse et al. |
| 8,568,404 B2 | 10/2013 | Brannan |
| 8,568,410 B2 | 10/2013 | Vakharia et al. |
| 8,568,411 B2 | 10/2013 | Falkenstein et al. |
| 8,579,894 B2 | 11/2013 | Falkenstein et al. |
| 8,579,897 B2 | 11/2013 | Vakharia et al. |
| 8,579,902 B2 | 11/2013 | Bleich et al. |
| 8,585,704 B2 | 11/2013 | Schmitz et al. |
| 8,603,087 B2 | 12/2013 | Rubinsky et al. |
| 8,608,652 B2 | 12/2013 | Voegele et al. |
| 8,608,739 B2 | 12/2013 | Sartor |
| 8,613,745 B2 | 12/2013 | Bleich |
| 8,617,163 B2 | 12/2013 | Bleich |
| 8,620,423 B2 | 12/2013 | Demarais et al. |
| 8,626,300 B2 | 1/2014 | Demarais et al. |
| 8,632,534 B2 | 1/2014 | Pearson |
| 8,634,929 B2 | 1/2014 | Chornenky et al. |
| 8,647,338 B2 | 2/2014 | Chornenky et al. |
| 8,647,346 B2 | 2/2014 | Bleich et al. |
| 8,652,130 B2 | 2/2014 | Kreindel |
| 8,652,138 B2 | 2/2014 | Bleich et al. |
| 8,652,150 B2 | 2/2014 | Swain et al. |
| 8,663,210 B2 | 3/2014 | Tomasello |
| 8,663,228 B2 | 3/2014 | Schmitz |
| 8,668,688 B2 | 3/2014 | Rusin |
| 8,672,937 B2 | 3/2014 | DeCarlo et al. |
| 8,679,003 B2 | 3/2014 | Spivey |
| 8,684,998 B2 | 4/2014 | Demarais et al. |
| 8,702,697 B2 | 4/2014 | Curley |
| 8,706,258 B2 | 4/2014 | Nabors, Sr. et al. |
| 8,712,500 B2 | 4/2014 | Schmidt et al. |
| 8,715,276 B2 | 5/2014 | Thompson |
| 8,721,637 B2 | 5/2014 | Zarins et al. |
| 8,725,249 B2 | 5/2014 | Bar-Yoseph |
| 8,728,137 B2 | 5/2014 | Zarins et al. |
| 8,728,138 B2 | 5/2014 | Zarins et al. |
| 8,728,139 B2 | 5/2014 | Azure et al. |
| 8,731,672 B2 | 5/2014 | Hlavka et al. |
| 8,740,895 B2 | 6/2014 | Mayse et al. |
| 8,740,896 B2 | 6/2014 | Zarins et al. |
| 8,753,335 B2 | 6/2014 | Moshe et al. |
| 8,768,470 B2 | 7/2014 | Deem et al. |
| 8,771,252 B2 | 7/2014 | Gelfand |
| 8,771,260 B2 | 7/2014 | Conlon et al. |
| 8,774,913 B2 | 7/2014 | Demarais et al. |
| 8,774,922 B2 | 7/2014 | Zarins et al. |
| 8,777,943 B2 | 7/2014 | Mayse et al. |
| 8,784,463 B2 | 7/2014 | Zarins et al. |
| 8,797,039 B2 | 8/2014 | Brannan |
| 8,801,626 B2 | 8/2014 | Sun et al. |
| 8,805,545 B2 | 8/2014 | Zarins |
| 8,808,280 B2 | 8/2014 | Mayse et al. |
| 8,814,860 B2 | 8/2014 | Davalos et al. |
| 8,818,514 B2 | 8/2014 | Zarins et al. |
| 8,821,489 B2 | 9/2014 | Mayse |
| 8,828,031 B2 | 9/2014 | Fox |
| 8,835,166 B2 | 9/2014 | Phillips |
| 8,845,559 B2 | 9/2014 | Darlington |
| 8,845,629 B2 | 9/2014 | Demarais |
| 8,845,635 B2 | 9/2014 | Daniel |
| 8,845,639 B2 | 9/2014 | Wallace |
| 8,852,163 B2 | 10/2014 | Deem |
| 8,858,550 B2 | 10/2014 | Busch-Madsen |
| 8,865,076 B2 | 10/2014 | Sarfaty |
| 8,880,185 B2 | 11/2014 | Hastings |
| 8,880,186 B2 | 11/2014 | Levin |
| 8,880,195 B2 | 11/2014 | Azure |
| 8,882,759 B2 | 11/2014 | Manley |
| 8,888,792 B2 | 11/2014 | Harris |
| 8,894,641 B2 | 11/2014 | Brannan |
| 8,903,488 B2 | 12/2014 | Callas |
| 8,906,006 B2 | 12/2014 | Chornenky |
| 8,906,011 B2 | 12/2014 | Gelbart |
| 8,906,035 B2 | 12/2014 | Zwolinski |
| 8,911,439 B2 | 12/2014 | Mayse |
| 8,915,910 B2 | 12/2014 | Falkenstein |
| 8,915,911 B2 | 12/2014 | Azure |
| 8,920,411 B2 | 12/2014 | Gelbart |
| 8,923,970 B2 | 12/2014 | Bar-Yoseph |
| 8,926,606 B2 | 1/2015 | Davalos |
| 8,932,287 B2 | 1/2015 | Gelbart |
| 8,932,289 B2 | 1/2015 | Mayse |
| 8,934,978 B2 | 1/2015 | Deem |
| 8,939,897 B2 | 1/2015 | Nobis |
| 8,939,970 B2 | 1/2015 | Stone |
| 8,945,121 B2 | 2/2015 | Curley |
| 8,948,865 B2 | 2/2015 | Zarins |
| 8,956,350 B2 | 2/2015 | Buysse |
| 8,958,871 B2 | 2/2015 | Demarais |
| 8,958,888 B2 | 2/2015 | Chornenky |
| 8,961,507 B2 | 2/2015 | Mayse |
| 8,961,508 B2 | 2/2015 | Mayse |
| 8,968,542 B2 | 3/2015 | Davalos |
| 8,974,451 B2 | 3/2015 | Smith |
| 8,983,595 B2 | 3/2015 | Levin |
| 8,986,294 B2 | 3/2015 | Demarais |
| 8,992,517 B2 | 3/2015 | Davalos |
| 9,005,189 B2 | 4/2015 | Davalos |
| 9,005,195 B2 | 4/2015 | Mayse |
| 9,005,198 B2 | 4/2015 | Long |
| 9,011,431 B2 | 4/2015 | Long |
| 9,017,323 B2 | 4/2015 | Miller |
| 9,017,324 B2 | 4/2015 | Mayse |
| 9,023,034 B2 | 5/2015 | Jenson |
| 9,023,037 B2 | 5/2015 | Zarins |
| 9,028,483 B2 | 5/2015 | Long |
| 9,028,485 B2 | 5/2015 | Edmunds |
| 9,039,702 B2 | 5/2015 | Miller |
| 9,049,987 B2 | 6/2015 | Conlon |
| 9,050,449 B2 | 6/2015 | Darlington |
| 9,060,761 B2 | 6/2015 | Hastings |
| 9,072,518 B2 | 7/2015 | Swanson |
| 9,072,527 B2 | 7/2015 | Deem |
| 9,078,665 B2 | 7/2015 | Moss |
| 9,084,609 B2 | 7/2015 | Smith |
| 9,089,350 B2 | 7/2015 | Willard |
| 9,101,386 B2 | 8/2015 | Wallace |
| 9,108,040 B2 | 8/2015 | Zarins |
| 9,113,888 B2 | 8/2015 | Orszulak |
| 9,119,633 B2 | 9/2015 | Gelbart |
| 9,119,634 B2 | 9/2015 | Gelbart |
| 9,125,643 B2 | 9/2015 | Hlavka |
| 9,125,661 B2 | 9/2015 | Deem |
| 9,125,666 B2 | 9/2015 | Steinke |
| 9,125,667 B2 | 9/2015 | Stone |
| 9,131,978 B2 | 9/2015 | Zarins |
| 9,138,281 B2 | 9/2015 | Zarins |
| 9,138,287 B2 | 9/2015 | Curley |
| 9,138,288 B2 | 9/2015 | Curley |
| 9,149,328 B2 | 10/2015 | Dimmer |
| 9,149,331 B2 | 10/2015 | Deem |
| 9,155,589 B2 | 10/2015 | Jenson |
| 9,173,704 B2 | 11/2015 | Hobbs |
| 9,186,198 B2 | 11/2015 | Demarais |
| 9,186,209 B2 | 11/2015 | Weber |
| 9,186,213 B2 | 11/2015 | Deem |

(56) References Cited

U.S. PATENT DOCUMENTS

| | | |
|---|---|---|
| 9,192,435 B2 | 11/2015 | Jenson |
| 9,192,715 B2 | 11/2015 | Gelfand |
| 9,192,790 B2 | 11/2015 | Hastings |
| 9,198,733 B2 | 12/2015 | Neal, II |
| 9,220,526 B2 | 12/2015 | Conlon |
| 9,220,558 B2 | 12/2015 | Willard |
| 9,220,561 B2 | 12/2015 | Crow |
| 9,226,772 B2 | 1/2016 | Fox |
| 9,226,790 B2 | 1/2016 | Zemel |
| 9,233,241 B2 | 1/2016 | Long |
| 9,247,952 B2 | 2/2016 | Bleich |
| 9,248,318 B2 | 2/2016 | Darlington |
| 9,254,169 B2 | 2/2016 | Long |
| 9,254,172 B2 | 2/2016 | Behnke, II |
| 9,265,557 B2 | 2/2016 | Sherman |
| 9,265,558 B2 | 2/2016 | Zarins |
| 9,276,367 B2 | 3/2016 | Brannan |
| 9,277,955 B2 | 3/2016 | Herscher |
| 9,277,969 B2 | 3/2016 | Brannan |
| 9,283,051 B2 | 3/2016 | Garcia |
| 9,289,255 B2 | 3/2016 | Deem |
| 9,295,516 B2 | 3/2016 | Pearson |
| 9,307,935 B2 | 4/2016 | Pluta |
| 9,308,039 B2 | 4/2016 | Azure |
| 9,308,043 B2 | 4/2016 | Zarins |
| 9,308,044 B2 | 4/2016 | Zarins |
| 9,314,620 B2 | 4/2016 | Long |
| 9,314,630 B2 | 4/2016 | Levin |
| 9,320,561 B2 | 4/2016 | Zarins |
| 9,320,563 B2 | 4/2016 | Brustad |
| 9,326,751 B2 | 5/2016 | Hastings |
| 9,326,817 B2 | 5/2016 | Zarins |
| 9,327,100 B2 | 5/2016 | Perry |
| 9,327,122 B2 | 5/2016 | Zarins |
| 9,339,618 B2 | 5/2016 | Deem |
| 9,351,790 B2 | 5/2016 | Zemel |
| 9,414,881 B2 | 8/2016 | Callas |
| 9,598,691 B2 | 3/2017 | Davalos |
| 9,700,368 B2 | 7/2017 | Callas |
| 9,764,145 B2 | 9/2017 | Callas |
| 9,867,652 B2 | 1/2018 | Sano |
| 9,943,599 B2 | 4/2018 | Gehl |
| 10,010,666 B2 | 7/2018 | Rubinsky |
| 10,117,701 B2 | 11/2018 | Davalos |
| 10,117,707 B2 | 11/2018 | Garcia |
| 10,143,512 B2 | 12/2018 | Rubinsky |
| 10,154,874 B2 | 12/2018 | Davalos |
| 10,238,447 B2 | 3/2019 | Neal, II |
| 10,245,098 B2 | 4/2019 | Davalos |
| 10,245,105 B2 | 4/2019 | Davalos |
| 10,272,178 B2 | 4/2019 | Davalos |
| 10,286,108 B2 | 5/2019 | Davalos |
| 10,292,755 B2 | 5/2019 | Arena |
| 10,342,600 B2 | 7/2019 | Callas |
| 10,448,989 B2 | 10/2019 | Arena |
| 10,470,822 B2 | 11/2019 | Garcia |
| 10,471,254 B2 | 11/2019 | Sano |
| 10,537,379 B2 | 1/2020 | Sano |
| 10,668,208 B2 | 6/2020 | Rubinsky |
| 10,694,972 B2 | 6/2020 | Davalos |
| 10,702,326 B2 | 7/2020 | Neal, II |
| 10,828,085 B2 | 11/2020 | Davalos |
| 10,828,086 B2 | 11/2020 | Davalos |
| 10,905,492 B2 | 2/2021 | Neal, II |
| 10,959,772 B2 | 3/2021 | Davalos |
| 11,254,926 B2 | 2/2022 | Garcia |
| 11,272,979 B2 | 3/2022 | Garcia |
| 11,311,329 B2 | 4/2022 | Davalos |
| 11,382,681 B2 | 7/2022 | Arena |
| 11,406,820 B2 | 8/2022 | Sano |
| 11,453,873 B2 | 9/2022 | Davalos |
| 11,607,271 B2 | 3/2023 | Garcia |
| 11,607,537 B2 | 3/2023 | Latouche |
| 11,638,603 B2 | 5/2023 | Sano |
| 11,655,466 B2 | 5/2023 | Neal, II |
| 11,723,710 B2 | 8/2023 | Neal, II |
| 11,737,810 B2 | 8/2023 | Davalos |
| 11,890,046 B2 | 2/2024 | Neal |
| 11,903,690 B2 | 2/2024 | Davalos |
| 2001/0014819 A1 | 8/2001 | Ingle |
| 2001/0039393 A1 | 11/2001 | Mori |
| 2001/0043706 A1 | 11/2001 | Masuda |
| 2001/0044596 A1 | 11/2001 | Jaafar |
| 2001/0046706 A1 | 11/2001 | Rubinsky et al. |
| 2001/0047167 A1 | 11/2001 | Heggeness |
| 2001/0051366 A1 | 12/2001 | Rubinsky et al. |
| 2002/0002393 A1 | 1/2002 | Mitchell |
| 2002/0010491 A1 | 1/2002 | Schoenbach et al. |
| 2002/0022864 A1 | 2/2002 | Mahvi et al. |
| 2002/0040204 A1 | 4/2002 | Dev et al. |
| 2002/0049370 A1 | 4/2002 | Laufer et al. |
| 2002/0052601 A1 | 5/2002 | Goldberg et al. |
| 2002/0055731 A1 | 5/2002 | Atala et al. |
| 2002/0065541 A1 | 5/2002 | Fredricks et al. |
| 2002/0072742 A1 | 6/2002 | Schaefer et al. |
| 2002/0077314 A1 | 6/2002 | Falk et al. |
| 2002/0077627 A1 | 6/2002 | Johnson et al. |
| 2002/0077676 A1 | 6/2002 | Schroeppel et al. |
| 2002/0082543 A1 | 6/2002 | Park et al. |
| 2002/0091362 A1 | 7/2002 | Maginot |
| 2002/0095197 A1 | 7/2002 | Lardo et al. |
| 2002/0099323 A1 | 7/2002 | Dev et al. |
| 2002/0104318 A1 | 8/2002 | Jaafar |
| 2002/0111615 A1 | 8/2002 | Cosman et al. |
| 2002/0112729 A1 | 8/2002 | Devore |
| 2002/0115208 A1 | 8/2002 | Mitchell |
| 2002/0119437 A1 | 8/2002 | Grooms |
| 2002/0120261 A1 | 8/2002 | Morris |
| 2002/0133324 A1 | 9/2002 | Weaver |
| 2002/0137121 A1 | 9/2002 | Rubinsky et al. |
| 2002/0138075 A1 | 9/2002 | Edwards et al. |
| 2002/0138117 A1 | 9/2002 | Son |
| 2002/0143365 A1 | 10/2002 | Herbst |
| 2002/0147462 A1 | 10/2002 | Mair et al. |
| 2002/0156472 A1 | 10/2002 | Lee et al. |
| 2002/0161361 A1 | 10/2002 | Sherman et al. |
| 2002/0183684 A1 | 12/2002 | Dev et al. |
| 2002/0183735 A1 | 12/2002 | Edwards |
| 2002/0183740 A1 | 12/2002 | Edwards et al. |
| 2002/0188242 A1 | 12/2002 | Wu |
| 2002/0193784 A1 | 12/2002 | McHale et al. |
| 2002/0193831 A1 | 12/2002 | Smith |
| 2003/0009110 A1 | 1/2003 | Tu et al. |
| 2003/0009165 A1 | 1/2003 | Edwards |
| 2003/0014047 A1 | 1/2003 | Woloszko et al. |
| 2003/0016168 A1 | 1/2003 | Jandrell |
| 2003/0055220 A1 | 3/2003 | Legrain |
| 2003/0055420 A1 | 3/2003 | Kadhiresan et al. |
| 2003/0059945 A1 | 3/2003 | Dzekunov et al. |
| 2003/0060856 A1 | 3/2003 | Chornenky et al. |
| 2003/0074039 A1 | 4/2003 | Puskas |
| 2003/0078490 A1 | 4/2003 | Damasco et al. |
| 2003/0088189 A1 | 5/2003 | Tu et al. |
| 2003/0088199 A1 | 5/2003 | Kawaji |
| 2003/0096407 A1 | 5/2003 | Atala et al. |
| 2003/0105454 A1 | 6/2003 | Cucin |
| 2003/0109871 A1 | 6/2003 | Johnson et al. |
| 2003/0127090 A1 | 7/2003 | Gifford et al. |
| 2003/0130711 A1 | 7/2003 | Pearson et al. |
| 2003/0135242 A1 | 7/2003 | Mongeon et al. |
| 2003/0149451 A1 | 8/2003 | Chomenky |
| 2003/0153960 A1 | 8/2003 | Chornenky |
| 2003/0154988 A1 | 8/2003 | Devore |
| 2003/0159700 A1 | 8/2003 | Laufer et al. |
| 2003/0164168 A1 | 9/2003 | Shaw |
| 2003/0166181 A1 | 9/2003 | Rubinsky et al. |
| 2003/0170898 A1 | 9/2003 | Gundersen et al. |
| 2003/0194808 A1 | 10/2003 | Rubinsky et al. |
| 2003/0195385 A1 | 10/2003 | Devore |
| 2003/0195406 A1 | 10/2003 | Jenkins |
| 2003/0199050 A1 | 10/2003 | Mangano et al. |
| 2003/0208200 A1 | 11/2003 | Palanker |
| 2003/0208236 A1 | 11/2003 | Heil |
| 2003/0212394 A1 | 11/2003 | Pearson et al. |

(56) References Cited

U.S. PATENT DOCUMENTS

| | | |
|---|---|---|
| 2003/0212412 A1 | 11/2003 | Dillard |
| 2003/0225360 A1 | 12/2003 | Eppstein et al. |
| 2003/0228344 A1 | 12/2003 | Fields et al. |
| 2003/0233091 A1 | 12/2003 | Whayne |
| 2004/0009459 A1 | 1/2004 | Anderson et al. |
| 2004/0019371 A1 | 1/2004 | Jaafar |
| 2004/0055606 A1 | 3/2004 | Hendricksen |
| 2004/0059328 A1 | 3/2004 | Daniel et al. |
| 2004/0059389 A1 | 3/2004 | Chornenky |
| 2004/0068228 A1 | 4/2004 | Cunningham |
| 2004/0116935 A1 | 6/2004 | Lechot |
| 2004/0116965 A1 | 6/2004 | Falkenberg |
| 2004/0133194 A1 | 7/2004 | Eum |
| 2004/0138715 A1 | 7/2004 | van Groeningen et al. |
| 2004/0146877 A1 | 7/2004 | Diss et al. |
| 2004/0153057 A1 | 8/2004 | Davison |
| 2004/0167458 A1 | 8/2004 | Draghia-Akli et al. |
| 2004/0172136 A1 | 9/2004 | Ralph |
| 2004/0176855 A1 | 9/2004 | Badylak |
| 2004/0187875 A1 | 9/2004 | He |
| 2004/0193042 A1 | 9/2004 | Scampini |
| 2004/0193097 A1 | 9/2004 | Hofmann |
| 2004/0199159 A1 | 10/2004 | Lee |
| 2004/0200484 A1 | 10/2004 | Springmeyer |
| 2004/0206349 A1 | 10/2004 | Alferness |
| 2004/0210248 A1 | 10/2004 | Gordon |
| 2004/0230187 A1 | 11/2004 | Lee et al. |
| 2004/0236376 A1 | 11/2004 | Miklavcic |
| 2004/0237340 A1 | 12/2004 | Rembrandt |
| 2004/0243107 A1 | 12/2004 | Macoviak |
| 2004/0267189 A1 | 12/2004 | Mavor et al. |
| 2004/0267256 A1 | 12/2004 | Garabedian |
| 2004/0267340 A1 | 12/2004 | Cioanta et al. |
| 2005/0004507 A1 | 1/2005 | Schroeppel |
| 2005/0004567 A1 | 1/2005 | Daniel |
| 2005/0010209 A1 | 1/2005 | Lee, Jr. et al. |
| 2005/0010259 A1 | 1/2005 | Gerber |
| 2005/0013726 A1 | 1/2005 | Hill |
| 2005/0013870 A1 | 1/2005 | Freyman et al. |
| 2005/0019830 A1* | 1/2005 | Penner ............... C07K 14/705 435/7.1 |
| 2005/0020965 A1 | 1/2005 | Rioux et al. |
| 2005/0033276 A1 | 2/2005 | Adachi |
| 2005/0043726 A1 | 2/2005 | McHale et al. |
| 2005/0048651 A1 | 3/2005 | Ryttsen |
| 2005/0049541 A1 | 3/2005 | Behar et al. |
| 2005/0054978 A1 | 3/2005 | Segal |
| 2005/0061322 A1 | 3/2005 | Freitag |
| 2005/0063974 A1 | 3/2005 | Reinhard |
| 2005/0066974 A1 | 3/2005 | Fields |
| 2005/0096537 A1 | 5/2005 | Parel et al. |
| 2005/0096709 A1 | 5/2005 | Skwarek |
| 2005/0107781 A1 | 5/2005 | Ostrovsky et al. |
| 2005/0112141 A1 | 5/2005 | Terman |
| 2005/0135393 A1 | 6/2005 | Benco |
| 2005/0143817 A1 | 6/2005 | Hunter et al. |
| 2005/0165393 A1 | 7/2005 | Eppstein |
| 2005/0171522 A1 | 8/2005 | Christopherson |
| 2005/0171523 A1 | 8/2005 | Rubinsky et al. |
| 2005/0171571 A1 | 8/2005 | Goodin |
| 2005/0171574 A1 | 8/2005 | Rubinsky et al. |
| 2005/0182462 A1 | 8/2005 | Chornenky |
| 2005/0197619 A1 | 9/2005 | Rule et al. |
| 2005/0203489 A1 | 9/2005 | Saadat |
| 2005/0216047 A1 | 9/2005 | Kumoyama |
| 2005/0228373 A1 | 10/2005 | Kelly |
| 2005/0228459 A1 | 10/2005 | Levin et al. |
| 2005/0228460 A1 | 10/2005 | Levin et al. |
| 2005/0234445 A1 | 10/2005 | Conquergood |
| 2005/0234523 A1 | 10/2005 | Levin et al. |
| 2005/0261672 A1 | 11/2005 | Deem et al. |
| 2005/0261707 A1 | 11/2005 | Schatzberger |
| 2005/0267407 A1 | 12/2005 | Goldman |
| 2005/0282284 A1 | 12/2005 | Rubinsky et al. |
| 2005/0283149 A1 | 12/2005 | Thorne |
| 2005/0288684 A1 | 12/2005 | Aronson et al. |
| 2005/0288702 A1 | 12/2005 | McGurk et al. |
| 2005/0288730 A1 | 12/2005 | Deem et al. |
| 2006/0004356 A1 | 1/2006 | Bilski |
| 2006/0004400 A1 | 1/2006 | McGurk et al. |
| 2006/0009748 A1 | 1/2006 | Mathis |
| 2006/0015147 A1 | 1/2006 | Persson et al. |
| 2006/0020347 A1 | 1/2006 | Barrett |
| 2006/0024359 A1 | 2/2006 | Walker et al. |
| 2006/0025760 A1 | 2/2006 | Podhajsky |
| 2006/0025821 A1 | 2/2006 | Gelfand |
| 2006/0030810 A1 | 2/2006 | Mandrusov |
| 2006/0074413 A1 | 4/2006 | Behzadian |
| 2006/0079838 A1 | 4/2006 | Walker |
| 2006/0079845 A1 | 4/2006 | Howard |
| 2006/0079883 A1 | 4/2006 | Elmouelhi et al. |
| 2006/0085054 A1 | 4/2006 | Zikorus |
| 2006/0089635 A1 | 4/2006 | Young et al. |
| 2006/0106379 A1 | 5/2006 | O'Brien |
| 2006/0121610 A1 | 6/2006 | Rubinsky et al. |
| 2006/0127703 A1 | 6/2006 | Takekuma |
| 2006/0142801 A1 | 6/2006 | Demarais et al. |
| 2006/0149123 A1 | 7/2006 | Vidlund |
| 2006/0173490 A1 | 8/2006 | Lafontaine |
| 2006/0182684 A1 | 8/2006 | Beliveau |
| 2006/0184163 A1 | 8/2006 | Breen et al. |
| 2006/0195146 A1 | 8/2006 | Tracey et al. |
| 2006/0206150 A1 | 9/2006 | Demarais et al. |
| 2006/0212032 A1 | 9/2006 | Daniel et al. |
| 2006/0212076 A1 | 9/2006 | Demarais et al. |
| 2006/0212078 A1 | 9/2006 | Demarais et al. |
| 2006/0217702 A1 | 9/2006 | Young |
| 2006/0217703 A1 | 9/2006 | Chornenky et al. |
| 2006/0217704 A1 | 9/2006 | Cockburn et al. |
| 2006/0224188 A1 | 10/2006 | Libbus et al. |
| 2006/0224192 A1 | 10/2006 | Dimmer et al. |
| 2006/0234752 A1 | 10/2006 | Mese |
| 2006/0235474 A1 | 10/2006 | Demarais |
| 2006/0241366 A1 | 10/2006 | Falwell |
| 2006/0247619 A1 | 11/2006 | Kaplan |
| 2006/0264752 A1 | 11/2006 | Rubinsky et al. |
| 2006/0264807 A1 | 11/2006 | Westersten et al. |
| 2006/0269531 A1 | 11/2006 | Beebe |
| 2006/0271111 A1 | 11/2006 | Demarais et al. |
| 2006/0276710 A1 | 12/2006 | Krishnan |
| 2006/0278241 A1 | 12/2006 | Ruano |
| 2006/0283462 A1 | 12/2006 | Fields et al. |
| 2006/0293713 A1 | 12/2006 | Rubinsky et al. |
| 2006/0293725 A1 | 12/2006 | Rubinsky et al. |
| 2006/0293730 A1 | 12/2006 | Rubinsky et al. |
| 2006/0293731 A1 | 12/2006 | Rubinsky et al. |
| 2006/0293734 A1 | 12/2006 | Scott et al. |
| 2007/0010805 A1 | 1/2007 | Fedewa et al. |
| 2007/0016125 A1 | 1/2007 | Wong |
| 2007/0016183 A1 | 1/2007 | Lee et al. |
| 2007/0016185 A1 | 1/2007 | Tullis |
| 2007/0021803 A1 | 1/2007 | Deem et al. |
| 2007/0025919 A1 | 2/2007 | Deem et al. |
| 2007/0043345 A1 | 2/2007 | Davalos et al. |
| 2007/0055142 A1 | 3/2007 | Webler |
| 2007/0055225 A1 | 3/2007 | Dodd, III |
| 2007/0060989 A1 | 3/2007 | Deem |
| 2007/0066957 A1 | 3/2007 | Demarais et al. |
| 2007/0066971 A1 | 3/2007 | Podhajsky |
| 2007/0078391 A1 | 4/2007 | Wortley et al. |
| 2007/0078453 A1 | 4/2007 | Johnson et al. |
| 2007/0083239 A1 | 4/2007 | Demarais et al. |
| 2007/0088347 A1 | 4/2007 | Young |
| 2007/0093789 A1 | 4/2007 | Smith |
| 2007/0096048 A1 | 5/2007 | Clerc |
| 2007/0118069 A1 | 5/2007 | Persson et al. |
| 2007/0129711 A1 | 6/2007 | Altshuler et al. |
| 2007/0129720 A1 | 6/2007 | Demarais |
| 2007/0129760 A1 | 6/2007 | Demarais |
| 2007/0137567 A1 | 6/2007 | Shimizu et al. |
| 2007/0151848 A1 | 7/2007 | Novak |
| 2007/0153135 A1 | 7/2007 | Han |
| 2007/0156129 A1 | 7/2007 | Kovalcheck |
| 2007/0156135 A1 | 7/2007 | Rubinsky et al. |

(56) References Cited

U.S. PATENT DOCUMENTS

| | | |
|---|---|---|
| 2007/0156136 A1 | 7/2007 | Godara et al. |
| 2007/0173899 A1 | 7/2007 | Levin et al. |
| 2007/0179380 A1 | 8/2007 | Grossman |
| 2007/0191589 A1 | 8/2007 | Hirota |
| 2007/0191889 A1 | 8/2007 | Lang |
| 2007/0197895 A1 | 8/2007 | Nycz et al. |
| 2007/0203486 A1 | 8/2007 | Young |
| 2007/0203549 A1 | 8/2007 | Demarais et al. |
| 2007/0230757 A1 | 10/2007 | Trachtenberg et al. |
| 2007/0239099 A1 | 10/2007 | Goldfarb et al. |
| 2007/0244521 A1 | 10/2007 | Bornzin et al. |
| 2007/0249939 A1 | 10/2007 | Gerbi |
| 2007/0282407 A1 | 12/2007 | Demarais |
| 2007/0287950 A1 | 12/2007 | Kjeken et al. |
| 2007/0295336 A1 | 12/2007 | Nelson et al. |
| 2007/0295337 A1 | 12/2007 | Nelson et al. |
| 2008/0015571 A1 | 1/2008 | Rubinsky et al. |
| 2008/0015628 A1 | 1/2008 | Dubrul |
| 2008/0015664 A1 | 1/2008 | Podhajsky |
| 2008/0021371 A1 | 1/2008 | Rubinsky et al. |
| 2008/0027314 A1 | 1/2008 | Miyazaki et al. |
| 2008/0027343 A1 | 1/2008 | Fields et al. |
| 2008/0033340 A1 | 2/2008 | Heller |
| 2008/0033417 A1 | 2/2008 | Nields et al. |
| 2008/0045880 A1 | 2/2008 | Kjeken et al. |
| 2008/0052786 A1 | 2/2008 | Lin |
| 2008/0065062 A1 | 3/2008 | Leung |
| 2008/0071262 A1 | 3/2008 | Azure |
| 2008/0071264 A1 | 3/2008 | Azure |
| 2008/0071265 A1 | 3/2008 | Azure |
| 2008/0082145 A1 | 4/2008 | Skwarek |
| 2008/0086115 A1 | 4/2008 | Stoklund |
| 2008/0091135 A1* | 4/2008 | Draghia-Akli ......... A61N 1/327 604/20 |
| 2008/0097139 A1 | 4/2008 | Clerc |
| 2008/0097422 A1 | 4/2008 | Edwards et al. |
| 2008/0103529 A1 | 5/2008 | Schoenbach |
| 2008/0121375 A1 | 5/2008 | Richason |
| 2008/0125772 A1 | 5/2008 | Stone et al. |
| 2008/0125775 A1 | 5/2008 | Morris |
| 2008/0132826 A1 | 6/2008 | Shadduck |
| 2008/0132884 A1 | 6/2008 | Rubinsky et al. |
| 2008/0132885 A1 | 6/2008 | Rubinsky et al. |
| 2008/0140064 A1 | 6/2008 | Vegesna |
| 2008/0146931 A1 | 6/2008 | Zhang |
| 2008/0146934 A1 | 6/2008 | Czygan et al. |
| 2008/0147056 A1 | 6/2008 | Van Der Weide |
| 2008/0154259 A1 | 6/2008 | Gough et al. |
| 2008/0167649 A1 | 7/2008 | Edwards et al. |
| 2008/0171985 A1 | 7/2008 | Karakoca |
| 2008/0183256 A1 | 7/2008 | Keacher |
| 2008/0190434 A1 | 8/2008 | Tjong |
| 2008/0200911 A1 | 8/2008 | Long |
| 2008/0200912 A1 | 8/2008 | Long |
| 2008/0208052 A1 | 8/2008 | LePivert et al. |
| 2008/0210243 A1 | 9/2008 | Clayton et al. |
| 2008/0213331 A1 | 9/2008 | Gelfand |
| 2008/0214986 A1 | 9/2008 | Ivorra |
| 2008/0224188 A1 | 9/2008 | Han |
| 2008/0234708 A1 | 9/2008 | Houser |
| 2008/0236593 A1 | 10/2008 | Nelson et al. |
| 2008/0249503 A1 | 10/2008 | Fields et al. |
| 2008/0255553 A1 | 10/2008 | Young |
| 2008/0262489 A1 | 10/2008 | Steinke |
| 2008/0269586 A1 | 10/2008 | Rubinsky et al. |
| 2008/0269838 A1 | 10/2008 | Brighton et al. |
| 2008/0275465 A1 | 11/2008 | Paul et al. |
| 2008/0279995 A1 | 11/2008 | Schultheiss et al. |
| 2008/0281319 A1 | 11/2008 | Paul et al. |
| 2008/0283065 A1 | 11/2008 | Chang |
| 2008/0288038 A1 | 11/2008 | Paul et al. |
| 2008/0294155 A1 | 11/2008 | Cronin |
| 2008/0294358 A1 | 11/2008 | Richardson |
| 2008/0300589 A1 | 12/2008 | Paul et al. |
| 2008/0306427 A1 | 12/2008 | Bailey |
| 2008/0312599 A1 | 12/2008 | Rosenberg |
| 2008/0319511 A1 | 12/2008 | Pless |
| 2009/0018206 A1 | 1/2009 | Barkan et al. |
| 2009/0018565 A1 | 1/2009 | To et al. |
| 2009/0018566 A1 | 1/2009 | Escudero et al. |
| 2009/0018567 A1 | 1/2009 | Escudero et al. |
| 2009/0024075 A1 | 1/2009 | Schroeppel et al. |
| 2009/0024085 A1 | 1/2009 | To et al. |
| 2009/0029407 A1 | 1/2009 | Gazit et al. |
| 2009/0030336 A1 | 1/2009 | Woo |
| 2009/0036773 A1 | 2/2009 | Lau et al. |
| 2009/0038752 A1 | 2/2009 | Weng |
| 2009/0062788 A1 | 3/2009 | Long et al. |
| 2009/0062792 A1 | 3/2009 | Vakharia et al. |
| 2009/0062795 A1 | 3/2009 | Vakharia |
| 2009/0076496 A1 | 3/2009 | Azure |
| 2009/0076499 A1 | 3/2009 | Azure |
| 2009/0076500 A1 | 3/2009 | Azure |
| 2009/0076502 A1 | 3/2009 | Azure et al. |
| 2009/0081272 A1 | 3/2009 | Clarke |
| 2009/0088636 A1 | 4/2009 | Lau et al. |
| 2009/0099544 A1 | 4/2009 | Munrow |
| 2009/0105703 A1 | 4/2009 | Shadduck |
| 2009/0114226 A1 | 5/2009 | Deem |
| 2009/0118725 A1 | 5/2009 | Auth et al. |
| 2009/0118729 A1 | 5/2009 | Auth et al. |
| 2009/0125009 A1 | 5/2009 | Zikorus |
| 2009/0138014 A1 | 5/2009 | Bonutti |
| 2009/0143705 A1 | 6/2009 | Danek et al. |
| 2009/0157166 A1 | 6/2009 | Singhal |
| 2009/0163904 A1 | 6/2009 | Miller et al. |
| 2009/0171280 A1 | 7/2009 | Samuel |
| 2009/0177111 A1 | 7/2009 | Miller et al. |
| 2009/0186850 A1 | 7/2009 | Kiribayashi |
| 2009/0192508 A1 | 7/2009 | Laufer et al. |
| 2009/0198227 A1 | 8/2009 | Prakash |
| 2009/0198231 A1 | 8/2009 | Esser et al. |
| 2009/0204005 A1 | 8/2009 | Keast et al. |
| 2009/0204112 A1 | 8/2009 | Kleyman |
| 2009/0209955 A1 | 8/2009 | Forster |
| 2009/0216543 A1 | 8/2009 | Pang |
| 2009/0221939 A1 | 9/2009 | Demarais et al. |
| 2009/0228001 A1 | 9/2009 | Pacey |
| 2009/0240247 A1 | 9/2009 | Rioux |
| 2009/0247933 A1 | 10/2009 | Maor et al. |
| 2009/0248012 A1 | 10/2009 | Maor et al. |
| 2009/0269317 A1 | 10/2009 | Davalos |
| 2009/0270756 A1 | 10/2009 | Gamache |
| 2009/0275827 A1 | 11/2009 | Aiken et al. |
| 2009/0281477 A1 | 11/2009 | Mikus |
| 2009/0281540 A1 | 11/2009 | Blomgren et al. |
| 2009/0287081 A1 | 11/2009 | Grossman |
| 2009/0292342 A1 | 11/2009 | Rubinsky et al. |
| 2009/0301480 A1 | 12/2009 | Elsakka |
| 2009/0306544 A1 | 12/2009 | Ng |
| 2009/0306545 A1 | 12/2009 | Elsakka |
| 2009/0318849 A1 | 12/2009 | Hobbs |
| 2009/0318905 A1 | 12/2009 | Bhargav |
| 2009/0326346 A1 | 12/2009 | Kracker |
| 2009/0326366 A1 | 12/2009 | Krieg |
| 2009/0326436 A1 | 12/2009 | Rubinsky et al. |
| 2009/0326561 A1 | 12/2009 | Carroll, II |
| 2009/0326570 A1 | 12/2009 | Brown |
| 2010/0004623 A1 | 1/2010 | Hamilton, Jr. |
| 2010/0006441 A1 | 1/2010 | Renaud |
| 2010/0016783 A1 | 1/2010 | Bourke, Jr. et al. |
| 2010/0023004 A1 | 1/2010 | Francischelli et al. |
| 2010/0030211 A1 | 2/2010 | Davalos et al. |
| 2010/0036291 A1 | 2/2010 | Darlington |
| 2010/0049190 A1 | 2/2010 | Long et al. |
| 2010/0056926 A1 | 3/2010 | Deckman |
| 2010/0057074 A1 | 3/2010 | Roman et al. |
| 2010/0057076 A1 | 3/2010 | Behnke |
| 2010/0069921 A1 | 3/2010 | Miller et al. |
| 2010/0079215 A1 | 4/2010 | Brannan |
| 2010/0082022 A1 | 4/2010 | Haley et al. |
| 2010/0082023 A1 | 4/2010 | Brannan |
| 2010/0082024 A1 | 4/2010 | Brannan |
| 2010/0082025 A1 | 4/2010 | Brannan |

(56) References Cited

U.S. PATENT DOCUMENTS

| | | |
|---|---|---|
| 2010/0082083 A1 | 4/2010 | Brannan |
| 2010/0082084 A1 | 4/2010 | Brannan |
| 2010/0087813 A1 | 4/2010 | Long |
| 2010/0090696 A1 | 4/2010 | Deimling |
| 2010/0100093 A1 | 4/2010 | Azure |
| 2010/0106025 A1 | 4/2010 | Sarfaty et al. |
| 2010/0106047 A1 | 4/2010 | Sarfaty et al. |
| 2010/0121173 A1 | 5/2010 | Sarfaty et al. |
| 2010/0130975 A1 | 5/2010 | Long |
| 2010/0147701 A1 | 6/2010 | Field |
| 2010/0152725 A1 | 6/2010 | Pearson |
| 2010/0160850 A1 | 6/2010 | Ivorra |
| 2010/0168735 A1 | 7/2010 | Deno et al. |
| 2010/0174282 A1 | 7/2010 | Demarais et al. |
| 2010/0179436 A1 | 7/2010 | Sarfaty et al. |
| 2010/0179530 A1 | 7/2010 | Long et al. |
| 2010/0191112 A1 | 7/2010 | Demarais et al. |
| 2010/0191235 A1 | 7/2010 | Moshe |
| 2010/0196984 A1 | 8/2010 | Rubinsky et al. |
| 2010/0204560 A1 | 8/2010 | Salahieh et al. |
| 2010/0204638 A1 | 8/2010 | Hobbs et al. |
| 2010/0211061 A1 | 8/2010 | Leyh |
| 2010/0222377 A1 | 9/2010 | Crooks |
| 2010/0222677 A1 | 9/2010 | Placek et al. |
| 2010/0228234 A1 | 9/2010 | Hyde |
| 2010/0228247 A1 | 9/2010 | Paul et al. |
| 2010/0241117 A1 | 9/2010 | Paul et al. |
| 2010/0249771 A1 | 9/2010 | Pearson et al. |
| 2010/0250209 A1 | 9/2010 | Pearson et al. |
| 2010/0255795 A1 | 10/2010 | Rubinsky et al. |
| 2010/0256624 A1 | 10/2010 | Brannan |
| 2010/0256628 A1 | 10/2010 | Pearson |
| 2010/0256630 A1 | 10/2010 | Hamilton, Jr. |
| 2010/0261994 A1 | 10/2010 | Davalos et al. |
| 2010/0262067 A1 | 10/2010 | Chornenky et al. |
| 2010/0268223 A1 | 10/2010 | Coe et al. |
| 2010/0268225 A1 | 10/2010 | Coe et al. |
| 2010/0286690 A1 | 11/2010 | Paul et al. |
| 2010/0292686 A1 | 11/2010 | Rick et al. |
| 2010/0298822 A1 | 11/2010 | Behnke |
| 2010/0298823 A1 | 11/2010 | Cao et al. |
| 2010/0298825 A1 | 11/2010 | Slizynski et al. |
| 2010/0331758 A1 | 12/2010 | Davalos et al. |
| 2010/0331911 A1 | 12/2010 | Kovalcheck |
| 2011/0009860 A1 | 1/2011 | Chornenky |
| 2011/0015630 A1 | 1/2011 | Azure |
| 2011/0017207 A1 | 1/2011 | Hendricksen |
| 2011/0021970 A1 | 1/2011 | Vo-Dinh et al. |
| 2011/0034209 A1 | 2/2011 | Rubinsky et al. |
| 2011/0054458 A1 | 3/2011 | Behnke |
| 2011/0064371 A1 | 3/2011 | Leatherman |
| 2011/0064671 A1 | 3/2011 | Bynoe |
| 2011/0082362 A1 | 4/2011 | Schmidt et al. |
| 2011/0082414 A1 | 4/2011 | Wallace |
| 2011/0092973 A1 | 4/2011 | Nuccitelli |
| 2011/0098695 A1 | 4/2011 | Brannan |
| 2011/0105823 A1 | 5/2011 | Single, Jr. et al. |
| 2011/0106221 A1 | 5/2011 | Neal et al. |
| 2011/0112434 A1 | 5/2011 | Ghabrial |
| 2011/0112531 A1 | 5/2011 | Landis et al. |
| 2011/0118721 A1 | 5/2011 | Brannan |
| 2011/0118727 A1 | 5/2011 | Fish et al. |
| 2011/0118729 A1 | 5/2011 | Heeren et al. |
| 2011/0118732 A1 | 5/2011 | Rubinsky et al. |
| 2011/0118734 A1 | 5/2011 | Auld |
| 2011/0130834 A1 | 6/2011 | Wilson |
| 2011/0135626 A1 | 6/2011 | Kovalcheck |
| 2011/0144524 A1 | 6/2011 | Fish et al. |
| 2011/0144562 A1 | 6/2011 | Heeren |
| 2011/0144635 A1 | 6/2011 | Harper et al. |
| 2011/0144638 A1 | 6/2011 | Heeren |
| 2011/0144641 A1 | 6/2011 | Dimalanta, Jr. et al. |
| 2011/0144657 A1 | 6/2011 | Fish et al. |
| 2011/0152678 A1 | 6/2011 | Aljuri |
| 2011/0152906 A1 | 6/2011 | Escudero et al. |
| 2011/0152907 A1 | 6/2011 | Escudero et al. |
| 2011/0160514 A1 | 6/2011 | Long et al. |
| 2011/0166499 A1 | 7/2011 | Demarais |
| 2011/0172659 A1 | 7/2011 | Brannan |
| 2011/0176037 A1 | 7/2011 | Benkley, III |
| 2011/0178570 A1 | 7/2011 | Demarais |
| 2011/0190851 A1 | 8/2011 | Kelly |
| 2011/0202052 A1 | 8/2011 | Gelbart et al. |
| 2011/0202053 A1 | 8/2011 | Moss |
| 2011/0207758 A1 | 8/2011 | Sobotka et al. |
| 2011/0208096 A1 | 8/2011 | Demarais et al. |
| 2011/0208180 A1 | 8/2011 | Brannan |
| 2011/0217730 A1 | 9/2011 | Gazit et al. |
| 2011/0230874 A1 | 9/2011 | Epstein et al. |
| 2011/0238057 A1 | 9/2011 | Moss |
| 2011/0245756 A1 | 10/2011 | Arora et al. |
| 2011/0251607 A1 | 10/2011 | Kruecker et al. |
| 2011/0282354 A1 | 11/2011 | Schulte |
| 2011/0288545 A1 | 11/2011 | Beebe |
| 2011/0301587 A1 | 12/2011 | Deem |
| 2011/0306971 A1 | 12/2011 | Long |
| 2012/0034131 A1 | 2/2012 | Rubinsky et al. |
| 2012/0046658 A1 | 2/2012 | Kreindel |
| 2012/0059255 A1 | 3/2012 | Paul et al. |
| 2012/0071870 A1 | 3/2012 | Salahieh |
| 2012/0071872 A1 | 3/2012 | Rubinsky et al. |
| 2012/0071874 A1 | 3/2012 | Davalos et al. |
| 2012/0085649 A1 | 4/2012 | Sano et al. |
| 2012/0089009 A1 | 4/2012 | Omary et al. |
| 2012/0090643 A1 | 4/2012 | Bertsch |
| 2012/0090646 A1 | 4/2012 | Tanaka |
| 2012/0095459 A1 | 4/2012 | Callas et al. |
| 2012/0101538 A1* | 4/2012 | Ballakur .............. A61B 18/10 607/3 |
| 2012/0109122 A1 | 5/2012 | Arena et al. |
| 2012/0130289 A1 | 5/2012 | Demarais et al. |
| 2012/0150172 A1* | 6/2012 | Ortiz ................ A61B 18/1477 606/41 |
| 2012/0165813 A1 | 6/2012 | Lee et al. |
| 2012/0179091 A1 | 7/2012 | Ivorra |
| 2012/0220999 A1 | 8/2012 | Long |
| 2012/0226218 A1 | 9/2012 | Phillips |
| 2012/0226271 A1 | 9/2012 | Callas et al. |
| 2012/0265183 A1 | 10/2012 | Tulleken |
| 2012/0265186 A1 | 10/2012 | Burger et al. |
| 2012/0277741 A1 | 11/2012 | Davalos et al. |
| 2012/0303012 A1 | 11/2012 | Leyh |
| 2012/0303020 A1 | 11/2012 | Chornenky |
| 2012/0310236 A1 | 12/2012 | Placek et al. |
| 2012/0310237 A1 | 12/2012 | Swanson |
| 2013/0023871 A1 | 1/2013 | Collins |
| 2013/0030239 A1 | 1/2013 | Weyh |
| 2013/0030430 A1 | 1/2013 | Stewart |
| 2013/0033977 A1 | 2/2013 | Lin |
| 2013/0035921 A1 | 2/2013 | Rodriguez-Ponce et al. |
| 2013/0041436 A1 | 2/2013 | Ruse et al. |
| 2013/0072858 A1 | 3/2013 | Watson |
| 2013/0090346 A1 | 4/2013 | Johns |
| 2013/0090646 A1 | 4/2013 | Moss et al. |
| 2013/0108667 A1 | 5/2013 | Soikum et al. |
| 2013/0110103 A1 | 5/2013 | Assmus |
| 2013/0110106 A1 | 5/2013 | Richardson |
| 2013/0184702 A1 | 7/2013 | Neal et al. |
| 2013/0196441 A1 | 8/2013 | Rubinsky |
| 2013/0197425 A1 | 8/2013 | Golberg |
| 2013/0202766 A1 | 8/2013 | Rubinsky |
| 2013/0218157 A1 | 8/2013 | Callas et al. |
| 2013/0230895 A1 | 9/2013 | Koblizek |
| 2013/0238062 A1 | 9/2013 | Ron Edoute et al. |
| 2013/0253415 A1 | 9/2013 | Sano et al. |
| 2013/0261389 A1 | 10/2013 | Long |
| 2013/0281968 A1 | 10/2013 | Davalos et al. |
| 2013/0296679 A1 | 11/2013 | Condie et al. |
| 2013/0338761 A1 | 12/2013 | Plowiecki |
| 2013/0345697 A1 | 12/2013 | Garcia et al. |
| 2013/0345779 A1 | 12/2013 | Maor |
| 2014/0005664 A1 | 1/2014 | Govari et al. |
| 2014/0017218 A1 | 1/2014 | Scott |
| 2014/0039489 A1 | 2/2014 | Davalos et al. |

(56) References Cited

U.S. PATENT DOCUMENTS

| | | |
|---|---|---|
| 2014/0046322 A1 | 2/2014 | Callas et al. |
| 2014/0052118 A1 | 2/2014 | Laske et al. |
| 2014/0066913 A1 | 3/2014 | Sherman |
| 2014/0081255 A1 | 3/2014 | Johnson et al. |
| 2014/0088578 A1 | 3/2014 | Rubinsky et al. |
| 2014/0094792 A1 | 4/2014 | Sharonov |
| 2014/0094793 A1 | 4/2014 | Sharonov |
| 2014/0107643 A1 | 4/2014 | Chornenky et al. |
| 2014/0111224 A1 | 4/2014 | Agate |
| 2014/0121663 A1 | 5/2014 | Pearson |
| 2014/0121728 A1 | 5/2014 | Dhillon |
| 2014/0163551 A1 | 6/2014 | Maor et al. |
| 2014/0207133 A1 | 7/2014 | Model |
| 2014/0276748 A1 | 9/2014 | Ku |
| 2014/0296844 A1 | 10/2014 | Moss |
| 2014/0309579 A1 | 10/2014 | Rubinsky |
| 2014/0378964 A1 | 12/2014 | Pearson |
| 2015/0025526 A1 | 1/2015 | Hua |
| 2015/0032105 A1 | 1/2015 | Azure |
| 2015/0066013 A1 | 3/2015 | Salahieh |
| 2015/0066020 A1 | 3/2015 | Epstein |
| 2015/0088120 A1 | 3/2015 | Garcia |
| 2015/0088220 A1 | 3/2015 | Callas |
| 2015/0112333 A1 | 4/2015 | Chorenky |
| 2015/0126922 A1 | 5/2015 | Willis |
| 2015/0134584 A1 | 5/2015 | Nakagawa |
| 2015/0141984 A1 | 5/2015 | Loomas |
| 2015/0152504 A1 | 6/2015 | Lin |
| 2015/0164584 A1 | 6/2015 | Davalos |
| 2015/0173824 A1 | 6/2015 | Davalos |
| 2015/0196351 A1 | 7/2015 | Stone |
| 2015/0201996 A1 | 7/2015 | Rubinsky |
| 2015/0265349 A1 | 9/2015 | Moss |
| 2015/0289923 A1 | 10/2015 | Davalos |
| 2015/0320478 A1 | 11/2015 | Cosman, Jr. |
| 2015/0320481 A1* | 11/2015 | Cosman, Jr. ........ A61B 18/1482 606/35 |
| 2015/0320488 A1 | 11/2015 | Moshe |
| 2015/0320999 A1 | 11/2015 | Nuccitelli |
| 2015/0327944 A1 | 11/2015 | Neal, II |
| 2016/0022957 A1 | 1/2016 | Hobbs |
| 2016/0066977 A1 | 3/2016 | Neal, II |
| 2016/0074114 A1 | 3/2016 | Pearson |
| 2016/0113708 A1 | 4/2016 | Moss |
| 2016/0143398 A1 | 5/2016 | Kim |
| 2016/0143698 A1 | 5/2016 | Garcia |
| 2016/0235470 A1 | 8/2016 | Callas |
| 2016/0287313 A1 | 10/2016 | Rubinsky |
| 2016/0287314 A1 | 10/2016 | Arena |
| 2016/0337310 A1 | 11/2016 | Faccin |
| 2016/0338758 A9 | 11/2016 | Davalos |
| 2016/0338761 A1 | 11/2016 | Chornenky |
| 2016/0354142 A1 | 12/2016 | Pearson |
| 2016/0367310 A1 | 12/2016 | Onik |
| 2017/0035501 A1 | 2/2017 | Chornenky |
| 2017/0065339 A1 | 3/2017 | Mickelsen |
| 2017/0137512 A1* | 5/2017 | Van Hoorick ......... C07K 16/28 |
| 2017/0189579 A1 | 7/2017 | Davalos |
| 2017/0209620 A1 | 7/2017 | Davalos |
| 2017/0266438 A1 | 9/2017 | Sano |
| 2017/0319851 A1 | 11/2017 | Athos |
| 2017/0348525 A1 | 12/2017 | Sano |
| 2017/0360323 A1 | 12/2017 | Li |
| 2017/0360326 A1 | 12/2017 | Davalos |
| 2018/0036529 A1 | 2/2018 | Jaroszeski |
| 2018/0071014 A1 | 3/2018 | Neal |
| 2018/0125565 A1 | 5/2018 | Sano |
| 2018/0132922 A1 | 5/2018 | Neal, II |
| 2018/0161086 A1 | 6/2018 | Davalos |
| 2018/0198218 A1 | 7/2018 | Regan |
| 2019/0023804 A1 | 1/2019 | Onik |
| 2019/0029749 A1 | 1/2019 | Garcia |
| 2019/0046255 A1 | 2/2019 | Davalos |
| 2019/0069945 A1 | 3/2019 | Davalos |
| 2019/0076528 A1 | 3/2019 | Soden |
| 2019/0083169 A1 | 3/2019 | Single |
| 2019/0133671 A1 | 5/2019 | Davalos |
| 2019/0175248 A1 | 6/2019 | Neal, II |
| 2019/0175260 A1 | 6/2019 | Davalos |
| 2019/0223938 A1 | 7/2019 | Arena |
| 2019/0232048 A1 | 8/2019 | Latouche |
| 2019/0233809 A1 | 8/2019 | Neal, II |
| 2019/0256839 A1 | 8/2019 | Neal, II |
| 2019/0282294 A1 | 9/2019 | Davalos |
| 2019/0328445 A1 | 10/2019 | Sano |
| 2019/0351224 A1 | 11/2019 | Sano |
| 2019/0376055 A1 | 12/2019 | Davalos |
| 2020/0046432 A1 | 2/2020 | Garcia |
| 2020/0046967 A1 | 2/2020 | Ivey |
| 2020/0093541 A9 | 3/2020 | Neal et al. |
| 2020/0197073 A1 | 6/2020 | Sano |
| 2020/0260987 A1 | 8/2020 | Davalos |
| 2020/0289188 A1 | 9/2020 | Forsyth |
| 2020/0323576 A1 | 10/2020 | Neal |
| 2020/0405373 A1 | 12/2020 | O'Brien |
| 2021/0022795 A1 | 1/2021 | Davalos |
| 2021/0023362 A1 | 1/2021 | Lorenzo |
| 2021/0052882 A1 | 2/2021 | Wasson |
| 2021/0113265 A1 | 4/2021 | D'Agostino |
| 2021/0137410 A1 | 5/2021 | O'Brien |
| 2021/0186600 A1 | 6/2021 | Davalos |
| 2021/0361341 A1 | 11/2021 | Neal, II |
| 2021/0393312 A1 | 12/2021 | Davalos |
| 2022/0151688 A1 | 5/2022 | Garcia |
| 2022/0161027 A1 | 5/2022 | Aycock |
| 2022/0290183 A1 | 9/2022 | Davalos |
| 2022/0362549 A1 | 11/2022 | Sano |
| 2023/0157759 A1 | 5/2023 | Garcia |
| 2023/0212551 A1 | 7/2023 | Neal, II |
| 2023/0248414 A1 | 8/2023 | Sano |
| 2023/0355293 A1 | 11/2023 | Davalos |
| 2023/0355968 A1 | 11/2023 | Davalos |
| 2024/0008911 A1 | 1/2024 | Davalos |
| 2024/0074804 A1 | 3/2024 | Neal |

FOREIGN PATENT DOCUMENTS

| | | |
|---|---|---|
| AU | 2005271471 A2 | 2/2006 |
| AU | 2006321574 A1 | 6/2007 |
| AU | 2006321918 A1 | 6/2007 |
| AU | 2009243079 A2 | 1/2011 |
| AU | 2012255070 | 1/2014 |
| AU | 2003227960 A1 | 6/2014 |
| AU | 2006321570 A1 | 6/2014 |
| AU | 2015259303 A1 | 11/2016 |
| CA | 2297846 | 2/1999 |
| CA | 2378110 A1 | 2/2001 |
| CA | 2445392 A1 | 11/2002 |
| CA | 2458676 A1 | 3/2003 |
| CA | 2487284 A1 | 12/2003 |
| CA | 2575792 A1 | 2/2006 |
| CA | 2631940 A1 | 6/2007 |
| CA | 2631946 A1 | 6/2007 |
| CA | 2632604 A1 | 6/2007 |
| CA | 2722296 A1 | 11/2009 |
| CA | 2751462 A1 | 11/2010 |
| CN | 1525839 A | 9/2004 |
| CN | 101534736 A | 9/2009 |
| CN | 102238921 | 9/2009 |
| CN | 102421386 A | 4/2012 |
| CN | 106715682 A | 5/2017 |
| CN | 112807074 A | 5/2021 |
| DE | 833111 | 3/1952 |
| DE | 863111 | 1/1953 |
| DE | 4000893 A1 | 7/1991 |
| DE | 60038026 T2 | 2/2009 |
| EP | 0218275 A1 | 4/1987 |
| EP | 0339501 A2 | 11/1989 |
| EP | 0378132 A2 | 7/1990 |
| EP | 0528891 A1 | 3/1993 |
| EP | 0533511 A1 | 3/1993 |
| EP | 0908156 | 4/1999 |
| EP | 0935482 A1 | 8/1999 |
| EP | 0998235 A1 | 5/2000 |

(56) References Cited

FOREIGN PATENT DOCUMENTS

| | | |
|---|---|---|
| EP | 1011495 A1 | 6/2000 |
| EP | 0528891 B1 | 7/2000 |
| EP | 1061983 A1 | 12/2000 |
| EP | 1196550 A2 | 4/2002 |
| EP | 1207797 A1 | 5/2002 |
| EP | 1344497 | 9/2003 |
| EP | 1406685 A1 | 4/2004 |
| EP | 1424970 A2 | 6/2004 |
| EP | 1439792 A1 | 7/2004 |
| EP | 1442765 A1 | 8/2004 |
| EP | 1462065 A2 | 9/2004 |
| EP | 1061983 B1 | 11/2004 |
| EP | 1493397 A1 | 1/2005 |
| EP | 1506039 A1 | 2/2005 |
| EP | 0935482 B1 | 5/2005 |
| EP | 1011495 B1 | 11/2005 |
| EP | 1791485 B1 | 6/2007 |
| EP | 1796568 A1 | 6/2007 |
| EP | 1207797 B1 | 2/2008 |
| EP | 1406685 B1 | 6/2008 |
| EP | 1962708 B1 | 9/2008 |
| EP | 1962710 B1 | 9/2008 |
| EP | 1962945 B1 | 9/2008 |
| EP | 1424970 B1 | 12/2008 |
| EP | 2280741 A1 | 2/2011 |
| EP | 2373241 B1 | 10/2011 |
| EP | 2381829 A1 | 11/2011 |
| EP | 2413833 A1 | 2/2012 |
| EP | 2429435 | 3/2012 |
| EP | 2488251 A2 | 8/2012 |
| EP | 2627274 | 8/2012 |
| EP | 2651505 | 8/2012 |
| EP | 2593179 | 5/2013 |
| EP | 2642937 A2 | 10/2013 |
| EP | 3143124 A1 | 3/2017 |
| EP | 3852868 A1 | 7/2021 |
| ES | 2300272 T3 | 6/2008 |
| ES | 2315493 | 4/2009 |
| JP | H10243947 A | 9/1998 |
| JP | 2001510702 A | 8/2001 |
| JP | 2002360712 A | 12/2002 |
| JP | 2003505072 A | 2/2003 |
| JP | 2003506064 A | 2/2003 |
| JP | 2004203224 A | 7/2004 |
| JP | 2004525726 A | 8/2004 |
| JP | 2004303590 A | 10/2004 |
| JP | 2005501596 A | 1/2005 |
| JP | 2005526579 A | 9/2005 |
| JP | 2007516792 | 6/2007 |
| JP | 2008508946 A | 3/2008 |
| JP | 4252316 A | 4/2009 |
| JP | 2009518130 A | 5/2009 |
| JP | 2009518150 A | 5/2009 |
| JP | 2009518151 A | 5/2009 |
| JP | 2009532077 A | 9/2009 |
| JP | 2010503496 A | 2/2010 |
| JP | 2010511467 A | 4/2010 |
| JP | 2011137025 A | 7/2011 |
| JP | 2012510332 A | 5/2012 |
| JP | 2012515018 A | 7/2012 |
| JP | 4252316 B2 | 9/2012 |
| JP | 2012521863 A | 9/2012 |
| JP | 2014501574 A | 1/2014 |
| JP | 2017518805 A | 7/2017 |
| JP | 6594901 B2 | 10/2019 |
| JP | 2019193668 A | 11/2019 |
| JP | 7051188 B2 | 4/2022 |
| KR | 101034682 B1 | 9/2012 |
| WO | WO9104014 A1 | 4/1991 |
| WO | 9614238 | 5/1996 |
| WO | WO9634571 A1 | 11/1996 |
| WO | WO9639531 A1 | 12/1996 |
| WO | 9810745 A1 | 3/1998 |
| WO | WO9814238 A1 | 4/1998 |
| WO | WO9901076 A1 | 4/1998 |
| WO | WO9904710 A1 | 2/1999 |
| WO | 0020554 A | 4/2000 |
| WO | WO0020554 A1 | 4/2000 |
| WO | WO0107583 A1 | 2/2001 |
| WO | WO0107584 A1 | 2/2001 |
| WO | WO0107585 A1 | 2/2001 |
| WO | WO0110319 A1 | 2/2001 |
| WO | WO0148153 A1 | 7/2001 |
| WO | WO0170114 A1 | 9/2001 |
| WO | WO02078527 A2 | 9/2001 |
| WO | WO02089686 A1 | 9/2001 |
| WO | WO03020144 A1 | 9/2001 |
| WO | 0181533 A1 | 11/2001 |
| WO | 0200554 A1 | 1/2002 |
| WO | 02100459 A2 | 12/2002 |
| WO | WO03047684 A2 | 6/2003 |
| WO | WO03099382 A1 | 12/2003 |
| WO | 2004008153 | 1/2004 |
| WO | WO2004037341 A2 | 5/2004 |
| WO | WO2005065284 A2 | 5/2004 |
| WO | 2004080347 A2 | 9/2004 |
| WO | WO2006017666 A2 | 2/2006 |
| WO | 2006031541 A1 | 3/2006 |
| WO | 2006130194 A2 | 12/2006 |
| WO | WO2007067628 A2 | 6/2007 |
| WO | WO2007067937 A2 | 6/2007 |
| WO | WO2007067938 A2 | 6/2007 |
| WO | WO2007067939 A2 | 6/2007 |
| WO | WO2007067940 A2 | 6/2007 |
| WO | WO2007067941 A2 | 6/2007 |
| WO | WO2007067943 A2 | 6/2007 |
| WO | WO2007070361 A2 | 6/2007 |
| WO | 2007100727 A2 | 9/2007 |
| WO | 2007123690 A2 | 11/2007 |
| WO | WO2007137303 A2 | 11/2007 |
| WO | 2008034103 A3 | 3/2008 |
| WO | WO2008063195 A1 | 5/2008 |
| WO | WO2008101086 A2 | 5/2008 |
| WO | WO2008101091 A2 | 8/2008 |
| WO | WO2009036468 A1 | 3/2009 |
| WO | 2009046176 A1 | 4/2009 |
| WO | 2009137800 A2 | 11/2009 |
| WO | WO2009134876 A1 | 11/2009 |
| WO | WO2009135070 A1 | 11/2009 |
| WO | 2010015592 | 2/2010 |
| WO | WO2010064154 A1 | 6/2010 |
| WO | 2010080974 A1 | 7/2010 |
| WO | 2010085765 | 7/2010 |
| WO | WO2010117806 A1 | 10/2010 |
| WO | WO2010118387 A1 | 10/2010 |
| WO | 2010128373 | 11/2010 |
| WO | WO2010132472 A1 | 11/2010 |
| WO | WO2010151277 A1 | 12/2010 |
| WO | 2011028937 | 3/2011 |
| WO | 2011047387 A | 4/2011 |
| WO | WO2011047387 A2 | 4/2011 |
| WO | WO2011062653 A1 | 5/2011 |
| WO | WO2011072221 A1 | 6/2011 |
| WO | WO2011135294 A1 | 11/2011 |
| WO | WO2012006533 A1 | 1/2012 |
| WO | WO2012051433 A2 | 4/2012 |
| WO | WO2012054560 A1 | 4/2012 |
| WO | WO2012054573 A2 | 4/2012 |
| WO | 2012063266 | 5/2012 |
| WO | 2012071526 A | 5/2012 |
| WO | WO2012071526 A2 | 5/2012 |
| WO | 2012088149 A | 6/2012 |
| WO | WO2012088149 A2 | 6/2012 |
| WO | WO2013176881 | 6/2012 |
| WO | WO2014039320 | 6/2012 |
| WO | 2012140376 | 10/2012 |
| WO | 2013052138 | 4/2013 |
| WO | 2015175570 A1 | 11/2015 |
| WO | 2015192027 A1 | 12/2015 |
| WO | 2016100325 A1 | 6/2016 |
| WO | 2016164930 A1 | 10/2016 |
| WO | 2017024123 A1 | 2/2017 |
| WO | 2017117418 A1 | 7/2017 |

(56) References Cited

FOREIGN PATENT DOCUMENTS

| | | |
|---|---|---|
| WO | 2020061192 A1 | 3/2020 |
| WO | 2022066768 A1 | 3/2022 |
| WO | 2023172773 A1 | 9/2023 |

OTHER PUBLICATIONS

International Search Report PCT-US-06-016045_IPRP dated Oct. 30, 2007.
International Search Report PCT-US-07-000084_ISR dated Dec. 14, 2007.
International Search Report PCT-US-07-000084_WOSA dated Dec. 14, 2007.
International Search Report PCT-US-07-000084_IPRP dated Jul. 8, 2008.
International Search Report 07716249_SESR dated Jan. 19, 2009.
International Search Report PCT-US-09-038661_ISR dated Jun. 12, 2009.
International Search Report PCT-US-09-042100_ISR dated Jul. 9, 2009.
International Search Report PCT-US-09-042100_WOSA dated Jul. 9, 2009.
International Search Report 06751655_SESR dated Oct. 16, 2009.
International Search Report 06751655.9_ESO dated Oct. 29, 2009.
International Search Report PCT-US-09-062806_ISR dated Jan. 19, 2010.
International Search Report PCT-US-09-062806_WOSA dated Jan. 19, 2010.
International Search Report PCT-US-09-047969_ISR dated Jan. 21, 2010.
International Search Report PCT-US-09-047969_WOSA dated Jan. 21, 2010.
International Search Report PCT-US-09-048270_ISR dated Feb. 11, 2010.
International Search Report PCT-US-09-048270_WOSA dated Feb. 11, 2010.
International Search Report PCT-US-10-029243_IPRP dated Jul. 30, 2010.
International Search Report PCT-US-10-029243_ISR dated Jul. 30, 2010.
International Search Report PCT-US-10-029243_WOSA dated Jul. 30, 2010.
International Search Report PCT-US-10-022011_ISR dated Aug. 30, 2010.
International Search Report PCT-US-10-022011_WOSA dated Aug. 30, 2010.
International Search Report PCT-US-09-038661_IPRP dated Sep. 28, 2010.
International Search Report PCT-US-09-047969_IPRP dated Dec. 21, 2010.
International Search Report PCT-US-10-036734_ISR dated Dec. 23, 2010.
International Search Report PCT-US-10-036734_WOSA dated Dec. 23, 2010.
International Search Report PCT-US-09-048270_IPRP dated Jan. 5, 2011.
International Search Report PCT-US-10-022011_IPRP dated Jul. 26, 2011.
International Search Report PCT-US-10-053077_ISR dated Aug. 2, 2011.
International Search Report PCT-US-10-053077_WOSA dated Aug. 2, 2011.
International Search Report PCT-US-10-029243_IPRP dated Oct. 4, 2011.
International Search Report PCT-US-11-024909_ISR dated Oct. 18, 2011.
International Search Report PCT-US-11-024909_WOSA dated Oct. 18, 2011.
International Search Report PCT-US-11-025003_ISR dated Oct. 24, 2011.
International Search Report PCT-US-11-025003_WOSA dated Oct. 24, 2011.
International Search Report PCT-US-09-042100_IPRP dated Nov. 2, 2011.
International Search Report PCT-US-10-036734_IPRP dated Nov. 29, 2011.
International Search Report PCT-US-09-062806_IPRP dated Jan. 4, 2012.
International Search Report PCT-US-10-053077_ISR_IPRP dated Apr. 17, 2012.
International Search Report 09739678_SESR dated May 3, 2012.
International Search Report PCT-US-09-042100_ESO dated May 11, 2012.
International Search Report 12002108_EPS dated May 30, 2012.
International Search Report PCT-US-11-056177_ISR dated May 30, 2012.
International Search Report PCT-US-11-056177_WOSA dated May 30, 2012.
International Search Report 12002108.4_ESO dated Jun. 12, 2012.
International Search Report PCT-US-11-062067_ISR dated Jul. 25, 2012.
International Search Report PCT-US-11-062067_WOSA dated Jul. 25, 2012.
International Search Report PCT-US-11-024909_IPRP dated Aug. 21, 2012.
Coates, et al, The electric discharge of the electric eel, Electrophorus electricus (Linnaeus), Zoologica: New York Zoological Society, pp. 1-32.
Lynn, et al, A new method for the generation and use of focused ultrasound in experimental biology, pp. 179-193.
Neumann, Rosenheck, Permeability changes induced by electric impulses in vesicular membranes, J. Membrane Biol., 1972, 10, pp. 279-290.
Crowley, Electrical breakdown of bimolecular lipid membranes as an electromechanical instability, Biophysical Journal, 1973, vol. 13, 711-724.
Zimmermann, et al., Dielectric breakdown of cell membranes, Biophysical Journal, 1974, vol. 14, pp. 881-899.
Organ, Electrophysiologic principles of radiofrequency lesion making, Appl. Neurophysiol., 1976, 39, pp. 69-76.
Kinosita, Jr., Tsong, Hemodialysis of human erythrocytes by a transient electric field, Biochemistry, 1977, vol. 74, No. 5, pp. 1923-1927.
Kinsoita, Jr., Tsong, Formation and resealing of pores of controlled sizes in human erythrocyte membrane, Aug. 1977, vol. 268, pp. 438-441.
Kinosita, Jr., Tsong, Voltage-induced pore formation and hemolysis of human erythrocytes, Biochimica et Biophysica Acta, 1977, pp. 227-242.
Baker, Knight, Calcium-dependent exocytosis in bovine adrenal medullary cells with leaky plasma membranes, Nature, Dec. 1978, vol. 276, pp. 620-622.
Gauger, Bentrup, A study of dielectric membrane breakdown in the Fucus egg, J. Membrane Biol., 1979, 48, pp. 249-264.
Erez, Shitzer, Controlled destruction and temperature distributions in biological tissues subjected to monactive electrocoagulation, Transactions of theASME, Feb. 1980, vol. 102, pp. 42-49.
Neumann, et al, Gene transfer into mouse lyoma cells by electroporation in high electric fields, The EMBO Journal, 1982, vol. 1, No. 7, pp. 841-845.
Seibert, et al, Clonal variation of MCF-7 breast cancer cells in vitro and in athymic nude mice, Cancer Research, May 1983, 43, pp. 2223-2239.
Brown, Phototherapy of tumors, World J. Surg., 1983, 7, 700-709.
Onik, et al, Ultraonic characteristics of frozen liver, Cryobiology, 1984, 21, pp. 321-328.
Gilbert, et al, The use of ultrsound imaging for monitoring cryosurgery, IEEE Frontiers of Engineering and computing in Health Care, 1984, pp. 107-111.
Onik, et al, Sonographic monitoring of hepatic cryosurgery in an experimental animal model, AJR, May 1985, 144, pp. 1043-1047.

(56) References Cited

OTHER PUBLICATIONS

Griffiths, The importance of phase measurement in electrical impedance tomography, Phys. Med. Biol., Nov. 1987, vol. 32, No. 11, pp. 1435-1444.
Okino, Mohri, Effects of high-voltage electrical impulse and an anticancer drug on in vivo growing tumors, Jpn. J. Cancer Res., Dec. 1987, 78, pp. 1319-1321.
Kinosita, Jr. et al, Electroporation of cell membrane visualized under a pulsed-laser fluorescence microscope, Biophys. J., Jun. 1988, vol. 53, pp. 1015-1019.
Amasha, et al, Quantitative assessment of impedance tomography for temperature measurements in microwave hyperthermia, Clin. Phys. Physiol. Meas., 1988, vol. 9, Suppl. A, pp. 49-53.
Asmai, et al, Dielectric properties of mouse lymphocytes and erythrocytes, Biochimica et Biophysica Acta, 1989, 1010, pp. 49-55.
Griffiths, Zhang, A dual-frequency electrical impedance tomography system, Phys. Med. Biol., 1989, vol. 34, No. 10, pp. 1465-1476.
Rowland, et al, Transvenous ablation of atrioventricular conduction with a low energy power source, Br Heart J, 1989, 62, pp. 361-366.
Marsazalek, et al, Schwan equation and transmembrane potential induced by alternating electric field, Biophysical Journal, Oct. 1990, vol. 58, pp. 1053-1058.
Tekle, et al, Electroporation by using bipolar oscillating electric field: An improved method for DNA transfection of NIH 3T3 cells, Biochemistry, May 1991, vol. 88, pp. 4230-4234.
Mir, et al, Electrochemotherapy potentiation of antitumour effect of bleomycin by local electric pulses, Eur. J. Cancer, 1991, vol. 27, No. 1, pp. 68-72.
Mir, et al, Electrochemotherapy, a novel antitumor treatment: first clinical trial, Cancerology, 1991, 313, pp. 613-618.
Narayan, Dahiya, Establishment and characterization of a human primay prostatic adenocarcinoma cell line (ND-1_, The Journal of Urology, Nov. 1992, vol. 148, pp. 1600-1604.
Griffiths, et al, Measurement of pharyngeal transit time by electrical impedance tomography, Clin. Phys. Physiol. Meas., 1993, vol. 13, Suppl. A, pp. 197-200.
Rols, et al, Highly efficient transfection of mammalian cells by electric field pulses application to large volumes of cell culture by using a flow system, Eur. J. Biochem., 1992, 205, pp. 115-121.
Brown, et al, Blood flow imaging using electrical impedance tomography, Clin. Phys. Physiol. Meas., 1992, vol. 13, Suppl. A, pp. 175-179.
Foster, et al, Production of prostatic lesions in canines usign transrectally administered high-intensity focused ultrasound, Eur Urol, 1993, pp. 330-336.
Shiina, et al, Percutaneous ethanol injection therapy for hepatocellular carcinoma: Results in 146 patients, AJR, May 1993, 160, pp. 1023-1028.
Salford, et al, A new brain tumour therapy combining bleomycin with in vivo electropermeabilization, Biochemical and Biohysical Research Communications, Jul. 30, 1993, vol. 194, No. pp. 938-943.
Glidewell, Ng, The use of magnetic resonance imaging data and the inclusion of anisotropic regions in electrical impedance tomography, ISA, 1993, pp. 251-257.
Gascoyne, et al, Membrane changes accompanying the induced differentiation of Friend murine erythroleukemia cells studied by dielectrophoresis, Biochimca et Biophysica Acta, 1993, 1149, pp. 119-126.
Foster, et al, High-intensity focused ultrsound in the treatment of prostatic disease, Eur Urol, 1993, 23(suppl1), pp. 29-33.
Andreason, Electroporation as a technique for the ransfer of macromolecules into mamalian cell lines, J. Tiss. Cult. Meth., 1993, 15, pp. 56-62.
Weaver, Electroporation: A general phenomenon for manipulating cells and tissues, Journal of Cellular Biochemistry, 1993, 51, pp. 426-435.
Barber, Electrical impedance tomography applied potential tomography, Advances in Biomedical Engineering, 1993, IOS Press, pp. 165-173.
Cook, et al, ACT3: a high-speed, high-precision electrical impedance tomograph, IEEE Transactions on Biomedical Engineering, 1994, vol. 41, No. 8, pp. 713-722.
Alberts, et al, Molecular biology of the Cell, Biocchemical education, 1994, 22(3), pp. 164.
Hughes, et al, An analysis of studies comparing electrical impedance tomography with x-ray videofluoroscopy in the assessment of swallowing, Physiol. Meas. 1994, 15, pp. A199-A209.
Griffiths, Tissue spectroscopy with electrical impedance tomography: Computer simulations, IEEE Transactions on Biomedical Engineering, Saep 1995, vol. 42, No. 9, pp. 948-954.
Gencer, et al, Electrical impedance tomography: Induced-currentimaging achieved with a multiple coil system, IEEE Transactions on Biomedical Engineering, Feb. 1996, vol. 43, No. 2, pp. 139-149.
Weaver, Chizmadzhev, Theory of electroporation: a review, Bioelectrochemistry and Bioenergetics, 1996, vol. 41, pp. 135-160.
Gimsa, et al, Dielectric spectroscopy of single human erythrocytes at physiological ionic strength: Dispersion of the cytoplasm, Biophysical Journal, Jul. 1996, vol. 71, pp. 495-506.
Cowley, Lifestyle Good news for boomers, Newsweek, Dec. 30, 1996.
International Search Report PCT-US-11-025003_IPRP dated Aug. 21, 2012.
Hall, et al, Nanosecond pulsed electric fields have differential effects on cells in the S-phase, DNA and Cell Biology, 2007, vol. 26, No. 3, pp. 160-171.
Hall, et al, Nanosecond pulsed electric fields induce apoptosis in p53-wildtype and p53-null HCT116 colon carcinoma cells, Apoptosis, May 23, 2007, 12, pp. 1721-1731.
Hapala, Breaking the Barrier: Methods for Reversible Permeabilization of Cellular Membranes, Critical Reviews in Biotechnology, 17(2): 105-122, 1997.
Hasgall, P. et al, "IT'IS Database for thermal and electromagnetic parameters of biological tissues," 2018, it.is.swiss/database%0A%0A, 4 pages.
He, et al, Nonlinear current response of micro electroporation and resealing dynamics for human cancer cells, Bioelectrochemistry, Jan. 29, 2008, 72, pp. 161-168.
Helczynska et al, "Hypoxia promotes a dedifferentiated phenotype in ductal breast carcinoma in situ." Cancer Research, vol. 63, pp. 1441-1444 (2003).
Heller, et al, Clinical Applications of Electrochemotherapy, Advanced Drug Delivery Reviews, vol. 35, pp. 119-129, 1999.
Hjouj, et al, MRI study on reversible and irreversible electroporation induced blood brain barrier disruption, Aug. 10, 2012, PLOS One, vol. 7, 8, e42817, pp. 1-9.
Hjouj, M. et al, "Electroporation-Induced BBB Disruption and Tissue Damage Depicted by MRI," Abstracts from 16th Annual Scientific Meeting of the Society for Neuro-Oncology in Conjunction with the AANS/CNS Section on Tumors, Nov. 17-20, 2011, Orange County California, Neuro-Oncology Supplement, vol. 13, Supplement 3, p. iii114.
Hjouj, M., et al., "MRI Study on Reversible and Irreversible Electroporation Induced Blood Brain Barrier Disruption", PLOS One, Aug. 2012, 7:8, e42817.
Ho, et al., Electroporation of Cell Membranes: A Review, Critical Reviews in Biotechnology, 16(4): 349-362, 1996.
Hoejholt, K. L. et al. Calcium electroporation and electrochemotherapy for cancer treatment: Importance of cell membrane composition investigated by lipidomics, calorimetry and in vitro efficacy. Scientific Reports (Mar. 18, 2019) 9:4758, p. 1-12.
Holder, et al., Assessment and Calibration of a Low-Frequency System for Electrical Impedance Tomography (EIT), Optimized for Use in Imaging Brain Function in Ambulant Human Subjects, Annals of the New York Academy of Science, vol. 873, Issue 1, Electrical BI, pp. 512-519, 1999.
Hong, et al, Cardiac ablation via electroporation, 31st Annual International Conference of the IEEE EMBS, IEEE, Sep. 2, 2009, pp. 3381-3384.

(56) References Cited

OTHER PUBLICATIONS

Hu, Q., et al., "Simulations of transient membrane behavior in cells subjected to a high-intensity ultrashort electric pulse", Physical Review E, 71(3) (2005).
Huang, Rubinsky, Micro-electroporation: improving the efficiency and understanding of electrical permeabilization of cells, Biomedical Microdevices, 1999, 2:2, pp. 145-150.
International Search Report for 06751655 SESR dated Oct. 9, 2016. 3 pages.
International Search Report for 10824248.8 ESO dated Jan. 20, 2014. 3 pages.
International Search Report for 11833421 SESR dated Mar. 18, 2014. 2 pages.
International Search Report for IPRP, PCT/US2006/01645, dated Oct. 30, 2007, 5 pages.
International Search Report for PCT/US2011/056177 ESO dated Mar. 28, 2014.
International Search Report for PCT/US2011/056177 IPRP dated Apr. 16, 2013. 6 pages.
International Search Report for PCT/US2011/062067 IPRP dated May 28, 2013.
International Search Report for PCT/US2015/065792 mailed Feb. 9, 2016. 7 pages.
ISSA, et al, Recent Reports: The TUNA procedure for BPH: Review of the technology, Infections in Urology, Jul. 1998, 8 pages.
ISSA, et al, Specialty Surgery: The TUNA procedure for BPH: Basic procedure and clinical results, Infections in Urology, Sep. 1998, 6 pages.
ISSA, et al, The TUNA Procedure for BPH: Review of the Technology: The TUNA Procedure for BPH: Basic Procedure and Clinical Results, Reprinted from Infections in Urology, Jul./Aug. 1998 and Sep./Oct. 1998. 8 pages.
Ivanusa, et al., MRI Macromolecular Contrast Agents as Indicators of Changed Tumor Blood Flow, Radiol. Oncol. 2001; 35(2): 139-47.
Ivey, J_ W., E. L. Latouche, M. B. Sano, J_ H. Rossmeisl, R. V. Davalos, and S. S. Verbridge, "Targeted cellular ablation based on the morphology of malignant cells," Sci. Rep., vol. 5, pp. 1-17, 2015.
Ivorra et al., "In vivo electric impedance measurements during and after electroporation of rat live." Bioelectrochemistry, vol. 70, pp. 287-295 (2007).
Ivorra et al., "In vivo electrical conductivity measurements during and after tumor electroporation: conductivity changes reflect the treatment outcome." Physics in Medicine and Biology, vol. 54, pp. 5949-5963 (2009).
Ivorra, "Bioimpedance monitoring for physicians: an overview." Biomedical Applications Group, 35 pages (2002).
Ivorra, A., ed. "Tissue Electroporation as a Bioelectric Phenomenon: Basic Concepts. Irreversible Electroporation", ed. B. Rubinsky., Springer Berlin Heidelberg. 23-61 (2010).
Ivorra, et al., Impedance analyzer for in vivo electroporation studies, Proceedings of the 28th IEEE EMBS Annual International Conference, IEEE, Aug. 30, 2006, pp. 5056-5059.
Jan Ko et al, "New anti-huntingtin monoclonal antibodies: implications for huntingtin conformation and its binding proteins", Brain Research Bulletin, Elsevier Science Ltd, Oxford, GB, (Oct. 1, 2001), vol. 56, No. 3-4, doi:10.1016/S0361-9230(01)00599-8, ISSN 0361-9230, pp. 319-329, XP002509144.
Jarm et al., "Antivascular effects of electrochemotherapy: implications in treatment of bleeding metastases." Expert Rev Anticancer Ther. Vol. 10, pp. 729-746 (2010).
Jaroszeski, et al., In Vivo Gene Delivery by Electroporation, Advanced Drug Delivery Review, vol. 35, pp. 131-137, 1999.
Jensen et al., "Tumor volume in subcutaneous mouse xenografts measured by microCT is more accurate and reproducible than determined by 18FFDG-microPET or external caliper." BMC medical Imaging vol. 8: 16, 9 Pages (2008).
Jiang, et al, Membrane-targeting approaches for enhanced cancer cell destruction with irreversible electroporation, Annuals of Biomedical Engineering, Aug. 15, 2013.

Jordan, D.W., et al., "Effect of pulsed, high-power radiofrequency radiation on electroporation of mammalian cells". Ieee Transactions on Plasma Science, 32(4): p. 1573-1578 (2004).
Jossinet et al., Electrical Impedance Endo-Tomography: Imaging Tissue From Inside, IEEE Transactions on Medical Imaging, vol. 21, No. 6, Jun. 2002, pp. 560-565.
Kanduser, et al., Cell membrane fluidity related to electroporation and resealing, Eur Biophys J, Oct. 8, 2006, 35, pp. 196-204.
Katsuki, S., et al., "Biological effects of narrow band pulsed electric fields", Ieee Transactions on Dielectrics and Electrical Insulation,. 14(3): p. 663-668 (2007).
Kingham et al., "Ablation of perivascular hepatic malignant tumors with irreversible electroporation." Journal of the American College of Surgeons, 2012. 215(3), p. 379-387.
Kirson et al., "Alternating electric fields arrest cell proliferation in animal tumor models and human brain tumors." Proceedings of the National Academy of Sciences vol. 104, pp. 10152-10157 (2007).
Knight, et al, Direct imaging of transvenous radiofrequency cardiac ablation using a steerable fiberoptic infrared endoscope, Heart Rhythm Society, Oct. 2005, vol. 2, No. 10, pp. 1116-1121.
Kolb, J.F., et al., "Nanosecond pulsed electric field generators for the study of subcellular effects", Bioelectromagnetics, 27(3): p. 172-187 (2006).
Kotnik and Miklavcic, "Theoretical evaluation of voltage inducement on internal membranes of biological cells exposed o electric fields." Biophysical Journal, vol. 90(2), pp. 480-491 (2006).
Kotnik et al., "Sensitivity of transmembrane voltage induced by applied electric fields-A theoretical analysis", Bioelectrochemistry and Bioenergetics, vol. 43, Issue 2, 1997, pp. 285-291.
Kotnik, T. and D. Miklavcic, "Theoretical evaluation of the distributed power dissipation in biological cells exposed to electric fields", Bioelectromagnetics, 21(5): p. 385-394 (2000).
Verbridge et al., "Oxygen-Controlled Three-Dimensional Cultures to Analyze Tumor Angiogenesis." Tissue Engineering, Part A vol. 16, pp. 2133-2141 (2010).
Verma, A. et al., "Primer on Pulsed Electrical Field Ablation: Understanding the Benefits and Limitations," Circ. Arrhythmia Electrophysiol., No. September, pp. 1-16,2021, 16 pages.
Vernier, P.T., et al., "Nanoelectropulse-driven membrane perturbation and small molecule permeabilization", Bmc Cell Biology, 7 (2006). 16 pages.
Vidamed, Inc., "Highlights from Worldwide Clinical Studies: Transurethral Needle Ablation (TUNA)," Vidamed's Office TUNA System, (4 pages) (2001).
Vizintin, A. et al., "Effect of interphase and interpulse delay in high-frequency irreversible electroporation pulses on cell survival, membrane permeabilization and electrode material release," Bioelectrochemistry, vol. 134, Aug. 2020, 14 pages.
Voyer, D., A. Silve, L. M. Mir, R. Scorretti, and C. Poignard, "Dynamical modeling of tissue electroporation," Bioelectrochemistry, vol. 119, pp. 98-110, 2018.
Wandel, A. et al. "Optimizing Irreversible Electroporation Ablation with a Bipolar Electrode," Journal of Vascular and Interventional Radiology, vol. 27, Issue 9, 1441-1450.e2, 2016.
Wasson, Elisa M. et al. The Feasibility of Enhancing Susceptibility of Glioblastoma Cells to IRE Using a Calcium Adjuvant. Annals of Biomedical Engineering, vol. 45, No. 11, Nov. 2017 pp. 2535-2547.
Weaver et al., "A brief overview of electroporation pulse strength-duration space: A region where additional intracellular effects are expected." Bioelectrochemistry vol. 87, pp. 236-243 (2012).
Weaver, J. C., Electroporation of biological membranes from multicellular to nano scales, IEEE Trns. Dielectr. Electr. Insul. 10, 754-768 (2003).
Weaver, J.C., "Electroporation of cells and tissues", IEEE Transactions on Plasma Science, 28(1): p. 24-33 (2000).
Weisstein: Cassini Ovals. From MathWorld—A. Wolfram Web Resource; Apr. 30, 2010; http://mathworld.wolfram.com/ (updated May 18, 2011) 2 pages.
Wimmer, Thomas, et al., "Planning Irreversible Electroporation (IRE) in the Porcine Kidney: Are Numerical Simulations Reliable for Predicting Empiric Ablation Outcomes?", Cardiovasc Intervent Radiol. Feb. 2015 ; 38(1): 182-190. doi:10.1007/s00270-014-0905-2.

(56) References Cited

OTHER PUBLICATIONS

Wittkampf, et al., Myocardial lesion depth with circular electroporation ablation, Circ Arrhythm Electrophysiol, 2012, 5, pp. 581-586.
Wood et al., Technologies for Guidance of Radiofrequency Ablation in the Multimodality Interventional Suite of the Future, Jan. 2007, National Institutes of Health, pp. 1-26.
Wright, On a relationship between the arrhenius parameters from thermal damage studies, Technical Brief, Journalof Biomechanical Engineering, Transactions of the ASME, Apr. 2003, vol. 125, pp. 300-304.
Yang et al., "Dielectric properties of human leukocyte subpopulations determined by electrorotation as a cell separation criterion." Biophysical Journal, vol. 76, pp. 3307-3314 (1999).
Yao et al., "Study of transmembrane potentials of inner and outer membranes induced by pulsed-electric-field model and simulation." IEEE Trans Plasma Sci, 2007. 35(5): p. 1541-1549.
Yarmush, M. L. et al., "Electroporation-Based Technologies for Medicine: Principles, Applications, and Challenges," Annu. Rev. Biomed. Eng., vol. 16, No. 1, 295-320, 2014, 29 pages.
Ybarra, Gary A, et al. "Breast Imaging using Electrical Impedance Tomography." in Suri, J.S., R.M. Rangayyan, and S. Laxminarayan, Emerging Technologies in Breast Imaging and Mammography2008: American Scientific Publishers.
Zhang, et al., MR imaging to assess immediate response to irreversible electroporation for targeted ablation of liver tissues: Preclinical feasibility studies in a rodent model, Radiology, Aug. 2010, vol. 256, No. 2, pp. 424-432.
Zhao, J. et al. "Irreversible electroporation reverses resistance to immune checkpoint blockade in pancreatic cancer", Nature Communications (2019) 10:899,14 pages.
Zhao, Y. et al., "Characterization of conductivity changes during high-frequency irreversible electroporation for treatment planning," IEEE Transactions on Biomedical Engineering, vol. 65, No. 8, pp. 1810-1819, 2017.
Zhou, et al, Electroporation-mediated transfer of plasmids to the lung results in reduced TLR9 signaling and Inflammation, Gene Therapy, Mar. 8, 2007, 14, pp. 775-780.
Zlotta, et al., Long-Term Evaluation of Transurethral Needle Ablation of the Prostate (TUNA) for Treatment of Benign Prostatic Hyperplasia (BPH): Clinical Outcome After 5 Years. (Abstract) Presented at 2001 AUA National Meeting, Anaheim, CA—Jun. 5, 2001. 1 page.
Zlotta, et al., Possible Mechanisms of Action of Transurethral Needle Ablation of the Prostate on Benign Prostatic Hyperplasia Symptoms: a Neurohistochemical Study, Reprinted from Journal of Urology, vol. 157, No. 3, Mar. 1997, pp. 894-899.
Pavselj, N., et al., "A numerical model of skin electroporation as a method to enhance gene transfection in skin. 11th Mediterranean Conference on Medical and Biological Engineering and Computing", vols. 1 and 2, 16(1-2): p. 597-601 (2007).
PCT Application No. PCT/2011/062067, International Preliminary Report on Patentability dated May 28, 2013. 7 pages.
PCT Application No. PCT/2011/066239, International Preliminary Report on Patentability dated Jun. 25, 2013. 7 pages.
PCT Application No. PCT/US 19/51731 (VTIP-A1001-PCT), International Search Report and Written Opinion dated Feb. 20, 2020,19 pgs.
PCT Application No. PCT/US10/53077, International Search Report (Aug. 2, 2011), Written Opinion (Aug. 2, 2011), and International Preliminary Report on Patentability (Apr. 17, 2012). 14 pages.
PCT Application No. PCT/US15/30429 (VTIP-97), International Search Report and Written Opinion dated Oct. 16, 2015,19 pages.
PCT Application No. PCT/US15/30429, International Report on Patentability dated Nov. 15, 2016. 7 pages.
PCT Application No. PCT/US15/65792, International Search Report (Feb. 9, 2016), Written Opinion (Feb. 9, 2016), and International Preliminary Report on Patentability (Jun. 20, 2017), 15 pages.
PCT Application No. PCT/US19/51731, International Preliminary Report on Patentability dated Mar. 23, 2021, 13 pages.
PCT Application No. PCT/US2004/043477, International Search Report (Aug. 26, 2005), Written Opinion (Aug. 26, 2005), and International Preliminary Report on Patentability (Jun. 26, 2006). 10 pages.
PCT Application No. PCT/US2009/042100, International Search Report (Jul. 9, 2009), Written Opinion (Jul. 9, 2009), and International Preliminary Report on Patentability (Nov. 2, 2010).
PCT Application No. PCT/US2010/030629, International Search Report (Jul. 15, 2010), Written Opinion (Jul. 15, 2010), and International Preliminary Report on Patentability (Oct. 11, 2011).
PCT Application No. PCT/US2011/062067, International Search Report and Written Opinion dated Jul. 25, 2012.
PCT Application No. PCT/US2011/066239, International Search Report (Aug. 22, 2012), and Written Opinion (Aug. 22, 2012).
PCT International Search Report and Written Opinion from PCT/US2010/053077, dated Aug. 2, 2011.
PCT International Search Report for WO 2012/051433 mailed May 30, 2012. 6 pages.
Pech, et al., Irreversible electroporation of renal cell carcinoma: A first-in-man phase I clinical study, Cardiovasc Intervent Radiol, Aug. 15, 2010.
Pending Application No. PCT/US21/51551 (VTIP-A1018-PCT), International Search Report and Written Opinion dated Dec. 29, 2021, 14 pages.
Pending Application No. PCT/US23/15118 (VTIP-A1023-PCT), International Search Report and Written Opinion dated Jul. 31, 2023, 18 pages.
Pending Application No. PCT/US23/15118 (VTIP-A1023-PCT), Invitation to Pay Additional Fees dated May 17, 2023, 3 pages.
Persichetti F et al, "Normal and Expanded Huntington's Disease Gene Alleles Produce Distinguishable Proteins Due to Translation Across the Cag Repeat", Molecular Medicine, Feinstein Institute for Medical Research, Washington, DC; US, (May 1, 1995), vol. 1, No. 4, ISSN 1076-1551, pp. 374-383, XP000997528.
Philips, IntelliVue Patient Monitor, Jan. 2008, Philips, pp. 1-532 (Year: 2008).
Phillips, et al, Irreversible electroporation on the small intestine, British Journal of Cancer, 2012, pp. 1-6.
Phillips, et al, Nonthermal irreversible electroporation for tissue decellularization, Journal of Biomedical Engineering, Aug. 16, 2010, vol. 132, 091003, pp. 1-8.
Phillips, M., Maor, E. & Rubinsky, B. Nonthermal Irreversible Electroporation for Tissue Decellularization. J. Biomech. Eng, doi: : 10.1115/1.4001882 (2010). 8 pages.
Piñero, et al., Apoptotic and Necrotic Cell Death Are Both Induced by Electroporation in HL60 Human Promyeloid Leukaemia Cells, Apoptosis, vol. 2, No. 3, 330-336, Aug. 1997.
Polajzer, T. et al., "Cancellation effect is present in high-frequency reversible and irreversible electroporation," Bioelectrochemistry, vol. 132, 2020, 11 pages.
Polak et al., "On the Electroporation Thresholds of Lipid Bilayers: Molecular Dynamics Simulation Investigations." The Journal of Membrane Biology, vol. 246, pp. 843-850 (2013).
Polak, et al, On the electroporation thresholds of lipid bilayers: Molecular dynamics simulation investigations, J Membrane Biol, Jun. 13, 2013, 246, pp. 843-850.
Precision Office Tuna System, "When Patient Satisfaction is Your Goal." Product Literature Published by VidaMed, Inc., 11 pages (2001).
Pucihar et al., "Numerical determination of transmembrane voltage induced on irregularly shaped cells." Annals of Biomedical Engineering, vol. 34, pp. 642-652 (2006).
Qiao et al. Electrical properties of breast cancer cells from impedance measurement of cell suspensions, 2010, Journal of Physics, 224, 1-4 (2010).
Radeva, et al, Induction of apoptosis and necrosis in cancer cells by electric fields, electromagnetic fields, and photodynamically active quinoids, Electromagnetic Biology and Medicine, 2003, 23, pp. 185-200.
Rajagopal, V. and S.G. Rockson, Coronary restenosis: a review of mechanisms and management, The American Journal of Medicine, 2003, 115(7): p. 547-553.

(56) References Cited

OTHER PUBLICATIONS

Rebersek, et al., Advantages and disadvantages of different concepts of electroporation pulse generation, Automatika, 2011, 52, 1, pp. 12-19.
Rebersek, M. and D. Miklav, "Advantages and Disadvantages of Different Concepts of Electroporation Pulse Generation," Automatika 52(2011) 1, 12-19.
Reilly, J. P. et al., "Sensory Effects of Transient Electrical Stimulation-Evaluation with a Neuroelectric Model," IEEE Trans. Biomed. Eng., vol. BME-32, No. 12, 1001-1011, 1985, 11 pages.
Ringel-Scaia, V. M. et al., High-frequency irreversible electroporation is an effective tumor ablation strategy that induces immunologic cell death and promotes systemic anti-tumor immunity. EBioMedicine, 2019,44, 112-125.
Rogers, W. R. et al., "Strength-duration curve an electrically excitable tissue extended down to near 1 nanosecond," IEEE Trans. Plasma Sci., vol. 32, No. 4 II, 1587-1599, 2004, 13 pages.
Ron et al., "Cell-based screening for membranal and cytoplasmatic markers using dielectric spectroscopy." Biophysical chemistry, 135 (2008) pp. 59-68.
Rossmeisl et al., "Pathology of non-thermal irreversible electroporation (N-TIRE)-induced ablation of the canine brain." Journal of Veterinary Science vol. 14, pp. 433-440 (2013).
Rossmeisl, "New Treatment Modalities for Brain Tumors in Dogs and Cats." Veterinary Clinics of North America: Small Animal Practice 44, pp. 1013-1038 (2014).
Rossmeisl, John H. et al. Safety and feasibility of the NanoKnife system for irreversible electroporation ablative treatment of canine spontaneous intracranial gliomas. J. Neurosurgery 123.4 (2015): 1008-1025.
Rubinsky, B., "Irreversible Electroporation in Medicine", Technology in Cancer Research and Treatment, vol. 6, No. 4, Aug. 1, 2007, pp. 255-259.
Rubinsky, B., ed, Cryosurgery. Annu Rev. Biomed. Eng. Vol. 2 2000. 157-187.
Rubinsky, B., et al., "Irreversible Electroporation: A New Ablation Modality—Clinical Implications" Technol. Cancer Res. Treatment 6(1), 37-48 (2007).
Rubinsky, et al, Optimal parameters for the destruction of prostate cancer using irreversible electroporation, The Journal of Urology, Dec. 2008, vol. 180, pp. 2668-2674.
Rubinsky, L. et al., "Electrolytic Effects During Tissue Ablation by Electroporation," Technol. Cancer Res. Treat., vol. 15, No. 5, NP95-103, 2016, 9 pages.
Sabuncu, et al, Dielectrophoretic separation of mouse melanoma clones, Biomicrofluidics, Jun. 16, 2010, 4, 021101, pp. 1-7.
SAI Infusion Technologies, "Rabbit Ear Vein Catheters", https://www.sai-infusion.com/products/rabbit-ear-catheters Aug. 10, 2017 webpage printout, 5 pages.
Huang, et al., Micro-Electroporation: Improving the Efficiency and Understanding of Electrical Permeabilization of Cells, Biomedical Microdevices, vol. 2, pp. 145-150, 1999.
Ibey et al., "Selective cytotoxicity of intense mnanosecond-duration electric pulses in mammalian cells." Biochimica Et Biophysica Acta-General Subjects, vol. 1800, pp. 1210-1219 (2010).
Long, G., et al., "Targeted Tissue Ablation With Nanosecond Pulses". IEEE Transactions on Biomedical Engineering, 58(8) (2011).
"TUNA—Suggested Local Anesthesia Guidelines." Published by VidaMed, Inc. (1 page) (2001).
(Sano, Michael B. et al.) Co-Pending Application No. CN 202011281572.3, filed Nov. 16, 2020, Specification, Claims, Figures (Chinese version, 129 pages (see also WO 2015/175570), English Version of claims, 2 pages).
Abiror, I.G., et al., "Electric Breakdown of Bilayer Lipid-Membranes . 1. Main Experimental Facts and Their Qualitative Discussion", Bioelectrochemistry and Bioenergetics, 6(1): p. 37-52 (1979).
Agerholm-Larsen, B., et al., "Preclinical Validation of Electrochemotherapy as an Effective Treatment for Brain Trumors", Cancer Research 71: 3753-3762 (2011).

Al-Khadra, et al., The role of electroporation in defibrillation, Circulation Research, Oct. 27, 2000, 87, pp. 797-804.
Al-Sakere et al., "Tumor ablation with irreversible electroporation." PLoS One, Issue 11, e1135, 8 pages, 2007.
Al-Sakere, et al., A study of the immunological response to tumor ablation with irreversible electroporation, Technology in Cancer Research and Treatment, Aug. 2007, vol. 6, No. 4, pp. 301-305.
Alberts et al., "Molecular Biology of the Cell," 3rd edition, Garland Science, New York, 1994, 1 page.
Albright, et al, Performance and complicatioins associated with the Synchromed 10-ml infusion pump for intrathecal baclofen administration in children, J Neurosurg (Pediatrics 2), Aug. 2004, vol. 101, pp. 64-68.
Alinezhadbalalami, N. et al., "Generation of Tumor-activated T cells Using Electroporation", Bioelectrochemistry 142 (2021) 107886, Jul. 13, 2021, 11 pages.
Appelbaum et al., "US Findings after Irreversible Electroporation Ablation: Radiologic-Pathologic Correlation," Radiology, 262, pp. 117-125, Jan. 1, 2012.
Arena et al. "High-Frequency Irreversible Electroporation (H-FIRE) for Non-thermal Ablation without Muscle Contraction." Biomed. Eng. Online, vol. 10, 20 pages (2011).
Arena, C. B. et al., "Theoretical Considerations of Tissue Electroporation With High-Frequency Bipolar Pulses," IEEE Trans. Biomed. Eng., vol. 58, No. 5, 1474-1482, 2011, 9 pages.
Arena, C.B., et al., "A three-dimensional in vitro tumor platform for modeling therapeutic irreversible electroporation." Biophysical Journal, 2012.103(9): p. 2033-2042.
Arena, Christopher B., et al., "Phase Change Electrodes for Reducing Joule Heating During Irreversible Electroporation". Proceedings of the ASME 2012 Summer Bioengineering Conference, SBC2012, Jun. 20-23, 2012, Fajardo, Puerto Rico.
Arena, et al., Theoretical considerations of tissue electropration with high frequency biopolar pulses, IEEEE, pp. 1-7, (2010).
Arena, et al., Towards the development of latent heat storage electrodes for electroporation-based therapies, Applied Physics Letters, 2012, 101, 083902, pp. 1-4.
Bagla, Papadouris, Percutaneous irreversible electroporation of surgically unresectable pancreatic cancer: A case report, J Vasc Interv Radiol, 2012, 23, pp. 142-145.
Bagla, S. and Papadouris, D., "Percutaneous Irreversible Electroporation of Surgically Unresectable Pancreatic Cancer: A Case Report" J. Vascular Int. Radiol. 23(1), 142-145 (2012).
Ball, et al, Irreversible electroporation: A new challenge in "out of the operating theater" anesthesia, Anesth Analg, May 2010, 110, pp. 1305-1309.
Bancroft, et al., Design of a Flow Perfusion Bioreactor System for Bone Tissue-Engineering Applications, Tissue Engineering, vol. 9, No. 3, 2003, p. 549-554.
Baptista et al., "The Use of Whole Organ Decellularization for the Generation of a Vascularized Liver Organoid," Heptatology, vol. 53, No. 2, pp. 604-617 (2011).
Bayazitoglu, et al., An overview of nanoparticle assisted laser therapy, International Journal of Heat and Mass Transfer, Sep. 11, 2013, 67, pp. 469-486.
Beebe, S.J., et al., "Diverse effects of nanosecond pulsed electric fields on cells and tissues", DNA and Cell Biology, 22(12): 785-796(2003).
Beebe, S.J., et al., Nanosecond pulsed electric field (nsPEF) effects on cells and tissues: apoptosis induction and tumor growth inhibition. PPPS—2001 Pulsed Power Plasma Science 2001, 28th IEEE International Conference on Plasma Science and 13th IEEE International Pulsed Power Conference, Digest of Technical Papers (Cat. No. 01CH37251). IEEE, Part vol. 1, 2001, pp. 211-215, vol. I, Piscataway, NJ, USA.
Beebe, S.J., et al.,, "Nanosecond, high-intensity pulsed electric fields induce apoptosis in human cells", FASEB J, (9): p. 1493-5 (2003).
Beitel-White, N., S. Bhonsle, R. Martin, and R. V. Davalos, "Electrical characterization of human biological tissue for irreversible electroporation treatments," in 2018 40th Annual International Conference of the IEEE Engineering in Medicine and Biology Society (EMBC). IEEE, 2018, pp. 4170-4173.

(56) References Cited

OTHER PUBLICATIONS

Belehradek, J., et al., "Electropermeabilization of Cells in Tissues Assessed by the Qualitative and Quantitative Electroloading of Bleomycin", Biochimica Et Biophysica Acta-Biomembranes, 1190(1): p. 155-163 (1994).
Ben-David, E. et al., "Irreversible Electroporation: Treatment Effect Is Susceptible to Local Environment and Tissue Properties," Radiology, vol. 269, No. 3, 2013, 738-747.
Ben-David, E., et al., "Characterization of Irreversible Electroporation Ablation in In Vivo Procine Liver" Am. Roentgenol. 198(1), W62-W68 (2012).
Benz, R., et al. "Reversible electrical breakdown of lipid bilayer membranes: a charge-pulse relaxation study". J Membr Biol, 48(2): p. 181-204 (1979).
Bertacchini, et al, Design of an irreversible electroporation system for clinical use, Technology in Cancer Research and Treatment, Aug. 2007, vol. 6, No. 4, pp. 313-320.
Bhonsle, S. et al., "Characterization of Irreversible Electroporation Ablation with a Validated Perfused Organ Model," J. Vasc. Interv. Radiol., vol. 27, No. 12, pp. 1913-1922.e2, 2016.
Bhonsle, S. P. et al., "Mitigation of impedance changes due to electroporation therapy using bursts of high-frequency bipolar pulses," Biomed. Eng. (NY)., vol. 14, No. Suppl 3, 14 pages, 2015.
Bhonsle, S., M. F. Lorenzo, A. Safaai-Jazi, and R. V. Davalos, "Characterization of nonlinearity and dispersion in tissue impedance during high-frequency electroporation," IEEE Transactions on Biomedical Engineering, vol. 65, No. 10, pp. 2190-2201, 2018.
Blad, et al., Impedance Spectra of Tumour Tissue in Comparison with Normal Tissue; a Possible Clinical Application for Electrical Impedance Tomography, Physiol. Meas. 17 (1996) A105-A115.
Bolland, F., et al., "Development and characterisation of a full-thickness acellular porcine bladder matrix for tissue engineering", Biomaterials, Elsevier Science Publishers, Barking, GB, vol. 28, No. 6, Nov. 28, 2006, pp. 1061-1070.
Bonakdar, M., E. L. Latouche, R. L. Mahajan, and R. V. Davalos, "The feasibility of a smart surgical probe for verification of IRE treatments using electrical impedance spectroscopy," IEEE Trans. Biomed. Eng., vol. 62, No. 11, pp. 2674-2684, 2015.
Bondarenko, A. and G. Ragoisha, Eis spectrum analyser (the program is available online at http://www.abc.chemistry.bsu.by/vi/analyser/.
Boone, et al, Review imaging with electricity: Report of the European concerted action on impedance tomography, Journal of Medical Engineering & Technology, Nov. 1997, vol. 21, No. 6, pp. 201-232.
Boone, K., Barber, D. & Brown, B. Review—Imaging with electricity: report of the European Concerted Action on Impedance Tomography. J. Med. Eng. Technol. 21, 201-232 (1997).
Boussetta, N., N. Grimi, N. I. Lebovka, and E. Vorobiev, "Cold" electroporation in potato tissue induced by pulsed electric field, Journal of food engineering, vol. 115, No. 2, pp. 232-236, 2013.
Bower et al., "Irreversible electroporation of the pancreas: definitive local therapy without systemic effects." Journal of surgical oncology, 2011. 104(1): p. 22-28.
BPH Management Strategies: Improving Patient Satisfaction, Urology Times, May 2001, vol. 29, Supplement 1. 22 pages.
Buist et al., "Efficacy of multi-electrode linear irreversible electroporation," Europace, vol. 23, No. 3, pp. 464-468, 2021, 5 pages.
Bulvik, B. E. et al. "Irreversible Electroporation versus Radiofrequency Ablation A Comparison of Local and Systemic Effects in a Small Animal Model," Radiology, vol. 280, No. 2, 2016, 413-424.
Butikofer, R. et al., "Electrocutaneous Nerve Stimulation-I: Model and Experiment," IEEE Trans. Biomed. Eng., vol. BME-25, No. 6, 526-531, 1978,6 pages.
Duraiswami, et al., Solution of Electrical Impedance Tomography Equations Using Boundary Element Methods, Boundary Element Technology XU, 1997, pp. 226-237.
Edd et al., "Mathematical modeling of irreversible electroporation for treatment planning." Technology in Cancer 20 Research and Treatment, vol. 6, No. 4, pp. 275-286 (2007).
Edd, et al, In vivo results of a new focal tissue ablation technique: Irreversible electroporation, IEEE Transactions on Biomedical Engineering, Jun. 2006, vol. 53, No. 5, pp. 1409-1415.
Edd, J., et al., In-Vivo Results of a New Focal Tissue Ablation Technique: Irreversible Electroporaton, IEEE Trans. 21 Biomed. Eng. 53 (2006) p. 1409-1415.
Edd, J.F, et al., 2007, "Mathematical modeling of irreversible electroporation fortreatment planning.", Technology in Cancer Research and Treatment, 6:275-286.
Ellis TL, Garcia PA, Rossmeisl JH, Jr., Henao-Guerrero N, Robertson J, et al., "Nonthermal irreversible electroporatior For intracranial surgical applications. Laboratory investigation", J Neurosurg 114: 681-688 (2011).
Eppich et al., "Pulsed electric fields for selection of hematopoietic cells and depletion of tumor cell contaminants." Nature Biotechnology 18, pp. 882-887 (2000).
Ermolina et al., "Study of normal and malignant white blood cells by time domain dielectric spectroscopy." IEEE Transactions on Dielectrics and Electrical Insulation, 8 (2001) pp. 253-261.
Esser, A.T., et al., "Towards solid tumor treatment by irreversible electroporation: intrinsic redistribution of fields and currents in tissue". Technol Cancer Res Treat, 6(4): p. 261-74 (2007).
Esser, A.T., et al., "Towards Solid Tumor Treatment by Nanosecond Pulsed Electric Fields", Technology in Cancer Research & Treatment, 8(4): p. 289-306 (2009).
Faroja, et al, Irreversible electroporation ablation: Is all the damage nonthermal?, Radiology, Feb. 2013, vol. 266, No. 2, pp. 462-470.
Faroja, M., et al., "Irreversible Electroporation Ablation: Is the entire Damage Nonthermal?", Radiology, 266(2), 28 462-470 (2013).
Fischbach, et al., Engineering tumors with 3D scaffolds, Nature Methods, Sep. 2, 2007, vol. 4, No. 10, pp. 855-860.
Flanagan et al., "Unique dielectric properties distinguish stem cells and their differentiated progeny." Stem Cells, vol. 26, pp. 656-665 (2008).
Fong et al., "Modeling Ewing sarcoma tumors in vitro with 3D scaffolds." Proceedings of the National Academy of Sciences vol. 110, pp. 6500-6505 (2013).
Fox, et al., Sampling Conductivity Images via MCMC, Mathematics Department, Auckland University, New Zealand, May 1997, 9 pages.
Frandsen, S. K., H. Gissel, P. Hojman, T. Tramm, J. Eriksen, and J. Gehl. Direct therapeutic applications of calcium electroporation to effectively induce tumor necrosis. Cancer Res. 72:1336-41,2012.
Freeman, S.A., et al., Theory of Electroporation of Planar Bilayer-Membranes—Predictions of the Aqueous Area, Change in Capacitance, and Pore-Pore Separation. Biophysical Journal, 67(1): p. 42-56 (1994).
Gabriel, C, Dielectric properties of biological tissue: variation with age. Bioelectromagnetics, 2005. Suppl 7: p. S12-8.
Garca-Sánchez, T., A. Azan, I. Leray, J. Rosell-Ferrer, R. Bragos, and L. M. Mir, "Interpulse multifrequency electrical Impedance measurements during electroporation of adherent differentiated myotubes," Bioelectrochemistry, vol. 105, pp. 123-135, 2015.
Garcia et al., "Irreversible electroporation (IRE) to treat brain cancer." ASME Summer Bioengineering Conference, Marco Island, FL, Jun. 25-29, 2008, 2 pages.
Garcia et al., "Towards a Predictive Model of Electroporation-Based Therapies using Pre-Pulse Electrical Measurements" Abstract presented in the IEEE Engineering in Medicine and Biology Conference in Aug. 28, 2012 in San Diego, California, 4 pages.
Garcia P.A., et al., "Pilot study of irreversible electroporation for intracranial surgery", Conf Proc IEEE Eng Med Biol Soc, 2009:6513-6516, 2009.
Garcia P.A., et al., "7.0-T Magnetic Resonance Imaging Characterization of Acute Blood-Brain-Barrier Disruption Achieved with Intracranial Irreversible Electroporation", PLOS One, Nov. 2012, 7:11, e50482.
Garcia, et al, A parametric study delineating irreversible electroporation from thermal damage based on a minimally invasive intracranial procedure, Biomedical Engineering Online, 2011, 10: 34, pp. 1-21.
Garcia, et al, Irreversible electroporation (IRE) to treat brain tumors, Proceedings of the ASME 2008 Summer Bioengineering Conference (SBC2008), Jun. 25, 2008, pp. 6-7.

(56) References Cited

OTHER PUBLICATIONS

Garcia, et al, Non-thermal irreversible electroporation (N-TIRE) and adjuvant fractionated radiotherapeutic multimodal therapy for intracranial malignant glioma in a canine patient, Feb. 2011, vol. 10, No. 1, pp. 73-83.

Garcia, et al, Non-thermal irreversible electroporation for deep intracranial disorders, 32nd Annual International Conference of the IEEE EMBS, IEEE, Aug. 2010, pp. 2747463.

Garcia, et al, Position paper concerning the use of Angiodynamics' nanoknife system for treatment of brain gliomas, Virgina Tech—Wake Forest University, May 22, 2013, pp. 1-46.

Garcia, et al., "A Parametric Study Delineating Irreversible Electroporation from Thermal Damage Based on a 40 Minimally Invasive Intracranial Procedure," Biomed Eng Online, vol. 10:34, 22 pp. 2011.

Garcia, P. A., et al., "Towards a predictive model of electroporation-based therapies using pre-pulse electrical 41 measurements," Conf Proc IEEE Eng Med Biol Soc, vol. 2012, pp. 2575-2578, 2012.

Garcia, P. A., et al., "Non-thermal Irreversible Electroporation (N-TIRE) and Adjuvant Fractioned Radiotherapeutic Multimodal Therapy for Intracranial Malignant Glioma in a Canine Patient" Technol. Cancer Res. Treatment 10(1), 73-83 (2011).

Garcia, P. A., et al., Intracranial Nonthermal Irreversible Electroporation: In Vivo Analysis. Journal of Membrane Biology, 2010. 236(1): p. 127-136.

Garcia, P.A., R.V. Davalos, and D. Miklavcic, A Numerical Investigation of the Electric and Thermal Cell Kill Distributions in Electroporation-Based Therapies in Tissue. Plos One, 2014. 9(8).

Garcia, Paulo A., Robert E. Neal II and Rafael V. Davalos, Chapter 3, Non-Thermal Irreversible Electroporation for Tissue Ablation, In: Electroporation in Laboratory and Clinical Investigations ISBN 978-1-61668-327-6 Editors: Enrico P. Spugnini and Alfonso Baldi, 2010,22 pages.

Gawad, S., T. Sun, N. G. Green, and H. Morgan, "Impedance spectroscopy using maximum length sequences: Application to single cell analysis," Review of Scientific Instruments, vol. 78, No. 5, p. 054301,2007.

Gehl, et al., In Vivo Electroporation of Skeletal Muscle: Threshold, Efficacy and Relation to Electric Field Distribution, Biochimica et Biphysica Acta 1428, 1999, pp. 233-240.

Gilbert, et al., Novel Electrode Designs for Electrochemotherapy, Biochimica et Biophysica Acta 1334, 1997, pp. 9-14.

Gilbert, T. W., et al., "Decellularization of tissues and organs", Biomaterials, Elsevier Science Publishers, Barking, GB, vol. 27, No. 19, Jul. 1, 2006, pp. 3675-3683.

Golberg, A. and Rubinsky, B., "A statistical model for multidimensional irreversible electroporation cell death in tissue." Biomed Eng Online, 9,13 pages, 2010.

Gothelf, et al., Electrochemotherapy: Results of Cancer Treatment Using Enhanced Delivery of Bleomycin by Electroporation, Cancer Treatment Reviews 2003: 29: 371-387.

Gowrishankar et al., An Approach to electrical modeling of single and multiple cells, Mar. 18, 2003, PNAS, vol. 100 No. 6, pp. 3203-3208.

Gowrishankar T.R., et al., "Microdosimetry for conventional and supra-electroporation in cells with organelles". Biochem Biophys Res Commun, 341(4): p. 1266-1276 (2006).

Granot, Y., A. Ivorra, E. Maor, and B. Rubinsky, "In vivo imaging of irreversible electroporation by means of electrical impedance tomography," Physics in Medicine & Biology, vol. 54, No. 16, p. 4927,2009.

Griffiths, Tissue Spectroscopy with Electrical Impedance Tomography: Computer Simulations, IEEE Transactions on Biomedical Engineering, vol. 42, No. 9, Sep. 1995. 8 pages.

Groen, M. H. A. et al., "In Vivo Analysis of the Origin and Characteristics of Gaseous Microemboli during Catheter-Mediated Irreversible Electroporation," Europace, 2021, 23(1), 139-146.

Guenther, E. et al., "Electrical breakdown in tissue electroporation," Biochem. Biophys. Res. Commun., vol. 467, No. 4, 736-741, Nov. 2015, 15 pages.

Gumerov, et al, The dipole approximation method and its coupling with the regular boundar yelement method for efficient electrical impedance tomography, BETECH Jun. 1999.

Gumerov, et al., The Dipole Approximation Method and Its Coupling with the Regular Boundary Element Method for Efficient Electrical Impedance Tomography, Boundary Element Technology XIII, 1999, 10 pp.

Guo, et al., Irreversible electroporation in the liver: Contrast-enhanced inversion-recovery MR images approaches to differentiate reversibly electroporated penumbra from irreversibly electroporated ablation zones, Radiology, Feb. 2011, vol. 258, No. 2, pp. 461-468.

Butikofer, R. et al., "Electrocutaneous Nerve Stimulation-II: Stimulus Waveform Selection," IEEE Trans. Biomed. Eng., vol. BME-26, No. 2, 69-75, 1979.

Cannon et al., "Safety and early efficacy of irreversible electroporation for hepatic tumors in proximity to vital structures." Journal of Surgical Oncology, 6 pages (2012).

Carmi, and Georgiades, Combination percutaneous and intraarterial therapy for the treatment of hepatocellular carcinoma: A review, Seminars in Interventional Radiology, 2010, vol. 27, No. 3, pp. 296-301.

Carpenter A.E. et al., "CellProfiler: image analysis software for identifying and quantifying cell phenotypes." Genome Biol. 2006; 7(10): R100. Published online Oct. 31, 2006, 11 pages.

Carson, et al., Improving patient satisfaction, BPH management strategies, Supplement to Urology Times, May 2001, Vo. 29, Suppl. 1, pp. 1-22.

Castellvi, Q., B. Mercadal, and A. Ivorra, "Assessment of electroporation by electrical impedance methods," in Handbook of electroporation. Springer-Verlag, 2016, pp. 671-690.

Cemazar M, Parkins CS, Holder AL, Chaplin DJ, Tozer GM, et al., "Electroporation of human microvascular endothelial cells: evidence for an anti-vascular mechanism of electrochemotherapy", Br J Cancer 84: 565-570 (2001).

Chandrasekar, et al., Transurethral Needle Ablation of the Prostate (TUNA)—a Propsective Study, Six Year Follow Up, (Abstract), Presented at 2001 National Meeting, Anaheim, CA, Jun. 5, 2001. 1 page.

Chang, D.C., "Cell Poration and Cell-Fusion Using an Oscillating Electric-Field". Biophysical Journal, 56(4): p. 641-652 (1989).

Charpentier, et al, Irreversible electroporation of the liver an dliver hilum in swine, HBP, 2011, 13, pp. 168-173.

Charpentier, K.P., et al., "Irreversible electroporation of the pancreas in swine: a pilot study." HPB: the official journal of the International Hepato Pancreato Biliary Association, 2010.12(5): p. 348-351.

Chen et al., "Classification of cell types using a microfluidic device for mechanical and electrical measurement on single cells." Lab on a Chip, vol. 11, pp. 3174-3181 (2011).

Chen, et al., Preclinical study of locoregional therapy of hepatocellular carcinoma by bioelectric ablation with microsecond pulsed electric fields (usPEFs), Scientific Reports, Apr. 2015, 5, 9851, pp. 1-10.

Chen, M.T., et al., "Two-dimensional nanosecond electric field mapping based on cell electropermeabilization", PMC Biophys, 2(1):9 (2009).

Choi, et al., Preclinical analysis of irreversible electroporation on rat liver tissues using a microfabricated electroporator, Tissue Engineering Part C, 2010, vol. 16, No. 6, pp. 1245-1253.

Clark et al., "The electrical properties of resting and secreting pancreas." The Journal of Physiology, vol. 189, pp. 247-260 (1967).

Corovic et al., "Analytical and numerical quantification and comparison of the local electric field in the tissue for different electrode configurations," Biomed Eng Online, 6, 14 pages, 2007.

Cosman, E. R. et al., "Electric and Thermal Field Effects in Tissue Around Radiofrequency Electrodes," Pain Med., vol. 6, No. 6, 405-424, 2005, 20 pages.

Cox, et al., Surgical Treatment of Atrial Fibrillation: A Review, Europace (2004) 5, S20-S-29.

Craiu, Scadden, Chapter 22 flow electroporation with pulsed electric fields for purging tumor cells, Electroporation Protocols: Preclinical and Clinical Gene Medicine, Methods in Molecular Biology, vol. 423, 2008, pp. 301-310.

(56) References Cited

OTHER PUBLICATIONS

Creason, S. C., J. W. Hayes, and D. E. Smith, "Fourier transform faradaic admittance measurements iii. comparison of measurement efficiency for various test signal waveforms," Journal of Electroanalytical chemistry and interfacial electrochemistry, vol. 47, No. 1, pp. 9-46, 1973.
Cukjati, et al., Real time electroporation control for accurate and safe in vivo non-viral gene therapy, Bioelectrochemistry, Nov. 10, 2006, 70, pp. 501-507.
Dahl et al., "Nuclear shape, mechanics, and mechanotransduction." Circulation Research vol. 102, pp. 1307-1318 (2008).
Daniels, Rubinsky, Electrical field and temperature model of nonthermal irreversible electroporation in heterogeneous tissues, Journal of Biomedical Engineering, Jul. 2009, vol. 131, 071006, pp. 1-12.
Daniels, Rubinsky, Temperature modulation of electric fields in biological matter, PLOS One, vol. 6, Iss. 6, e20877, pp. 1-9, Jun. 2011.
Daskalov, I., et al., "Exploring new instrumentation parameters for electrochemotherapy—Attacking tumors with bursts of biphasic pulses instead of single pulses", IEEE Eng Med Biol Mag, 18(1): p. 62-66 (1999).
Daud, A.I., et al., "Phase 1 Trial of Interleukin-12 Plasmid Electroporation in Patients With Metastatic Melanoma," Journal of Clinical Oncology, 26, 5896-5903, Dec. 20, 2008.
Davalos et al., "Electrical impedance tomography for imaging tissue electroporation," IEEE Transactions on Biomedical Engineering, 51, pp. 761-767, 2004.
Davalos, et al., A Feasibility Study for Electrical Impedance Tomography as a Means to Monitor Tissue Electroporation for Molecular Medicine, IEEE Transactions on Biomedical Engineering, vol. 49, No. 4, Apr. 2002, pp. 400-403.
Davalos, et al., Theoretical Analysis of the Thermal Effects During In Vivo Tissue Electroporation, Bioelectrochemistry, vol. 61, pp. 99-107, 2003.
Davalos, et al., Tissue Ablation with Irreversible Electroporation, Annals of Biomedical Engineering, vol. 33, No. 2, p. 223-231, Feb. 2005.
Davalos, R. V. & Rubinsky, B. Temperature considerations during irreversible electroporation. International Journal of Heat and Mass Transfer 51, 5617-5622, doi: 10.1016/j.ijheatmasstransfer.2008. 04.0 (2008).
Davalos, Real-Time Imaging for Molecular Medicine through Electrical Impedance Tomography of Electroporation, Dissertation for Ph.D. in Engineering-Mechanical Engineering, Graduate Division of University of California, Berkeley, 2002, pp. 1-237.
De Senneville, B. D. et al., "MR thermometry for monitoring tumor ablation," European radiology, vol. 17, No. 9, pp. 2401-2410, 2007.
De Vuyst, E., et al., "In situ bipolar Electroporation for localized cell loading with reporter dyes and investigating gap functional coupling", Biophysical Journal, 94(2): p. 469-479 (2008).
Dean, Nonviral Gene Transfer to Skeletal, Smooth, and Cardiac Muscle in Living Animals, Am J. Physiol Cell Physiol 289: 233-245, 2005.
Demirbas, M. F., "Thermal Energy Storage and Phase Change Materials: An Overview" Energy Sources Part B 1(1), 35-95 (2006).
Deodhar, et al, Irreversible electroporation near the heart: Ventricular arrhythmias can be prevented with ECG synchronization, AJR, Mar. 2011, 196, pp. W330-W335.
Deodhar, et al, Renal tissue ablation with irreversible electroporation: Preliminary results in a porcine model, Technology and Engineering, Urology, 2010, 1-7.
Dev, et al, Electric field of a six-needle array electrode used in drug and DNA delivery in vivo: Analytical versus numerical solution, IEEE Transactions on Biomedical Engineering, Nov. 2003, vol. 50, No. 11, pp. 1296-1300.
Dev, et al, Medical Applications of Electroporation, IEEE Transactions of Plasma Science, vol. 28, No. 1, p. 15 206-223, Feb. 2000.
Dev, et al, Sustained Local Delivery of Heparin to the Rabbit Arterial Wall with an Electroporation Catheter, Catheterization and Cardiovascular Diagnosis, Nov. 1998, vol. 45, No. 3, pp. 337-343.

Diederich, et al, Catheter-based ultrasound applicators for selective thermal ablation: progress towards MRI-guided applications in prostate, Int. J. Hyperthermia, Nov. 2004, vol. 20, No. 7, pp. 739-756.
du Pre, et al, Minimal coronary artery damage by myocardial electroporation ablation, European Society of Cardiology, Europace, May 31, 2012, pp. 1-6.
Duck, F. A., Physical Properties of Tissue: A Comprehensive Reference Book. London: Harcourt Brace Jovanovich, 1990, 358 pages.
Dunki-Jacobs, et al., Evaluation of resistance as a measure of successful tumor ablation during irreversible electroporation of the pancreas, American College of Surgeons, Feb. 2014, vol. 218, No. 2, pp. 179-187.
Dupuy, and Shulman, Current status of thermal ablation treatments for lung malignancies, Seminars in Interventional Radiology, 2010, vol. 27, No. 3, pp. 268-275.
Dupuy, et al, Irreversible electroporation in a swine lung model, Cardiovasc Intervent Radiol, Dec. 30, 2010, 34, pp. 391-395.
Duraiswami, et al., Boundary Element Techniques for Efficient 2-D and 3-D Electrical Impedance Tomography, Chemical Engineering Science, vol. 52, No. 13, pp. 2185-2196, 1997.
Duraiswami, et al., Efficient 2D and 3D Electrical Impedance Tomography Using Dual Reciprocity Boundary Element Techniques, Engineering Analysis with Boundary Elements 22, (1998) 13-31.
Neal II et al., "A Case Report on the Successful Treatment of a Large Soft-Tissue Sarcoma with Irreversible Electroporation," Journal of Clinical Oncology, 29, pp. 1-6, 2011.
Mercadal, Borja et al. "Dynamics of Cell Death After Conventional IRE and H-FIRE Treatments", Annals of Biomedical Engineering, vol. 48, No. 5, 2020, p. 1451-1462.
Miklavcic, et al., The Importance of Electric Field Distribution for Effective in Vivo Electroporation of Tissues, Biophysical Journal, vol. 74, May 1998, pp. 2152-2158.
Miklavció, D. et al., "The effect of high frequency electric pulses on muscle contractions and antitumor efficiency in vivo for a potential use in clinical electrochemotherapy," Bioelectrochemistry, vol. 65, 121-128, 2004, 8 pages.
Miller, L., et al., Cancer cells ablation with irreversible electroporation, Technology in Cancer Research and Treatment 4 (2005) 699-706.
Min, M., A. Giannitsis, R. Land, B. Cahill, U. Pliquett, T. Nacke, D. Frense, G. Gastrock, and D. Beckmann, Comparison of rectangular wave excitations in broad band impedance spectroscopy for microfluidic applications, in World Congress on Medical Physics and Biomedical Engineering, Sep. 7-12, 2009, Munich, Germany. Springer, 2009, pp. 85-88.
Min, M., U. Pliquett, T. Nacke, A. Barthel, P. Annus, and R. Land, "Broadband excitation for short-time impedance spectroscopy," Physiological measurement, vol. 29, No. 6, p. S185,2008.
Mir et al., "Mechanisms of Electrochemotherapy" Advanced Drug Delivery Reviews 35:107-118 (1999).
Mir et al., British Journal of Cancer, 77(12):2336-2342 (1998).
Mir, Chapter 1 application of electroporation gene therapy: Past, current and future, Electroporation Protocols: Preclinical and Clinical Gene Medicine, Methods in Molecular Biology, vol. 423, 2008, pp. 3-17.
Mir, et al., Effective Treatment of Cutaneous and Subcutaneous Malignant Tumours by Electrochemotherapy, British Journal of Cancer, vol. 77, No. 12, pp. 2336-2342, 1998.
Mir, L.M. and Orlowski, S., "The basis of electrochemotherapy," Electrochemotherapy, Electrogenetherapy, and Transdermal Drug Delivery: Electrically Mediated Delivery of Molecules to Cells, M.J. Jaroszeski, R. Heller, R. Gilbert, Editors, Humana Press, Totowa, New Jersey p. 99-118 (2000).
Mir, L.M., et al., Electric Pulse-Mediated Gene Delivery to Various Animal Tissues, in Advances in Genetics, 'Academic Press, 2005, p. 83-114.
Mir, Orlowski, Introduction: Electropermeabilization as a new drug delivery approach, Methods in Molecular Medicine, 2000, vol. 37, pp. 99-117.

(56) References Cited

OTHER PUBLICATIONS

Mir, Therapeutic Perspectives of In Vivo Cell Electropermeabilization, Bioelectrochemistry, vol. 53, pp. 1-10, 2000.
Miklavcic, et al., A Validated Model of an in Vivo Electric Field Distribution in Tissues for Electrochemotherapy and For DNA Electrotransfer for Gene Therapy, Biochimica et Biophysica Acta 1523 (2000), pp. 73-83.
Mulhall et al., "Cancer, pre-cancer and normal oral cells distinguished by dielectrophoresis." Analytical and Bioanalytical Chemistry, vol. 401, pp. 2455-2463 (2011).
Naslund, Cost-Effectiveness of Minimally Invasive Treatments and Transurethral Resection (TURP) in Benign Prostatic Hyperplasia (BPH), (Abstract), Presented at 2001 AUA National Meeting,, Anaheim, CA, Jun. 5, 2001. 1 page.
Naslund, Cost-effectiveness of minimally invasive treatments and transurethral resection (TURP) in benign prostatic hyperplasia (BPH), Unveristy of Maryland School of Medicine, 2001, pp. 1213.
Naslund, Michael J., Transurethral Needle Ablation of the Prostate, Urology, vol. 50, No. 2, Aug. 1997, 6 pages.
Nath, S., Dimarco, J. P. and Haines, D. E. (1994), Basic Aspects of Radiofrequency Catheter Ablation. Journal of Cardiovascular Electrophysiology, 5: 863-876.
Neal II, et al., Experimental characterization and numerical modeling of tissue electrical conductivity during pulsed electric fields for irreversible electroporation treatment planning, IEEE Transactions on Biomedical Engineering, Apr. 2012, vol. 59, No. 4, pp. 1076-1085.
Neal II, et al., Successful treatment of a large soft tissue sarcoma with irreversible electroporaiton, Journal of Clinical Oncology, May 1, 2011, vol. 29, No. 13, pp. e372-e377.
Neal II, R. E. et al. In Vitro and Numerical Support for Combinatorial Irreversible Electroporation and Electrochemotherapy Glioma Treatment. Annals of Biomedical Engineering, Oct. 29, 2013, 13 pages.
Neal II, R. E., et al., "Successful Treatment of a Large Soft Tissue Sarcoma with Irreversible Electroporation", Journal of Clinical Oncology, 29:13, e372-e377 (2011).
Neal II, R.E., et al., "Treatment of breast cancer through the application of irreversible electroporation using a novel minimally invasive single needle electrode." Breast Cancer Research and Treatment, 2010. 123(1): p. 295-301.
Neal II, Robert E. and R.V. Davalos, The Feasibility of Irreversible Electroporation for the Treatment of Breast Cancer and Other Heterogeneous Systems, Ann Biomed Eng, 2009, 37(12): p. 2615-2625.
Neal II et al., "Experimental Characterization and Numerical Modeling of Tissue Electrical Conductivity during Pulsed Electric Fields for Irreversible Electroporation Treatment Planning," Biomedical Engineering, IEEE Transactions on Biomedical Engineering, vol. 59, pp. 1076-1085, 2012.
Neal RE II, et al. (2013) Improved Local and Systemic Anti-Tumor Efficacy for Irreversible Electroporation in Immunocompetent versus Immunodeficient Mice. Plos One 8(5): e64559. https://doi.org/10.1371/journal. pone.0064559.
Neal, Davalos, The feasibility of irreversible electroporation for the treatment of breast cancer and other heterogeneous systems, Annals of Biomedical Engineering, Dec. 2009, vol. 37, No. 12, pp. 2615-2625.
Neal, et al, A study using irreversible electroporation to treat large, irregular tumors in a canine patient, 32nd Annual International Conference of the IEEE EMBS, IEEE, Aug. 2010, pp. 2747-2750.
Neal, et al, An "Off-the-Shelf" system for intraprocedural electrical current evaluation and monitoring of irreversible electroporation therapy, Cardiovasc Intervent Radiol, Feb. 27, 2014. 6 pages.
Nesin et al., "Manipulation of cell vol. and membrane pore comparison following single cell permeabilization with 60- and 600-ns electric pulses." Biochimica et Biophysica Acta (BBA)-Biomembranes, vol. 1808, pp. 792-801 (2011).
Neu, and Neu, Mechanism of irreversible electroporation in cells: Insight from the models, Irreversible Electroporation: BIOMED, pp. 85-122.
Neven et al., Epicardial Linear Electroporation Ablation and Lesion Size, Department of Cardiology, University of Medical Utrecht, Aug. 2014, vol. 11, No. 8.
Nikolova, B., et al., "Treatment of Melanoma by Electroporation of Bacillus Calmette-Guerin". Biotechnology & Biotechnological Equipment, 25(3): p. 2522-2524 (2011).
Nikolski, et al., Electroporation of the heart, Europace, 2005, 7, pp. S146-S154.
Nuccitelli, R., et al., "A new pulsed electric field therapy for melanoma disrupts the tumor's blood supply and causes complete remission without recurrence", Int J Cancer, 125(2): p. 438-45 (2009).
O'Brien, T. J. et al., "Effects of internal electrode cooling on irreversible electroporation using a perfused organ Model," Int. J. Hyperth., vol. 35, No. 1, pp. 44-55, 2018.
O'Brien et al., "Investigation of the Alamar Blue (resazurin) fluorescent dye for the assessment of mammalian cell cytotoxicity." European Journal of Biochemistry, vol. 267, pp. 5421-5426 (2000).
Ohio Environmental Protection Agency, Ground Water Flow and Fate and Transport Modeling, State of Ohio Environmental Protection Agency, 2007, pp. 14-1-14-32.
Onik, and Rubinsky, Irreversible electroporation: First patient experience focal therapy of prostate cancer, Irreversible Electroporation, BIOMED, pp. 235-247.
Onik, et al., Irreversible electroporation: Implications for prostate ablation, Technology in Cancer Research and Treatment, Aug. 2007, vol. 6, No. 4, pp. 295-300.
Onik, G. and B. Rubinsky, eds. "Irreversible Electroporation: First Patient Experience Focal Therapy of Prostate Cancer. Irreversible Electroporation", ed. B. Rubinsky 2010, Springer Berlin Heidelberg, pp. 235-247.
Onik, G.,P. Mikus, and B. Rubinsky, "Irreversible electroporation: implications for prostate ablation." Technol Cancer Res Treat, 2007. 6(4): p. 295-300.
Ott, H. C., et al., "Perfusion-decellularized matrix: using nature's platform to engineer a bioartificial heart", Nature Medicine, Nature Publishing Group, New York, NY, US, vol. 14, No. 2, Feb. 1, 2008, pp. 213-221.
Pakhomova, O. N., Gregory, B., Semenov I., and Pakhomov, A. G., BBA—Biomembr., 2014, 1838, 2547-2554.
Partridge, B. R. et al., "High-Frequency Irreversible Electroporation for treatment of Primary Liver Cancer: A Proof-of-Principle Study in Canine Hepatocellular Carcinoma," J. Vasc. Interv. Radiol, vol. 31, No. 3, 482-491.e4, Mar. 2020, 19 pages.
Paszek et al., "Tensional homeostasis and the malignant phenotype." Cancer Cell, vol. 8, pp. 241-254 (2005).
Pavseij, N. et al. The course of tissue permeabilization studied on a mathematical model of a subcutaneous tumor in small animals. IEEE Trans Biomed Eng 52, 1373-1381 (2005).
Saldanha, et al, Current tumor ablation technologies: Basic science and device review, Seminars in Interventional Radiology, 2010, vol. 27, No. 3, pp. 247-254.
Salmanzadeh et al, "Dielectrophoretic differentiation of mouse ovarian surface epithelial cells, macrophages, and fibroblasts using contactless dielectrophoresis." Biomicrofluidics, vol. 6, 13 Pages (2012).
Salmanzadeh et al., "Investigating dielectric properties of different stages of syngeneic murine ovarian cancer cells" Biomicrofiuidics 7, 011809 (2013), 12 pages.
Salmanzadeh et al., "Sphingolipid Metabolites Modulate Dielectric Characteristics of Cells in a Mouse Ovarian Cancer Progression Model." Integr. Biol., 5(6), pp. 843-852 (2013).
Sanchez, B., G. Vandersteen, R. Bragos, and J. Schoukens, "Basics of broadband impedance spectroscopy measurements using periodic excitations," Measurement Science and Technology, vol. 23, No. 10, p. 105501, 2012.
Sanchez, B., G. Vandersteen, R. Bragos, and J. Schoukens, "Optimal multisine excitation design for broadband electrical impedance spectroscopy," Measurement Science and Technology, vol. 22, No. 11, p. 115601, 2011.

(56) References Cited

OTHER PUBLICATIONS

Sanders, et al., Nanosecond pulse generator with scalable pulse amplitude, IEEE, 2008, pp. 65-68.

Sankaranarayanan, et al., Effect of irreversible electroporation on cell proliferation in fibroblasts, Proc. ESA Annual Meeting on Electrostatics, 2011, pp. 1-8.

Sano et al., "Contactless Dielectrophoretic Spectroscopy: Examination of the Dielectric Properties of Cells Found in Blood." Electrophoresis, 32, pp. 3164-3171, 2011.

Sano et al., "In-vitro bipolar nano- and microsecond electro-pulse bursts for irreversible electroporation therapies." Bioelectrochemistry vol. 100, pp. 69-79 (2014).

Sano et al., "Modeling and Development of a Low Frequency Contactless Dielectrophoresis (cDEP) Platform to Sort cancer Cells from Dilute Whole Blood Samples." Biosensors & Bioelectronics, 8 pages (2011).

Sano, et al, Towards the creation of decellularized organ constructs using irreversible electroporation and active mechanical perfusion, Biomedical Engineering Online, 2010, 9, 83, pp. 1-16.

Sano, M. B. et al., "Burst and continuous high frequency irreversible electroporation protocols evaluated in a 3D tumor model," Phys. Med. Biol., vol. 63, No. 13, 2018, 17 pages.

Sano, M. B. et al., "Reduction of Muscle Contractions During Irreversible Electroporation Therapy Using High-Frequency Bursts of Alternating Polarity Pulses: A Laboratory Investigation in an Ex Vivo Swine Model," J. Vasc. Interv. Radiol., vol. 29, No. 6, 893-898.e4, Jun. 2018, 18 pages.

Saur et al., "CXCR4 expression increases liver and lung metastasis in a mouse model of pancreatic cancer." Gastroenterology, vol. 129, pp. 1237-1250 (2005).

Savader, et al."Treatment of Hemodialysis Catheter-associated Fibrin Sheaths by rt-PA Infusion: Critical Analysis of 124 Procedures," J Vasc Intery Radiol 2001; 12:711-715.

Schmukler, Impedance Spectroscopy of Biological Cells, Engineering in Medicine and Biology Society, Engineering Advances: New Opportunities for Biomedical Engineers, Proceedings of the 16th Annual Internal Conference of the IEEE, vol. 1, p. A74, downloaded from IEEE Xplore website, 1994.

Schoenbach et al., "Intracellular effect of ultrashort electrical pulses." Bioelectromagnetics, 22 (2001) pp. 440-448.

Schoenbach, et al, Bioelectric effects of intense nanosecond pulses, IEEE Transactions on Dielectric and Electrical Insulation, 2007, vol. 14, Iss. 5, pp. 1088-1109.

Seidler et al., "A Cre-loxP-based mouse model for conditional somatic gene expression and knockdown in vivo by using avian retroviral vectors." Proceedings of the National Academy of Sciences, vol. 105, p. 10137-10142 (2008).

Sel, D. et al. Sequential finite element model of tissue electropermeabilization. IEEE Transactions on Biomedical Engineering 52, 816-827, doi: 10.1109/tbme.2005.845212 (2005).

Sel, D., Lebar, A. M. & Miklavcic, D. Feasibility of employing model-based optimization of pulse amplitude and electrode distance for effective tumor electropermeabilization. IEEE Trans Biomed Eng 54, 773-781 (2007).

Sersa, et al, Tumor blood flow modifying effect of electrochemotherapy with Bleomycin, Anticancer Research, 1999, 19, pp. 4017-4022.

Sersa, et al., Reduced Blood Flow and Oxygenation in SA-1 Tumours after Electrochemotherapy with Cisplatin, British Journal of Cancer, 87, 1047-1054, 2002.

Sersa, et al., Tumour Blood Flow Modifying Effects of Electrochemotherapy: a Potential Vascular Targeted Mechanism, Radiol. Oncol., 37(1): 43-8, 2003.

Shafiee, et al, A preliminary study to delineate irreversible electroporation from thermal damage using the Arrhenius equation, Journal of Biomedical Engineering, Jul. 2009, vol. 131, 074509, pp. 1-5.

Shao, Qi et al. Engineering T cell response to cancer antigens by choice of focal therapeutic conditions, International Journal of Hyperthermia, 2019, DOI: 10.1080/02656736.2018.1539253. 10 pages.

Sharma, A. et al., "Review on Thermal Energy Storage with Phase Change Materials and Applications", Renewable Sustainable Energy Rev. 13(2), 318-345 (2009).

Sharma, et al., Poloxamer 188 Decreases Susceptibility of Artificial Lipid Membranes to Electroporation, Biophysical Journal, vol. 71, No. 6, pp. 3229-3241, Dec. 1996.

Soden, et al, Successful application of targeted electrochemotherapy using novel flexible electrodes and low dose bleomycin to solid tumors, Cancer Letters, 2006, 232 pp. 300-310.

Son, et al, Basic features of a cell electroporation model: illustrative behavior for tw overy different pulses, J Membrane Biol, Jul. 22, 2014, 247, pp. 1209-1228.

Song, Z.Q., et al., Mechanisms for steep pulse irreversible electroporation technology to kill human large cell lung cancer cells L9981. International Journal of Clinical and Experimental Medicine, 2014. 7(8): p. 2386-2394.

Szot et al., "3D in vitro bioengineered tumors based on collagen I hydrogels." Biomaterials vol. 32, pp. 7905-7912 (2011).

Talele, S. and P. Gaynor, "Non-linear time domain model of electropermeabilization: Effect of extracellular conductivity and applied electric field parameters", Journal of Electrostatics, 66(5-6): p. 328-334 (2008).

Talele, S. and P. Gaynor, "Non-linear time domain model of electropermeabilization: Response of a single cell to an arbitrary applied electric field", Journal of Electrostatics, 65(12): p. 775-784 (2007).

Talele, S., et al., "Modelling single cell electroporation with bipolar pulse parameters and dynamic pore radii". Journal of Electrostatics, 68(3): p. 261-274 (2010).

Teissie, J. and T.Y. Tsong, "Electric-Field Induced Transient Pores in Phospholipid-Bilayer Vesicles". Biochemistry, 20(6): p. 1548-1554 (1981).

Thompson, et al., To determine whether the temperature of 2% lignocaine gel affects the initial discomfort which may be associated with its instillation into the male urethra, BJU International (1999), 84, 1035-1037.

Thomson et al., "Investigation of the safety of irreversible electroporation in humans," J Vasc Interv Radiol, 22, pp. 611-621, 2011.

Thomson, Human experience with irreversible electroporation, Irreversible Electroporation, BIOMED, 2010, pp. 249-354.

Thomson, K. R., et al., "Investigation of the Safety of Irreversible Electroporation in Humans" J. Vascular Int. Radiol. 22 (5), 611-621 (2011).

Tibbitt et al., "Hydrogels as Extracellular Matrix Mimics for 3D Cell Culture", Jul. 2009, Biotechnol Bioeng, 103 (4),655-663.

Tijink, et al, How we do it: Chemo-electroporation in the head and neck for otherwise untreatable patients, Correspondence, Clinical Otolaryngology, 2006, 31, pp. 447-451.

Tracy, et al, Irreversible electroporation (IRE): A novel method for renal tissue ablation, BJU International, 107, pp. 1982-1987.

Trimmer, et al, Minimally invasive percutaneous treatment of small renal tumors with irreversible electroporation: a single-center experience, J Vasc Intery Radiol, 2015, 26: pp. 1465-1471.

Troszak, et al., Self-powered electroporation using a singularity-induced nano-electroporation configuration, Biochemical and Biophysical Research Communications, Sep. 28, 2011, 414, pp. 419-424.

Tsivian, Polascik, Recent advances in focal therapy of prostate and kidney cancer, Medicine Reports, Jan. 18, 2010, 2, 1, pp. 1-3.

TUNA—Suggested Local Anesthesia Guidelines, no date available. 1 page.

Valdez, C. M. et al., "The interphase interval within a bipolar nanosecond electric pulse modulates bipolar cancellation," Bioelectromagnetics, vol. 39, No. 6, 441-450, 2018, 28 pages.

Van Den Bos, W. et al., "MRI and contrast-enhanced ultrasound imaging for evaluation offocal irreversible electroporation treatment: results from a phase i-ii study in patients undergoing ire followed by radical prostatectomy," European radiology, vol. 26, No. 7, pp. 2252-2260, 2016.

Kotnik, T., et al., "Cell membrane electropermeabilization by symmetrical bipolar rectangular pulses. Part II. Reduced electrolytic contamination", Bioelectrochemistry, 54(1): p. 91-5 (2001).

(56) References Cited

OTHER PUBLICATIONS

Kotnik, T., et al., "Cell membrane electropermeabilization by symmetrical bipolar rectangular pulses". Part I. Increased efficiency of permeabilization. Bioelectrochemistry, 54(1): p. 83-90 (2001).
Kotnik, T., et al., "Role of pulse shape in cell membrane electropermeabilization", Biochimica Et Biophysica Acta-Biomembranes, 1614(2): p. 193-200 (2003).
Kranjc, M., S. Kranjc, F. Bajd, G. Sersa, I. Sersa, and D. Miklavcic, "Predicting irreversible electroporation-induced tissue damage by means of magnetic resonance electrical impedance tomography," Scientific reports, vol. 7, No. 1, pp. 1-10, 2017.
Kroeger, et al, Curvature-driven pore growth in charged membranes during charge-pulse and voltage-clamp experiments, Biophysical Journal, Feb. 2009, 96, 3, pp. 907-916.
Kurup, Callstrom, Image-guided percutaneous ablation of bone and soft tissue tumors, Seminars in Interventional Radiology, 2010, vol. 27, No. 3, pp. 276-284.
Labeed et al., "Differences in the biophysical properties of membrane and cytoplasm of apoptotic cells revealed using dielectrophoresis." Biochimica et Biophysica Acta (BBA)-General Subjects, vol. 1760, pp. 922-929 (2006).
Lackovic, I., et al., "Three-dimensional Finite-element Analysis of Joule Heating in Electrochemotherapy and in vivo Gene Electrotransfer", Ieee Transactions on Dielectrics and Electrical Insulation, 16(5): p. 1338-1347 (2009).
Latouche, E. L., M. B. Sano, M. F. Lorenzo, R. V. Davalos, and R. C. G. Martin, "Irreversible electroporation for the ablation of pancreatic malignancies: A patient-specific methodology," J. Surg. Oncol., vol. 115, No. 6, pp. 711-717, 2017.
Laufer et al., "Electrical impedance characterization of normal and cancerous human hepatic tissue." Physiological Measurement, vol. 31, pp. 995-1009 (2010).
Lavee, et al., "A Novel Nonthermal Energy Source for Surgical Epicardial Atrial Ablation: Irreversible Electroporation," The Heart Surgery Forum #2006-1201, vol. 10 (2): 96-101 (2007).
Lebar et al., "Inter-pulse interval between rectangular voltage pulses affects electroporation threshold of artificial lipid bilayers." IEEE Transactions on Nano Bioscience, vol. 1 (2002) pp. 116-120.
Lee, Cassinian Oval, Nov. 2004, Mathematics Department of The University of California at Irvine, pp. 1-5.
Lee, E. W. et al. Advanced Hepatic Ablation Technique for Creating Complete Cell Death : Irreversible Electroporation. Radiology 255, 426-433, doi:10.1148/radiol. 10090337 (2010).
Lee, E.W., et al., "Imaging guided percutaneous irreversible electroporation: ultrasound and immunohistological correlation", Technol Cancer Res Treat 6: 287-294 (2007).
Lee, et al, Imaging guided percutaneous irreversible electroporation: Ultrasound and immunohistological correlation, Technology in Cancer Research and Treatment, Aug. 2007, vol. 6, No. 4, pp. 287-293.
Lee, et al, Irreversible electroporation: A novel image-guided cancer therapy, Gut and Liver, Sep. 2010, vol. 4, Supp. 1, pp. S99-S104.
Lee, R. C., D. J. Canaday, and S. M. Hammer. Transient and stable ionic permeabilization of isolated skeletal muscle cells after electrical shock. J. Burn Care Rehabil. 14:528- 540, 1993.
Li, et al, The effects of irreversible electroporation (IRE) on nerves, PLOS One, Apr. 14, 2011, vol. 6, Iss. 4, e18831, pp. 1-7.
Li, W., et al., "The Effects of Irreversible Electroporation (IRE) on Nerves" PloS One, Apr. 2011, 6(4), e18831. 7 pages.
Lin, et al., An optically induced cell lysis device using dielectrophoresis, Applied Physics Letters, Jan. 20, 2009, 94, 033901, pp. 1-3.
Lion, et al., Poly(I:C) enhances the susceptibility of leukemic cells to NK cell cytotoxicity and phagocytosis by DC, PLOS One, vol. 6, Iss. 6, e20952, pp. 1-10, Jun. 17, 2011.
Lu, et al, Irreversible electroporation: Ready for prime time?, Techniques in Vascular and Interventional Radiology, 2013, 16, pp. 277-286.
Lundqvist, et al., Altering the Biochemical State of Individual Cultured Cells and Organelles with Ultramicroelectrodes, Proc. Natl. Acad. Sci. USA, vol. 95, pp. 10356-10360, Sep. 1998.
Lurquin, Gene Transfer by Electroporation, Molecular Biotechnology, vol. 7, 1997. 27 pages.
M. Marty et al., "Electrochemotherapy—An easy, highly effective and safe treatment of cutaneous and subcutaneous metastases: Results of ESOPE (European Standard Operating Procedures of Electrochemotherapy) study," European Journal of Cancer Supplements, 4, pp. 3-13, 2006.
Macek Lebar and Miklavcic, "Cell electropermeabilization to small molecules in vitro: control by pulse parameters." Radiology and Oncology, vol. 35(3), pp. 193-202 (2001).
Machado-Aranda, et al, Gene transfer of the Na+, K+K—ATPase B1 subunit using electroporation increases lung liquid clearance, American Journal of Respiratory and Critical Care Medicine, 2004, vol. 171, pp. 204-211.
Macherey, O. et al., "Asymmetric pulses in cochlear implants: Effects of pulse shape, polarity, and rate," JARO—J. Assoc. Res. Otolaryngol., vol. 7, No. 3, 253-266, 2006, 14 pages.
Mahmood, F., et al., "Diffusion-Weighted MRI for Verification of Electroporation-Based Treatments", Journal of Membrane Biology 240: 131-138 (2011).
Mahmood, Gehl, Optimizing clinical performance and geometrical robustness of a new electrode device for ntracranial tumor electroporation, Bioelectrochemistry, Jan. 6, 2011, 81, pp. 10-16.
Mahnic-Kalamiza, et al., "Educational application for visualization and analysis of electric field strength in multiple electrode electroporation," BMC Med Educ, vol. 12:102,13 pages, 2012.
Mali, et al., "The Effect of Electroporation Pulses on Functioning of the Heart," Med Biol Eng Comput (2008) 46:745-757.
Malpica et al., "Grading ovarian serous carcinoma using a two-tier system." The American Journal of Surgical Pathology, vol. 28, pp. 496-504 (2004).
Maor et al., The Effect of Irreversible Electroporation on Blood Vessels, Tech. in Cancer Res. and Treatment, vol. 6, No. 4, Aug. 2007, pp. 307-312.
Maor, et al, Intravascular irreversible electroporation: Theoretical and experimental feasibility study, 30th Annual International IEEE EMBS Conference, IEEE, Aug. 20, 2008, pp. 2051-2054.
Maor, et al, Irreversible electroporation attenuates neointimal formation after angioplasty, IEEE Transactions on Biomedical Engineering, Sep. 2008, vol. 55, No. 9, pp. 2268-2274.
Maor, et al, Non thermal irreversible electroporation: Novel technology for vascular smooth muscle cells abation, PLOS One, Mar. 9, 2009, vol. 4757-, Iss. 3, e4757, pp. 1-9.
Maor, Rubinsky, Endovascular nonthermal irreversible electroporation: A finite element analysis, Journal of Biomedical Engineering, Feb. 7, 2010, vol. 132, 031008, pp. 1-7.
Martin et al., "Gene Transfer to Intact Mesenteric Arteries by Electroporation" Journal of Vascular Research, 37:372-380 (2000).
Martin, n.R.C.G., et al., "Irreversible electroporation therapy in the management of locally advanced pancreatic adenocarcinoma." Journal of the American College of Surgeons, 2012.215(3): p. 361-369.
Martinsen, O. G. and Grimnes, S., Bioimpedance and bioelectricity basics. Academic press, 2011.
Maybody, An Overview of Image-Guided Percutaneous Ablation of Renal Tumors, Seminars in Interventional Radiology/vol. 27, No. 3, 2010, pp. 261-267.
Mazurek, et al, Effect of Short HV Pulses in Bacteria and Fungi, 1995, vol. 2, No. 3, pp. 418-425.
McCall, Nanoknife, liposomal doxorubicin show efficacy against liver cancer, European Congress of Radiology, Mar. 1, 2011, pp. 1-2.
McCarley, and Soulen, Percutaneous ablation of hepatic tumors, Seminars in Interventional Radiology, 2010, vol. 27, No. 3, pp. 255-260.
McIntyre, C. C. et al., "Modeling the excitability of mammalian nerve fibers: Influence of afterpotentials on the recovery cycle," J. Neurophysiol., vol. 87, No. 2, 995-1006, 2002, 12 pages.
McNeal, D. R., "Analysis of a Model for Excitation of Myelinated Nerve," IEEE Trans. Biomed. Eng., vol. BME-23, No. 4 329-337, 1976, 9 pages.
McWilliams, et al., Image-guided tumor ablation: Emerging technologies and future directions, Seminars in Interventional Radiology, 2010, vol. 27, No. 3, pp. 302-313.

(56) References Cited

OTHER PUBLICATIONS

Mercadal, B. et al., "Avoiding nerve stimulation in irreversible electroporation: A numerical modeling study," Phys. Med. Biol., vol. 62, No. 20, 8060-8079, 2017, 28 pages.

Lv, Y. et al. "The Englargement of Ablation Area by Electrolytic Irreversible Electroporation (E-IRE) Using Pulsed Field with Bias DC Field", Annals of Biomedical Engineering, vol. 50, No. 12, Dec. 2022, 10 pages.

\* cited by examiner

SYSTEM AND METHOD FOR ABLATING A TISSUE SITE BY ELECTROPORATION WITH REAL-TIME PULSE MONITORING

CROSS REFERENCE TO RELATED APPLICATIONS

This application claims the benefit of priority from U.S. Provisional Application No. 62/042,862, filed Aug. 28, 2014, and U.S. Provisional Application No. 62/173,538, filed Jun. 10, 2015, both of which are incorporated by reference herein.

FIELD OF THE INVENTION

The present invention relates to a control system for controlling an electroporation medical treatment device and more particularly, to such devices with real-time monitoring of pulse delivery during an electroporation treatment procedure.

BACKGROUND OF THE INVENTION

Medical devices for delivering therapeutic energy such as electrical pulses to tissue include one or more electrodes and a pulse generator. The pulse generator allows the electrode to deliver the therapeutic energy to a targeted tissue, thereby causing ablation of the tissue.

Electroporation procedure parameters that influence the size and shape of their affected region include the nature of the tissue (cellularity, extracellular constituent composition, anisotropy, conductivity, metabolic demand), the pulse delivery apparatus (number of electrodes, their size, and relative geometry), and pulse parameters (voltage, number of pulses, pulse length, pulse delivery rate). In addition to the above, the generator's maximum pulse intensity capabilities (maximum voltage and current) dictate the maximum achievable treatment region. Where controllable and large lesions are desired, it is important to maintain pulses that are capable of inducing electroporation effects to the tissue while remaining below the maximum generator capacity.

In conventional electroporation devices, before the treatment procedure a physician would decide on a particular pulse delivery apparatus and select the pulse parameters. Once the treatment procedure starts, the electroporation device follows the pre-treatment programming set by the physician and delivers the pulses according to the pre-selected pulse parameters. Specifically, there was no way to alter the settings other than to stop the procedure manually. Even when the procedure completes normally, there was no assurance that there were clinically sufficient electroporation of the targeted region due to the unpredictable nature of patient environments and living tissue.

Moreover, under certain conditions, the electroporation device can produce an unwanted spark across the electrodes, which causes the pulse generator to freeze or shut down prematurely. As a result, the treatment procedure would have to be restarted from the beginning.

Therefore, it would be desirable to provide a system and method for monitoring the electroporation pulse delivery in real-time and to alter the treatment parameters based on the monitoring as the treatment progresses and without the necessity to repeat the entire procedure.

SUMMARY OF THE DISCLOSURE

According to one aspect of the present invention, a medical system for ablating a tissue site by electroporation with real-time pulse monitoring during an electroporation treatment procedure is provided. The system includes electrodes, a pulse generator and a treatment control module. The pulse generator is configured to generate and apply between the electrodes multiple electroporation pulses according to selected pulse parameters for ablation of tissue in the target region. The treatment control module detects an abnormal condition of the applied electrical pulses in real-time during an electroporation treatment procedure and temporarily pauses the procedure without termination when the abnormal condition is detected. The abnormal condition indicates that a predetermined current threshold value is about to be exceeded or an ineffective electroporation of the tissue. Advantageously, the pause allows a physician to adjust the pulse parameters so as to complete the procedure without starting the procedure over again.

According to another aspect of the present invention, a method of ablating a tissue site by electroporation with real-time pulse monitoring during an electroporation treatment procedure is provided.

In an electroporation treatment procedure, at least two electrodes are positioned near a target region of a tissue site of a patient and multiple electroporation pulses are applied between the electrodes according to selected pulse parameters for ablation of tissue in the target region. During the application of pulses, sensed values of the applied pulses are continuously received and monitored in real-time as the treatment procedure progresses. When an abnormal condition is detected based on the continuously received values of the applied pulses while the electroporation treatment procedure is progressing, the treatment procedure is temporarily paused without termination. The abnormal condition indicates either an ineffective electroporation of the tissue or an imminent excessive current such as a spark event that may exceed the capacity of the pulse generator. Rather than terminating the procedure entirely, the procedure is temporarily paused to allow the physician to adjust the pulse parameters so as to complete the procedure without starting the procedure over again.

DETAILED DESCRIPTION OF THE INVENTION

Throughout the present teachings, any and all of the one, two, or more features and/or components disclosed or suggested herein, explicitly or implicitly, may be practiced and/or implemented in any combinations of two, three, or more thereof, whenever and wherever appropriate as understood by one of ordinary skill in the art. The various features and/or components disclosed herein are all illustrative for the underlying concepts, and thus are non-limiting to their actual descriptions. Any means for achieving substantially the same functions are considered as foreseeable alternatives and equivalents, and are thus fully described in writing and fully enabled. The various examples, illustrations, and embodiments described herein are by no means, in any degree or extent, limiting the broadest scopes of the claimed inventions presented herein or in any future applications claiming priority to the instant application.

The present invention uses real-time electrical pulse monitoring during electroporation to control input settings and procedure parameters to optimize the electroporation procedure. Namely, during the electroporation procedure, the system monitors pulse parameters to determine an abnormal condition of the applied electrical pulses and whether changes should be made to the input parameters such as pulse voltage, pulse duration, pulse rate and the like. The abnormal conditions being monitored include a possibility of an imminent spark or ineffective electroporation. When an abnormal condition has been detected, the system can either pause pulse delivery to allow the physician to change the settings or automatically change one or more of the pulse parameters without user input. Once the parameter has been changed, the system then resumes the pulse delivery based on the changed settings. By doing this, electroporation pulse delivery can be optimized by maintaining effective strength pulses without exceeding pre-determined generator limits or causing errors.

Figure 1:
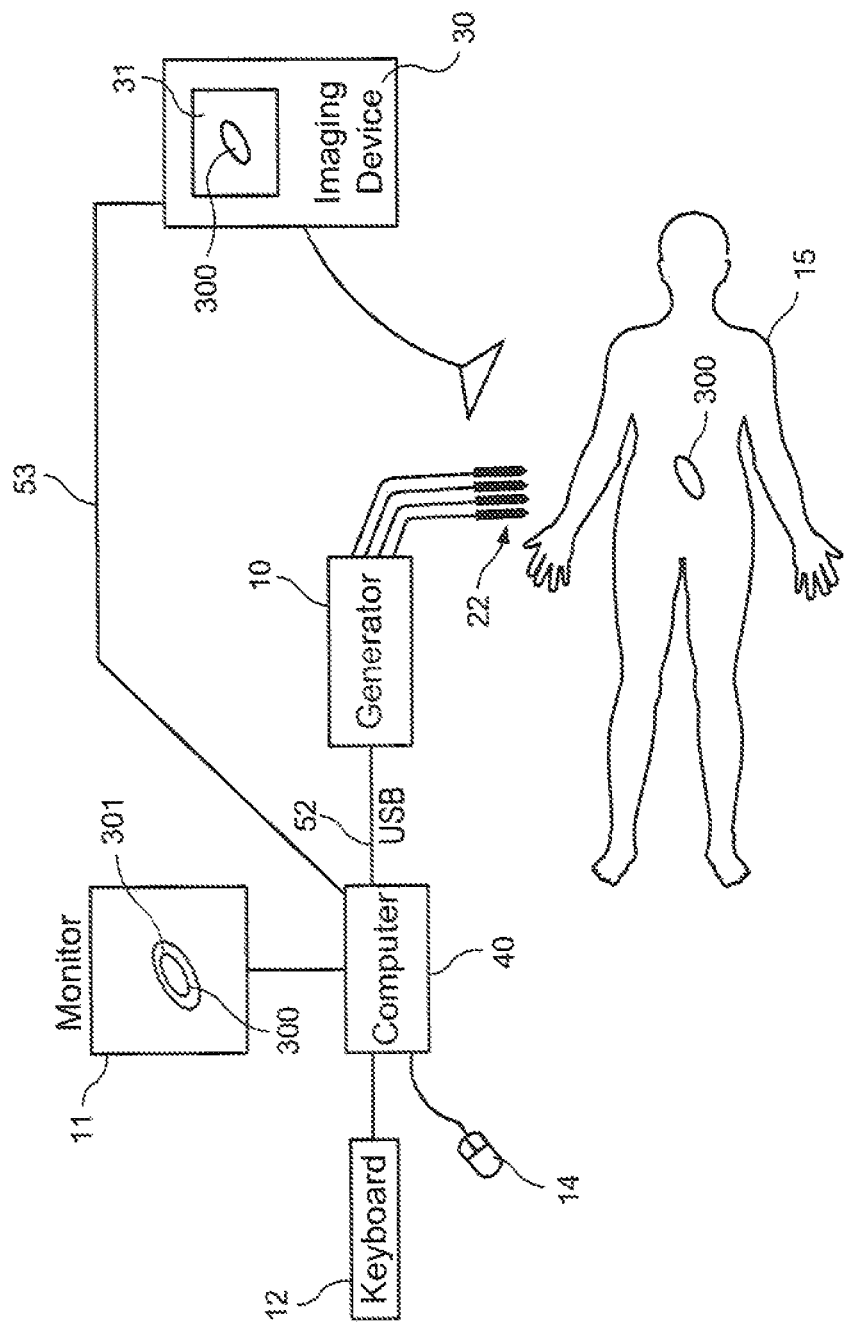
FIG. 1 is a functional block diagram of an electroporation device according to one aspect of the present invention.

One embodiment of the present invention is illustrated in FIG. 1. The components used with the present invention are illustrated in FIG. 1. One or more electrodes/probes 22 deliver therapeutic energy and are powered by a voltage pulse generator 10 that generates high voltage pulses as therapeutic energy such as pulses capable of irreversibly electroporating the tissue cells. In the embodiment shown, the voltage pulse generator 10 includes six separate receptacles for receiving up to six individual probes 22 which are adapted to be plugged into the respective receptacle. The receptacles are each labeled with a number in consecutive order. In other embodiments, the voltage pulse generator 10 can have any number of receptacles for receiving more or less than six probes.

Each probe 22 includes either a monopolar electrode, bipolar electrodes having two electrodes separated by an insulating sleeve, or multipolar electrodes having greater than two electrode surfaces separated by an insulating sleeve which can be energized simultaneously or at different times. In one embodiment, if the probe includes a monopolar electrode, the amount of exposure of the active portion of the electrode can be adjusted by retracting or advancing an insulating sleeve relative to the electrode. See, for example, U.S. Pat. No. 7,344,533, which is incorporated by reference herein. In the embodiment shown, the probes 22 are monopolar electrodes. The generator 10 is connected to a treatment control computer 40 having input devices such as keyboard 12 and a pointing device 14, and an output device such as a display device 11 for viewing an image of a target treatment area such as a lesion 300 surrounded by a safety margin 301. The therapeutic energy delivery device 20 is used to treat a lesion 300 inside a patient 15. An imaging device 30 includes a monitor 31 for viewing the lesion 300 inside the patient 15 in real time. Examples of imaging devices 30 include ultrasonic, CT, MRI and fluoroscopic devices as are known in the art.

For purposes of this application, the terms "code", "software", "program", "application", "software code", "software module", "module" and "software program" are used interchangeably to mean software instructions that are executable by a processor.

The "user" can be a physician or other medical professional. The treatment control module 54 executed by a processor outputs various data including text and graphical data to the monitor 11 associated with the generator 10.

Figure 2:
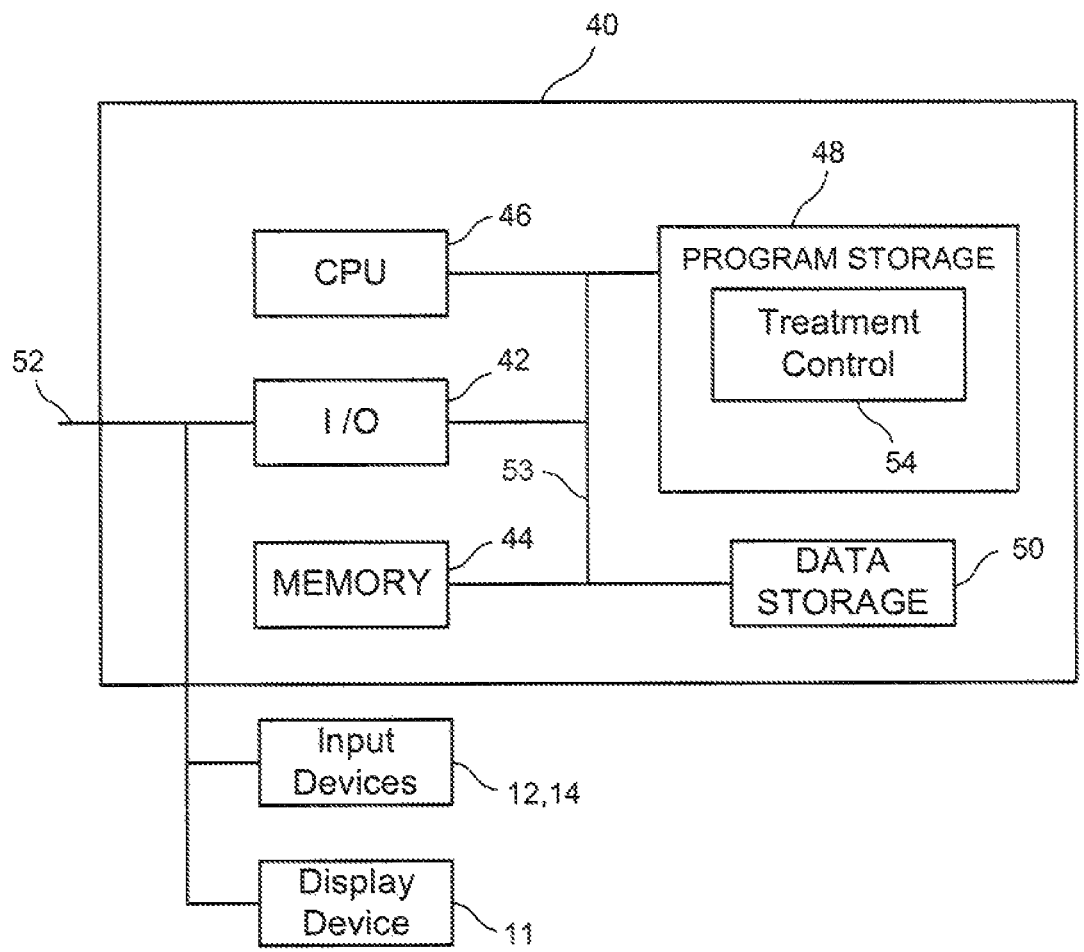
FIG. 2 is a functional block diagram of a treatment control computer of FIG. 1.

Referring now to FIG. 2, the treatment control computer 40 of the present invention is connected to the communication link 52 through an I/O interface 42 such as a USB (universal serial bus) interface, which receives information from and sends information over the communication link 52 to the voltage generator 10. The computer 40 includes memory storage 44 such as RAM, processor (CPU) 46, program storage 48 such as ROM or EEPROM, and data storage 50 such as a hard disk, all commonly connected to each other through a bus 53. The program storage 48 stores, among others, computer software (treatment control module 54) which assists a user/physician to plan for, execute, and review the results of a medical treatment procedure. The treatment control module 54, executed by the processor 46, assists a user to plan for a medical treatment procedure by enabling a user to more accurately position each of the probes 22 of the therapeutic energy delivery device 20 in relation to the lesion 300 in a way that will generate the most effective treatment zone. The treatment control module 54 can display the anticipated treatment zone based on the position of the probes and the treatment parameters. The treatment control module 54 can display the progress of the treatment in real time and can display the results of the treatment procedure after it is completed. This information can be used to determine whether the treatment was successful and whether it is necessary to re-treat the patient.

The treatment control module 54 is also adapted to detect in real-time any abnormal condition of the pulses while they are being delivered during an electroporation treatment procedure. If any abnormal condition is detected, the treatment control module 54 is programmed to pause the procedure without terminating the procedure. The pause allows a physician to change one or more of the pulse parameters through the module's user interface and to continue the procedure based on the changed parameters without terminating the procedure.

The program storage 48 stores a database/table of recommended pulse parameter changes for each of the abnormal conditions being checked by the treatment control module 54. When the pulses are being delivered and an abnormal condition is detected, the user interface portion of the control module 54 retrieves the recommended parameter changes from the database for the particular abnormal condition and presents them to the user through the display 11. The treatment control module 54 can also change criteria for detecting the abnormal condition based on initial treatment pulse parameters programmed by the user. For example, different body parts/organs or different health/age of patients may require different thresholds as their conductivity and susceptibility to irreversible electroporation may differ. Thus, for example, the absolute high current threshold value can be changed depending on the tissue type to be treated. The control module 54 may then store the changed threshold value in the program storage 48 for later use as the new criteria.

A more detailed discussion of the control module 54 will be made later herein with reference to FIGS. 5A and 5B.

Any of the software program modules in the program storage 48 and data from the data storage 50 can be transferred to the memory 44 as needed and is executed by the CPU 46.

In one embodiment, the computer 40 is built into the voltage generator 10. In another embodiment, the computer 40 is a separate unit which is connected to the voltage generator through the communications link 52. The communication link 52 can be, for example, a USB link.

In one embodiment, the imaging device 30 is a stand alone device which is not connected to the computer 40. In the embodiment as shown in FIG. 1, the computer 40 is connected to the imaging device 30 through a communications link 53. As shown, the communication link 53 is a USB link. In this embodiment, the computer can determine the size and orientation of the lesion 300 by analyzing the data such as the image data received from the imaging device 30, and the computer 40 can display this information on the monitor 11. In this embodiment, the lesion image generated by the imaging device 30 can be directly displayed on the grid 200 of the monitor 11 of the computer running the treatment control module 54. This embodiment would provide an accurate representation of the lesion image on the grid 200, and may eliminate the step of manually inputting the dimensions of the lesion in order to create the lesion image on the grid 200. This embodiment would also be useful to provide an accurate representation of the lesion image if the lesion has an irregular shape.

It should be noted that the software can be used independently of the generator 10. For example, the user can plan the treatment in a different computer as will be explained below and then save the treatment parameters to an external memory device, such as a USB flash drive (not shown). The data from the memory device relating to the treatment parameters can then be downloaded into the computer 40 to be used with the generator 10 for treatment.

Figure 3:
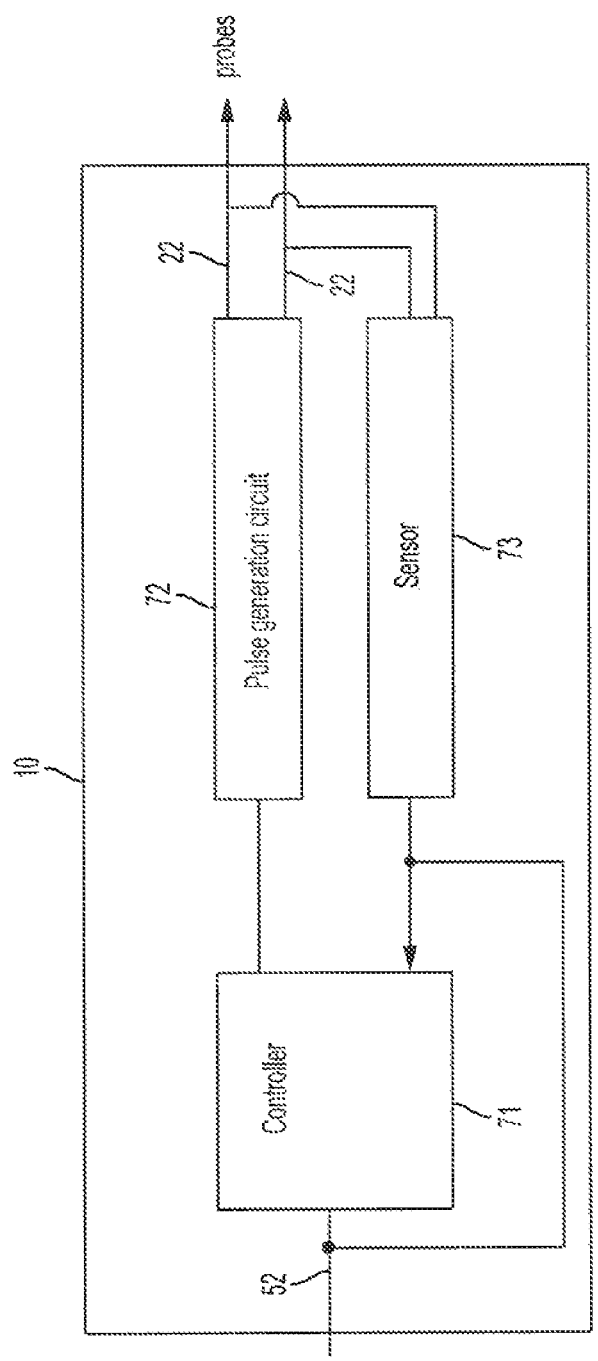
FIG. 3 is a functional block diagram of a pulse generator shown in FIG. 1.

FIG. 3 is a functional block diagram of a pulse generator 10 shown in FIG. 1. FIG. 2 illustrates one embodiment of a circuitry to detect an abnormality in the applied pulses. The abnormal condition for the applied pulses include an absolute high current, absolute low current, current creep and unstable current. A USB connection 52 carries instructions from the user computer 40 to a controller 71. The controller 71 can be a computer similar to the computer 40 as shown in FIG. 2. The controller 71 can include a processor, ASIC (application-specific integrated circuit), microcontroller or wired logic. The controller 71 then sends the instructions to a pulse generation circuit 72. The pulse generation circuit 72 generates the pulses and sends electrical energy to the probes. For clarity, only one pair of probes/electrodes are shown. However, the generator 10 can accommodate any number of probes/electrodes such as 6 probes. In the embodiment shown, the pulses are applied one pair of electrodes at a time, and then switched to another pair. The pulse generation circuit 72 includes a switch, preferably an electronic switch, that switches the probe pairs based on the instructions received from the controller 71.

A sensor 73 can sense the current and voltage between each pair of the probes in real time and communicate such information to the controller 71, which in turn, communicates the information to the computer 40. Although the treatment control module 54 houses the software code for detecting an abnormal condition of the applied pulses, it may be beneficial for the controller 71 to store such detection module as certain abnormal conditions occur quite rapidly and the speed of detection is important and in some cases critical. Accordingly, the abnormal condition detection module can be implemented in hardware as a customized wired logic as part of the controller 71.

Figure 4:
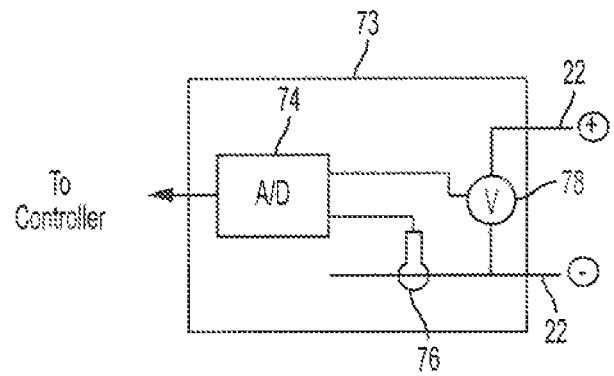
FIG. 4 is a functional block diagram of a sensor of FIG. 3.

FIG. 4 is a functional block diagram of a sensor 73 of FIG. 3. The sensor 73 includes a voltage sensor 78 connected across a pair of electrodes 22 and a current sensor 76 connected to a negative electrode (return conduit) in the pair of electrodes. Although FIGS. 3-4 show two electrodes from two wires 22, there may be multiple electrodes between the two wires 22. The sensed values are continuously received and digitized by an A/D converter 74 and transmitted to the controller 71. Preferably, the A/D converter 74 can sample the sensed values at a very fast rate and preferably at a rate of at least 100 MHz (100 million samples per second) for the control module 54 to be able to react to the abnormal conditions very quickly.

The current sensor 76 can be a Hall effect sensor/probe which is positioned around an electrode so as to measure the electric current without directly interfering with the pulse signal. Typically, the current sensor 76 is placed on the negative signal connection of the electrode pair. If the electrode pairs are switched, then only one current sensor connected at the input side of the switch is needed. Otherwise, if there are 3 pairs of electrodes, for example, and all are firing at the same time, there will be 3 current sensors so as to measure the electric current of each pair separately. In that case, the current from the three sensors will need to be added.

The voltage sensor 78 can be a conventional voltage divider, comprised of two serially connected resistors, that measures a voltage drop across a known resistance value. The voltage sensor 78 uses resistors which are of much higher resistance than the tissue (kΩ-MΩ, versus tissue, which is hundreds of Ω), and thus induces negligible effect on the strength of the pulses delivered to the tissue. A correction factor is calculated for the divider circuit based on the resistances of the two resistors in the voltage divider circuit and the resistance of the load (tissue resistance) to determine the true delivered voltage to the tissue based on the measured voltage drop across the resistor.

A method of ablating a tissue site by electroporation with real-time pulse parameter monitoring during an electroporation procedure will now be explained with reference to FIGS. 5A-5B.

The steps executed are part of the treatment control module 54 which can be part of the computer 40 or a part of the controller 71 in the pulse generator 10 itself for faster response. Referring to FIG. 5A, in step 42, the treatment control module 54 graphically interacts with the user to receive treatment parameters which include voltage between electrodes, electrode separation distance, firing sequence among the electrode pairs, pulse delivery/firing rate, pulse duty cycle, number of pulses in a pulse set/train, number of pulse sets/trains, inter-pulse delay, inter pulse train delay, electrode exposure length, pulse parameter changes for each abnormal condition and the like. In step 43, a user/physician positions the electrodes 22 at a tissue site such that the electroporation field covers the target region. The target region is now ready to be treated.

In step 44, based on the received parameters, the pulse control module 54 instructs the controller 71 in the pulse generator 10 to start an electroporation procedure. In step 46, under the control of the controller 71, the pulse generation circuit 72 starts delivering electroporation pulses through the electrodes 22 that have been placed in the patient.

In step 48, while the pulses are being delivered, the treatment control module 54 continuously receives the voltage and current values from the sensors 76 and 78 and monitors the received values in real-time for a series of abnormal conditions which may indicate a potential problem in effective delivery of pulses. The abnormal conditions to be detected will be discussed in more detail later with reference to FIG. 5B.

If an abnormal condition is detected, control passes to step 56, in which the treatment procedure is paused. It is important to note that the procedure is merely paused and the computer 40 remembers all of the pulse parameters and the point at which the procedure is stopped so that the procedure can be resumed where it paused.

Figure 11:
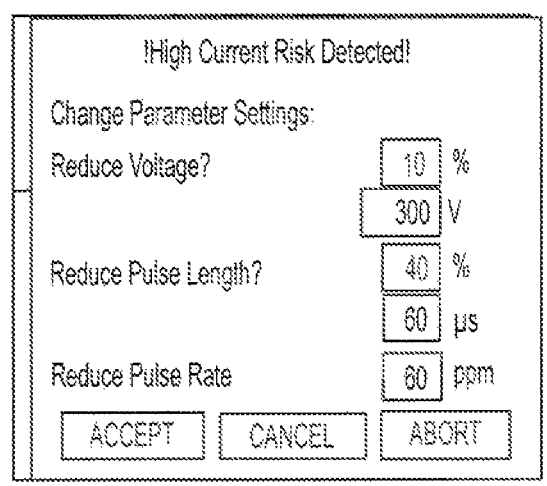
FIG. 11 is an exemplary screenshot of a recommended parameter change presentation.

As discussed above, the computer 40 stores in the storage 50 various recommended pulse parameter changes for each abnormal condition to be detected. Once the treatment procedure is paused, the treatment control module 54 in step 58 retrieves the recommended parameter changes and presents them to the user in the display. An exemplary screen shot of the presentation is shown in FIG. 11. FIG. 11 shows that the control module 54 has detected a high current risk and displayed the suggested parameter changes which have been retrieved from the storage 50. Specifically, the recommended parameter changes shown are a 10% reduction in voltage, 40% reduction in pulse length, and reduction of pulse rate to 60 pulses per minute. Typically, the recommended parameter changes are voltage reduction of 5-10%, and 30-50% reduction in pulse length.

The user has a choice of accepting the recommended changes, changing the recommended changes and aborting the electroporation procedure. Acceptance can be submitted by clicking on the ACCEPT button. Changing the recommended changes involves clicking the CANCEL button, inputting his own changes and then clicking the ACCEPT button. Aborting the procedure is done by simply clicking on ABORT button.

In step 60, the control module 54 determines whether the treatment procedure should be resumed based on the user input from step 58. If the answer is yes, then control passes to step 46 and the pulse generation circuit 72 resumes the treatment procedure with delivery of pulses based on the adjusted parameters. If the answer is no, then control passes to step 54 which terminates the treatment procedure without completion.

At step 48, if no abnormal conditions were detected, control passes to step 50. At step 50, the control module 54 determines whether the delivery of pulses has been completed. If the answer is no, then control passes to step 46 and delivery of pulses continues. If the answer is yes, then control passes to step 54 which completes and terminates the treatment procedure normally.

Figure 5B:
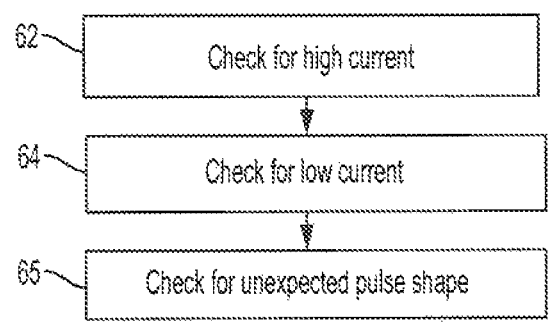
FIG. 5B is a flowchart of a method of detecting an abnormal condition of delivered electrical pulses.
Figure 5A:
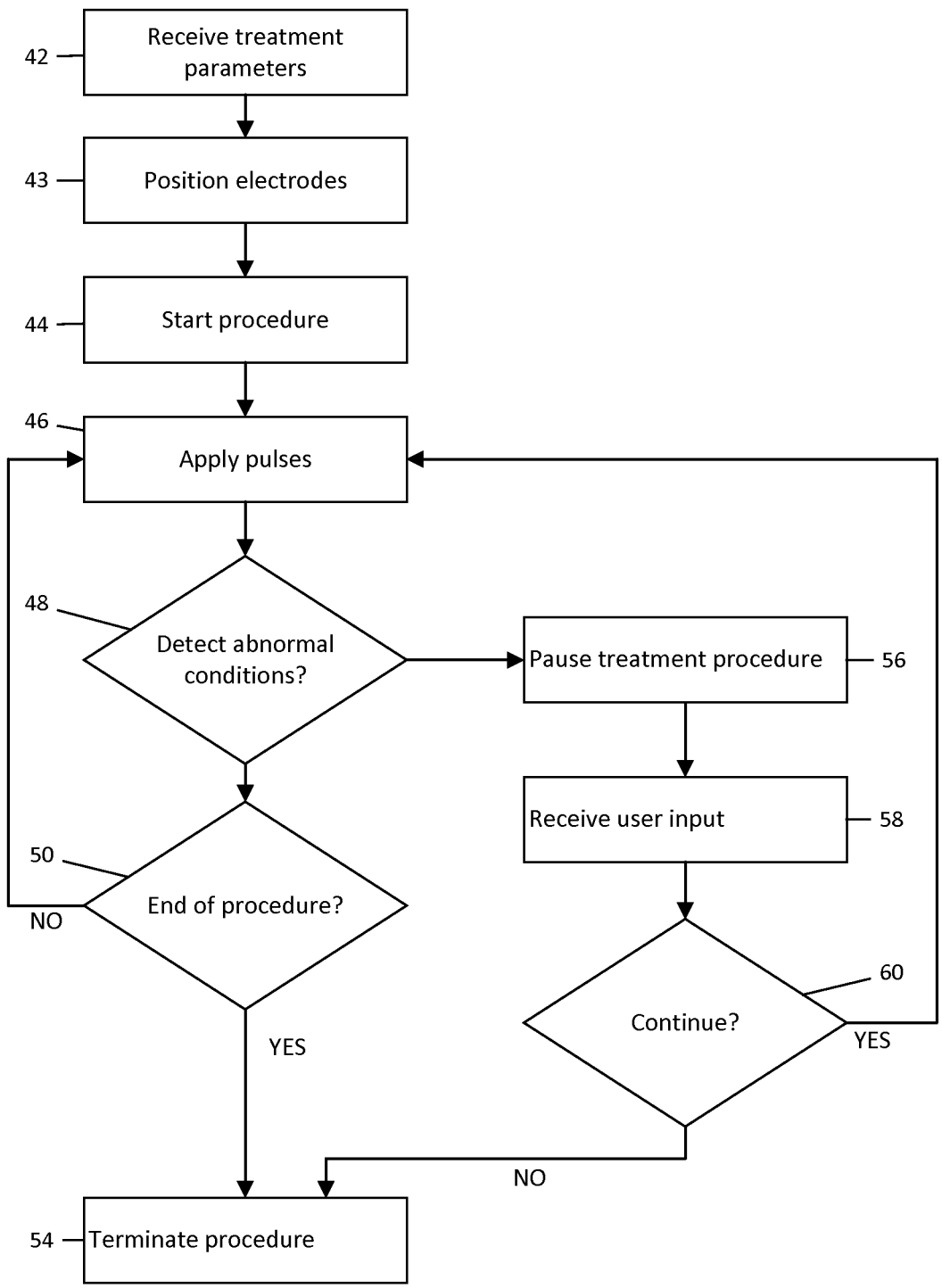
FIG. 5A is a flowchart of a method of ablating a tissue site by electroporation with real-time pulse parameter monitoring during an electroporation procedure.
Figure 7A:
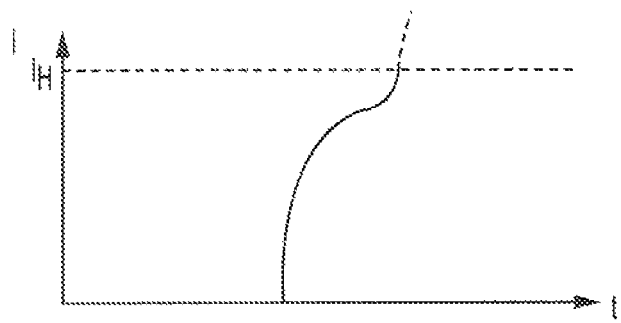
FIGS. 7A and 7B illustrate an electrical pulse having an absolute high current and absolute low current, respectively.

FIG. 5B is a flowchart of a method of detecting an abnormal condition of delivered electrical pulses, which describes step 48 of FIG. 5A in more detail. Step 62 detects whether the current of the delivered pulses reaches a high current threshold value. As shown in FIG. 7A, the high current threshold value $I_H$ can be 50 amps. When the delivered pulse reaches 50 amps at any time during the pulse, the abnormal condition is triggered.

Figure 7B:
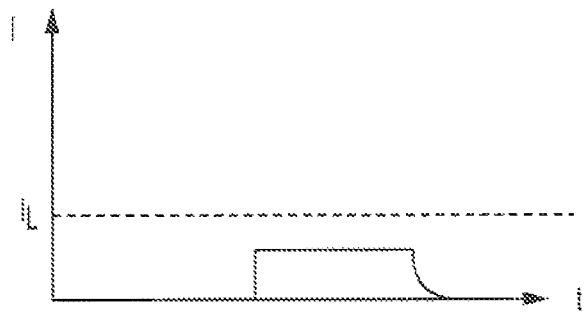

Step 64 detects whether the delivered pulses have an absolute low current below a low current threshold value $I_L$. As shown in FIG. 7B, the low current threshold value can be 5 amps. When the delivered pulse reaches 5 amps or below at any time during the pulse, the abnormal condition is triggered. If the waveform is flat, it may indicate an insignificant or sub-optimal electroporation, and thus energy delivery should be increased, for example, by 10%.

Step 65 detects whether the delivered pulses have an unexpected pulse shape in order to predict a potential problem in a system shutdown or ineffective ablation. When this condition is detected, it indicates that a predetermined current threshold value (e.g., 50 amps) is about to be exceeded.

Figure 6:
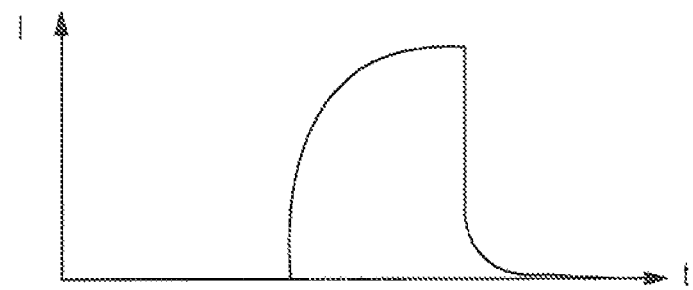
FIG. 6 illustrates an expected electrical pulse.

To monitor and detect unexpected pulse shapes, it may be useful to understand what an expected pulse should look like. Due to the progressive electroporation of tissue cells and a small rise in temperature within the delivery of an electroporation pulse, electrical conductivity of the tissue rises. Consequently, electrical currents typically rise in a decaying fashion within the pulse (approaching a plateau) as shown by FIG. 6, for example.

Similarly, between successive pulses, the current also expectedly rises due to the rise in tissue conductivity. An absence of corresponding current rise over a given number of pulses may serve as an indicator of insufficient energy intensity, and thus induce the need to increase pulse parameter strength.

Figure 8A:
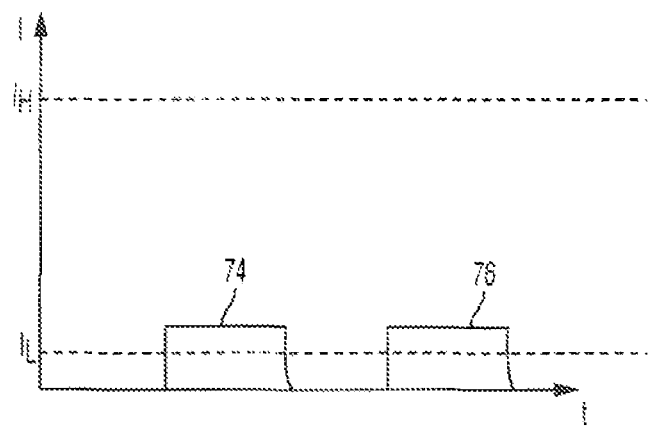
FIGS. 8A and 8B illustrate electrical pulses having no expected rise in current.

Thus, one of the unexpected pulse shapes is a stable waveform with very little increase (e.g., less than 5% threshold increase) or no increase in current either within a pulse or between pulses. As shown in FIG. 8A, each of pulses 74 and 76 has substantially no intra-pulse or inter-pulse current rise. In one embodiment, there is substantially no inter-pulse or intra-pulse rise if the rise is 5% or less. The control module 54 detects either condition as an unexpected pulse/waveform shape.

Figure 8B:
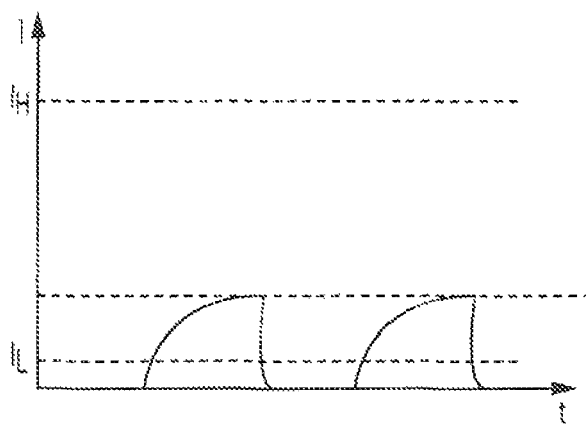

FIG. 8B illustrates another example of an inter-pulse stable waveforms. Even though each waveform 78,80 has an expected rise in current, the change in current between the two pulses is virtually zero. In that case, the control module 54 detects the condition as an unexpected pulse shape.

One way to implement the steady intra-pulse waveform as shown in FIG. 8A is to take two measurements near the leading and falling edges (e.g., measurements at t=5 μsec and t=95 μsec for a 100 μsec pulse) and compare against a predetermined threshold current value (e.g., 5%). If the current difference is less than 5% over the measurement taken at t=5, then the pulse is considered to have an unexpected pulse shape.

Similarly, one way to implement the steady inter-pulse waveform as shown in FIG. 8B is to take two measurements near the falling edges of the pulses 78,80 (e.g., measurements at t=95 μsec for a 100 μsec pulse) and compare against a predetermined threshold current value (e.g., 5%). If the current difference is less than 5% over the measurement taken at t=95 μsec for waveform 78, then the pulse is considered to have an unexpected pulse shape.

Another one of the unexpected pulse shapes is due to a condition called the "current creep". This is one of the most common phenomena in electroporation pulse delivery which causes issues for clinical (and pre-clinical) applications.

Figure 9:
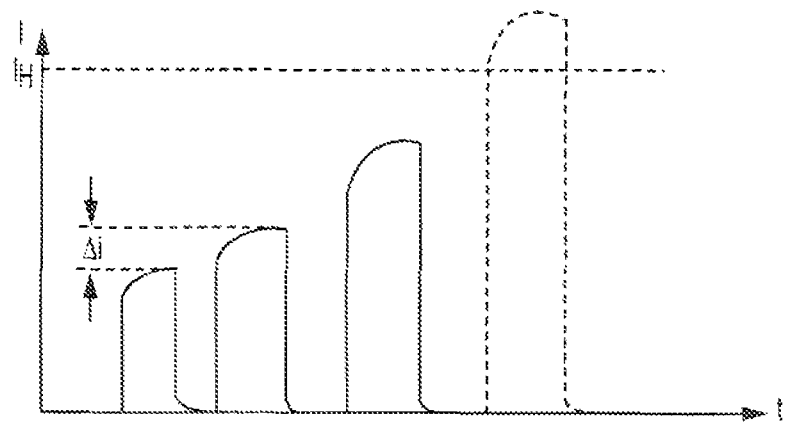
FIG. 9 illustrates an electrical pulse having a current creep.

Normally, successive pulses are expected to have a slightly higher current because as electroporation progresses, the conductivity of tissue rises due to electroporation and because the temperature tends to increase. However, an excessive rise in current indicates an "abnormal current creep" as shown in FIG. 9 that could lead to the subsequent pulses to exceed the maximum current value $I_H$. Alternatively, an abnormal current creep can include a condition where the current creep can be slow but the current value is near the maximum current value $I_H$.

For example, let's assume that the electroporation treatment procedure involves a 100 pulse protocol with 10 sets of pulses with 10 pulses in each set. If the average current for sets 1 through 4 are respectively 30 amps, 35 amps, 42 amps and 48 amps, then there is a high probability that the next set will exceed the maximum high current threshold $I_H$ of 50 amps. Sometimes an abnormal current creep can be subtle such as 45, 45.5, 46 and then 48 amps. Because, 48 amps is near the maximum current value $I_H$ of 50 amps, this may be a cause for concern. In these cases, the control module at step 65 detects the current creep as an abnormal condition in real-time before the fifth set of pulses is delivered.

There are several methods to implement the detection of an abnormal current creep. A first method is to measure the maximum current in each pulse and examine the difference between two successive pulse currents. If the difference is above a threshold difference current value, e.g., predetermined threshold rate of 7 amps, then that means the current is rising too fast. This situation may trigger the abnormal condition.

A second method is to calculate the above value or a 3-5 point moving average of current values (measured at the maximum current value in each pulse) or use a regression analysis to predict the next current value. The current values can be continuously sampled within a pulse (e.g. 100 sampling points per pulse) and the highest current value for each pulse can be used for the moving average and regression analysis.

If the predicted current value is higher than the maximum current threshold $I_H$, it will trigger the abnormal condition. For example, a 3 point moving average can be used and its slope can be examined to see if the next pulse might cause the current to exceed the maximum current threshold value. If so, the abnormal condition can be triggered.

The first and second methods above can be combined so that the unexpected pulse shape (and thus an abnormal condition) is triggered when both conditions are satisfied. In other words, if the difference between two successive pulse currents is above the threshold difference current value and the maximum current of the latest delivered pulse is above the maximum high current threshold value $I_H$, then the abnormal condition (abnormal current creep) is triggered by the control module 54.

Figure 10A:
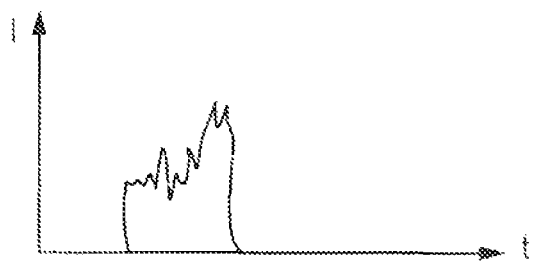
FIGS. 10A and 10B illustrate an electrical pulse having an unstable current.

Another one of the unexpected pulse shapes is an unstable waveform as illustrated in FIG. 10A. It is not uncommon for baseline tissue properties or their changes in response to electroporation pulses to cause highly unstable and unpredictable waveforms. This can result in sudden spikes in current that may exceed safe or generator-limited conditions.

One method to implement the unstable waveform condition is to sample the current value of 100 data points within a single delivered pulse, calculate a standard deviation and comparing it to a threshold instability criteria, e.g., threshold deviation value of 10 amps.

The standard deviation method can be combined with a maximum current threshold value $I_H$, e.g., 50 amps, as described with reference to FIG. 7A, so that the abnormal condition is triggered when both conditions are satisfied.

Figure 10B:
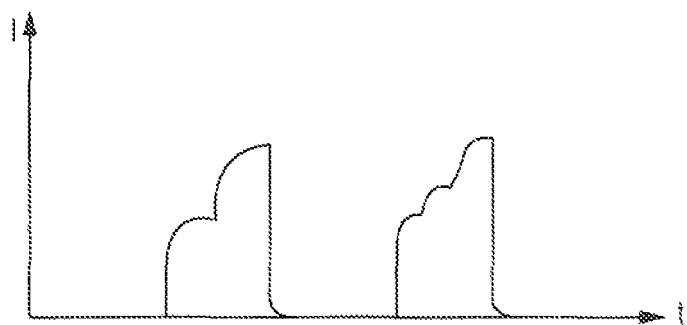

Yet another one of the unexpected pulse shapes is a multi-tiered waveform as shown in FIG. 10B. This is a step-wise sudden and sharp increase in electrical current during a pulse. This can even occur in a repeated and thus semi-predictable manner. It most commonly occurs in a two-phase system, but can have multiple "tiers" within the pulse. Since these waveforms pose a risk to continued pulse delivery, the best approach is to reduce the voltage or pulse length (or cease pulse delivery among that pair of electrodes) as will be explained later herein. Again, the detection of an unstable waveform can be combined with a maximum threshold current value $I_H$, e.g., 40 amps, so that the abnormal condition is triggered when both conditions are satisfied.

As discussed above, real-time detection of an abnormal condition that may lead to a sudden spark across the electrodes or ineffective treatment allows the present invention to pause the treatment procedure to allow the user to adjust the pulse parameters to mitigate such risks without having to terminate the procedure.

If IRE pulses are biphasic pulses, the absolute value of each biphasic pulse can be compared from one pulse to the next, or if orientation of polarity alters the current behavior, then pulses of the same orientation can be compared.

The above disclosure is intended to be illustrative and not exhaustive. This description will suggest many modifications, variations, and alternatives may be made by ordinary skill in this art without departing from the scope of the invention. Those familiar with the art may recognize other equivalents to the specific embodiments described herein. Accordingly, the scope of the invention is not limited to the foregoing specification.

What is claimed is:

1. A system comprising:
    a processor;
    a pulse generator coupled to the processor and to be operatively coupled to at least two electrodes, the at least two electrodes to be placed in a target region of a tissue site of a patient; and
    a memory comprising instructions, which when executed by the processor cause the system to:
        program the pulse generator to generate a plurality of electrical pulses between the at least two electrodes to ablate cells within the target region;
        receive an indication of a current from a current sensor, an indication of a voltage from a voltage sensor, or an indication of the current and the voltage from the current sensor and the voltage sensor associated with the plurality of electrical pulses;
        detect an abnormal condition of an irreversible electroporation (IRE) treatment procedure based in part on the indication of the current, the indication of the voltage, or the indication of the current and the voltage;
        pause generation of at least one of the plurality of electrical pulses in response to detection of the abnormal condition;
        receive an indication to resume the IRE treatment procedure; and
        resume the IRE treatment procedure including resuming generation of the at least one of the plurality of electrical pulses to complete the IRE treatment procedure.

2. The system of claim 1, wherein the abnormal condition comprising a waveform indicating the current is below a threshold level, an imminent electrical spark event, or an unexpected pulse or waveform shape.

3. The system of claim 1, wherein when executed by the processor the instructions cause the system to sample a plurality of current values, a plurality of voltage values, or a plurality of current values and a plurality of voltage values.

4. The system of claim 1, wherein when executed by the processor the instructions cause the system to store criteria for detecting the abnormal condition based on a set of initial treatment pulse parameters.

5. The system of claim 1, wherein the abnormal condition indicates an ineffective irreversible electroporation of the cells within the target region.

6. The system of claim 1, wherein when executed by the processor the instructions cause the system to display, on a display device, a set of optional adjustments in which a user may select to adjust at least one parameter of the plurality of electrical pulses.

7. The system of claim 1, wherein when executed by the processor the instructions cause the system to:
generate a first visual indication that the abnormal condition has been detected;
identify a set of optional adjustments in which a user may select to adjust at least one parameter of the plurality of electrical pulses such that the plurality of electrical pulses maintain effective strength to result in irreversible electroporation within the target region without exceeding limitations of the pulse generator;
generate a second visual indication of the set of optional adjustments;
display, on a display device, the first visual indication and the second visual indication;
receive, from the user, an indication to adjust the at least one parameter of the plurality of electrical pulses; and
adjust the at least one pulse parameter responsive to receiving the indication.

8. The system of claim 1, wherein when executed by the processor the instructions cause the system to:
identify a subset of the plurality of electrical pulses that were not effectively delivered, the subset of the plurality of electrical pulses comprising the at least one of the plurality of electrical pulses;
resume the IRE treatment procedure including resuming generation of the subset of the plurality of electrical pulses to complete the IRE treatment procedure.

9. The system of claim 1, comprising to generating the at least one of the plurality of electrical pulses with parameters from the paused IRE treatment procedure to resume the IRE treatment procedure.

10. A system, comprising:
a processor;
a pulse generator coupled to the processor and to be operatively coupled to at least two electrodes to be introduced near a target region of a tissue site of a patient;
at least one of:
a current sensor to be operatively coupled to at least a first one of the at least two electrodes, the first one of the at least two electrodes to sink current delivered by at least one other of the at least two electrodes, the current sensor to measure an electrical current returning to the pulse generator via the first one of the at least two electrodes, or
a voltage sensor to be operatively coupled to the at least two electrodes and to measure a voltage between the at least two electrodes; and
a memory comprising instructions, which when executed by the processor cause the system to:
program the pulse generator to generate a plurality of electrical pulses to irreversibly electroporate tissue in the target region;
receive an indication of the current from the current sensor, an indication of the voltage from the voltage sensor, or an indication of the current and the voltage from the current sensor and the voltage sensor;
detect an abnormal situation of an irreversible electroporation (IRE) treatment procedure based in part on the indication of the current, the indication of the voltage, or the indication of the current and the indication of the voltage;
pause the IRE treatment procedure including pausing generation of at least one of the plurality of electrical pulses in response to detection of the abnormal situation; and
resume generation of the at least one of the plurality of electrical pulses to resume the IRE treatment procedure.

11. The system of claim 10, wherein when executed by the processor the instructions cause the system to detect the abnormal situation based on a change of the measured current.

12. The system of claim 10, wherein the abnormal situation is an incomplete irreversible electroporation ablation of the tissue in the target region.

13. The system of claim 10, wherein when executed by the processor the instructions cause the system to:
generate a first visual indication that the abnormal situation has been detected;
identify a set of optional adjustments in which a user may select to change at least one pulse parameter of the plurality of electrical pulses;
generate a second visual indication of the set of optional adjustments; and
display, on a display device, the first visual indication and the second visual indication.

14. The system of claim 13, wherein when executed by the processor the instructions cause the system to sample a plurality of current values, a plurality of voltage values, or a plurality of current values and a plurality of voltage values of the plurality of electrical pulses.

15. The system of claim 13, wherein the at least one pulse parameter may comprise any of the following:
a voltage between the at least two electrodes;
an electrode separation distance;
an activation sequence between the at least two electrodes; a pulse delivery rate; a pulse duty cycle;
a number of pulses in a pulse set; a number of pulse sets; an inter-pulse delay; an inter pulse train delay; or
an electrode exposure length.

16. The system of claim 10, comprising to generating the at least one of the plurality of electrical pulses with parameters from the paused IRE treatment procedure to resume the IRE treatment procedure.

17. A method, comprising:
generating, at a pulse generator, a plurality of electrical pulses to be applied between at least two electrodes placed in a target region;
measuring at least one of:
an electrical current, or
a voltage magnitude;
receiving, an indication of the electrical current, an indication of the voltage magnitude, or an indication of the electrical current and the voltage magnitude;
detecting an abnormal condition of an irreversible electroporation (IRE) procedure based in part on the indication of the electrical current, the indication of the voltage magnitude, or the indication of the electrical current and the indication of the voltage magnitude;

pausing the generation of a subset of the plurality of electrical pulses in response to the abnormal condition to pause the IRE procedure; and resuming generation of the subset of the plurality of electrical pulses to complete the IRE procedure.

18. The method of claim 17, wherein detecting the abnormal condition comprises detecting the abnormal condition when the indication of the electrical current is less than or equal to a predetermined current threshold value or when the indication of the voltage magnitude is less than or equal to a predetermined voltage threshold value.

19. The method of claim 17, wherein detecting the abnormal condition comprises detecting the abnormal condition when the indication of the electrical current is greater than or equal to a predetermined current threshold value or when the indication of the voltage magnitude is greater than or equal to a predetermined voltage threshold value.

20. The method of claim 17, further comprising changing at least one pulse parameter of the plurality of electrical pulses to prevent a potential electrical spark event between the at least two electrodes from occurring.

21. The method of claim 20, wherein pausing generation of the plurality of electrical pulses comprises preventing a shutdown of the pulse generator as a result of the potential electrical spark event.

22. The method of claim 17, further comprising determining criteria for detecting the abnormal condition based on a set of treatment pulse parameters;

wherein the treatment pulse parameters may comprise any of the following:
  a voltage between the at least two electrodes; an electrode separation distance;
  an activation sequence between the at least two electrodes;
  a pulse delivery rate;
  a pulse duty cycle;
  a number of pulses in a pulse set;
  a number of pulse sets;
  an inter-pulse delay;
  an inter pulse train delay; or
  an electrode exposure length.

23. The method of claim 17, comprising generating the subset of the plurality of electrical pulses with parameters from the paused IRE treatment procedure to resume the IRE treatment procedure.

* * * * *